United States Patent
Lenzen et al.

(10) Patent No.: US 7,276,576 B1
(45) Date of Patent: Oct. 2, 2007

(54) MAMMALIAN ICYP (IODOCYANOPINDOLOL) RECEPTOR AND ITS APPLICATIONS

(75) Inventors: Gerlinde Lenzen, Paris (FR); Arthur Donny Strosberg, Paris (FR); Toshinari Sugasawa, Osaka (JP); Shigeaki Morooka, Hyogo (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 09/319,724

(22) PCT Filed: Dec. 12, 1997

(86) PCT No.: PCT/EP97/07339

§ 371 (c)(1),
(2), (4) Date: Sep. 8, 1999

(87) PCT Pub. No.: WO98/26065

PCT Pub. Date: Jun. 18, 1998

(30) Foreign Application Priority Data

Dec. 12, 1996 (EP) .................................. 96402719

(51) Int. Cl.
- *C07K 14/705* (2006.01)
- *C07K 14/435* (2006.01)
- *C07H 21/04* (2006.01)
- *G01N 33/567* (2006.01)
- *C12P 21/06* (2006.01)

(52) U.S. Cl. ................. 530/350; 530/300; 530/388.22; 536/23.5; 435/7.21; 435/69.5; 435/252.3; 435/320; 436/501

(58) Field of Classification Search .................... 435/6, 435/7.1, 7.21, 69.1, 252.3, 320.1; 530/350, 530/300; 536/23.5; 436/501; 514/2
See application file for complete search history.

(56) References Cited

OTHER PUBLICATIONS

Bowie et al., 1990, Science 247:1306-1310, especially p. 1306.*
Alexander et al., Proc. Natl. Acad. Sci. 89(3352-3356)1992.*
Sugasawa-T et al., Gene 273(227-237)2001.*
Sugasawa-T et al., J. Biol. Chem. 272(34)21244-21252, 1997.*
Sugasawa-T et al., Agents Actions 37(232-237)1992.*
Charles Auffray et al., IMAGE: integrated molecular analysis of the human genome and its expression, Life Sciences 1995, pp. 263-272.
Toshinari Sugasawa, In vitro study of a novel atypical β-adrenoceptor agonist, SM-11044, European Journal of Pharmacology, vol. 216, 1992 Elsevier Science Publishers, pp. 207-215.
Sugasawa et al, J. Biol. Chem., 272(34):21244-21252 (Aug. 1997).
Strosberg et al, Trends Pharm. Sci., 17:373-381 (Oct. 1996).
Sugasawa, et al., "Existence of atypical beta-adrenoceptor on guinea pig eosinophil", in Recent advances in cellular and molecular biolog., 1. World congress of C.M.B., Paris, Sep. 1-7, 1991, Wegmann RJ and Wegmann MA Eds., Peeters Press, Leuven, Belgium 1992.
Sugasawa et al., Agents and Actions, 37:232-237 (1992).
Bianchetti et al., Br. J. Pharmacol., 100:831-839 (1990).
Challis et al., Biochemical Pharmacology, 37(5):947950 (1988).

* cited by examiner

*Primary Examiner*—Janet L. Andres
*Assistant Examiner*—Michael Brannock
(74) *Attorney, Agent, or Firm*—Morgan, Lewis & Bockius LLP

(57) ABSTRACT

An isolated and substantially pure mammal polypeptide different from known adrenergic, serotonine and dopamine receptors, existing at least on mammalian muscle and eosinophils membranes, for instance in rat, guinea pig and humans. The invention also relates to plasmids containing the genes coding for said polypeptide, to host cells transformed by genes coding for the above mentioned polypeptide, to nucleotide probes capable of hybridizing with the genes coding for the above mentioned polypeptide, and to polyclonal and monoclonal antibodies directed against the above mentioned polypeptide. Said polypeptide is characterized in that it contains sites such that when said sites are exposed at the surface of a cell, they are able of binding iodocyanopindolol (ICYP) under blockage of α, β1, β2, β3-AR, serotonine $5-HT_{1A}$ and serotonine $5-HT_{1B}$ receptors, said binding being saturable, reversible, able to be displaced by a β-adrenergic receptor agonist SM-11044 with stereoselectivity but not by isoproterenol, norepi-nephrine, epinephrine, serotonine, dopamine or BRL-37344, and not being blocked by propranolol, said polypeptide (1) having an apparent molecular weight of about 30-40 kDa when labeled with $^{125}I$-iodocyanopindolol after photoaffinity labeling and separation by electrophoresis and an apparent molecular weight of about 60-80 kDa in Western blot, and (2) generating a fragment having the following formula $DPX_1FFQHRIHX_2FSIFNX_3$ by acidic cleavage, wherein $X_1$ represents S (SEQ ID NO.5) or X (SEQ ID NO.6), $X_2$ represents V (SEQ ID NO.6) or W (SEQ ID NO.5) and $X_3$ represents S (SEQ ID NO.5) or H (SEQ ID NO.6), said polypeptide being present at least on muscles and eosinophils membranes and being a non-adrenergic receptor.

15 Claims, 33 Drawing Sheets

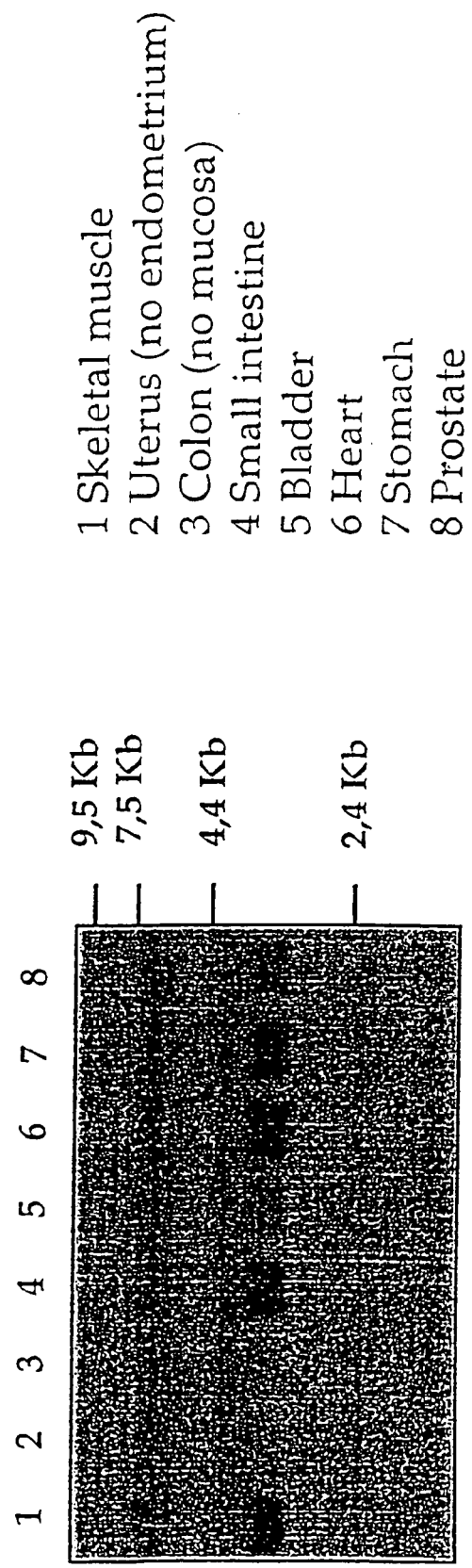
FIGURE 18.A

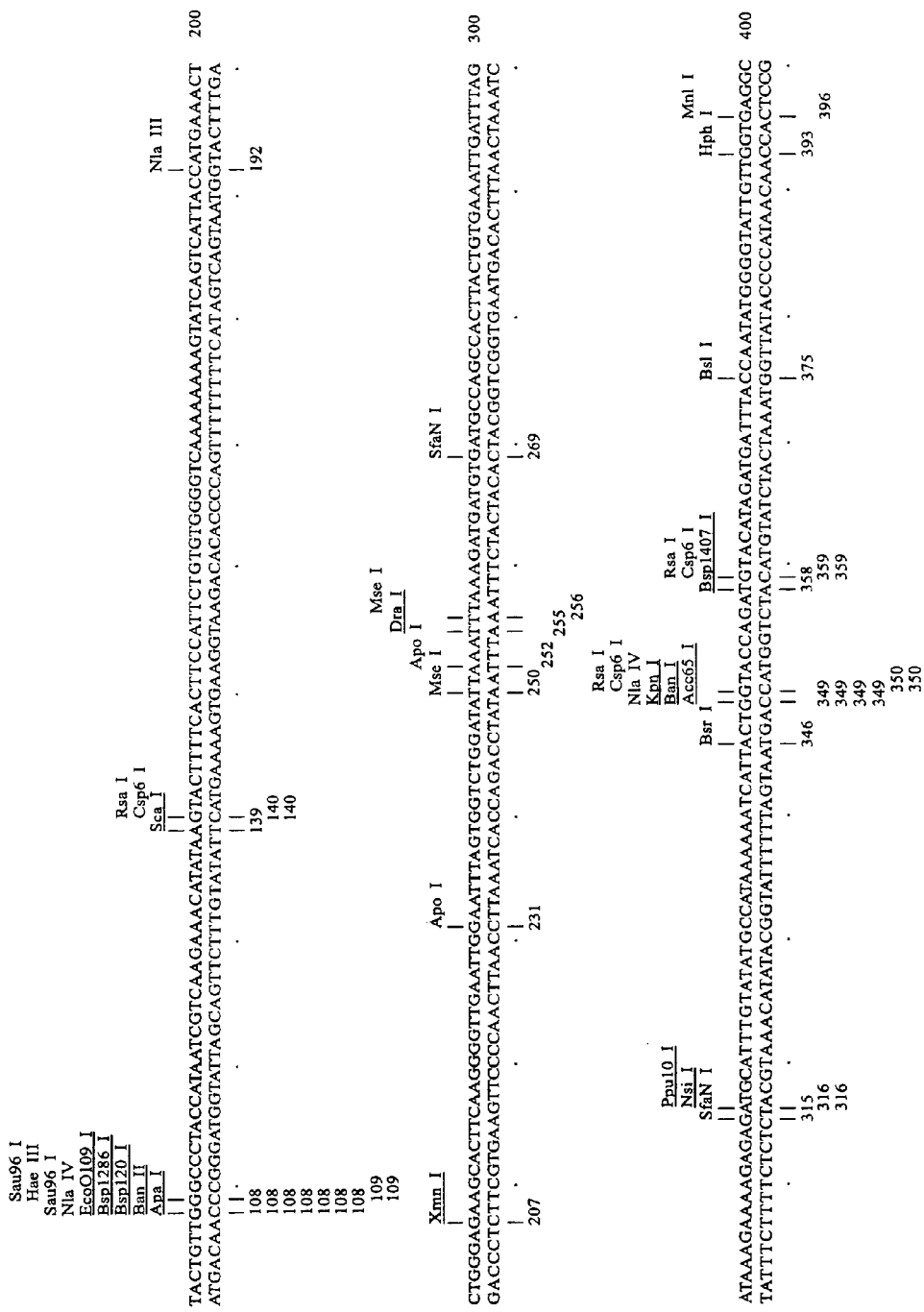

Fig. 19 F

```
                                                 Nla III
                                                 NspC I
                                                 Nsp7524 I
                       SfaN I                    Nsp I
                       BspW I                    Afl III
                       Fnu4H I                   | | |
                       Bbv I                     | | |
                       | |                       | | |
GGTGGCAATGGACAAGTTTTCTCTGCTGCTCAATCAACTGCAATCTATGTTTACTACTATTTTTCAAAACAAAGATGTATGGCTT  1600
CCACCGTTACCTGTTCAAAAGAGAGACGTAGTTGACGTTAGATACAAATGATGATAAGGAAAAATGATGATAAAAAGTTTGTTTCTACATACCGAA
                                                 1527      1552
                                                 1527      1552
                                                   1530    1552
                                                   1530    1552
                                                           1553

Nla III
                                                                                Mae III
                               Sty I                                            | |
                       Aci I   BsaJ I                                           | |
Tth111 II              |       | |                                              | |
ATTTCAAACATCATTTACTTTGGATATATGGCGGGTATTTAGCACAGCCTTGGGGATAAATGTGTGAGCGATTGGTTACATGGAACAAGTGCCTTGTC  1700
TAAAGTTTGTAGTAAAATGAAACCTATATACCGCCCATAAATCGTGTCGGAACCCCTATTTACACACTCGCTAACCAATGTACCCTGTTCACGGAAACAG
|                              1632                                            1675
1605                            1632                                            1679

ScrF I       Sau3A I
                                 EcoR II      Mbo I
                       BsmA I    Dsa V        Dpn II
                       Bsa I     BstN I       Dpn I
            Bfa I      | |       BstK I       Alw I
            |          | |       | | | |      | | | |
CGAAAAATCTATACTAATGTGAAAAATTGACTAGAGACCCAAGAAAACCTGGAACTTTGGATCAATTTCTTTTCATAGGGGTGGAACTTGCACAGCAAAA  1800
GCTTTTTAGATATGATTACACTTTTAACTGATCTCTGGGTTCTTTGGACCTTGAAACCTAGTTAAAGAAAAAGTATCCCCACCTTGAACGTGTCGTTTT
            1730       1733                  1747           1758
                       1733                  1747           1759
                                              1747           1759
                                              1747           1759
```

| Enzyme | Site | <-- | Pos. | --> |
|---|---|---|---|---|
| BstU I | cg/cg | 4 | 5 | 1796 |
| Hha I | gcg/c | 5 | 6 | 1795 |
| HinP I | g/cgc | 5 | 6 | 1795 |
| Ava I | c/ycgrg | 39 | 40 | 1761 |
| Sma I | ccc/ggg | 39 | 40 | 1761 |
| Xma I | c/ccggg | 39 | 40 | 1761 |
| BsaA I | yac/gtr | 61 | 62 | 1739 |
| Apa I | gggcc/c | 107 | 108 | 1693 |
| Ban II | grgcy/c | 107 | 108 | 1693 |
| Bsp120 I | g/ggccc | 107 | 108 | 1693 |
| EcoO109 I | rg/gnccy | 107 | 108 | 1693 |
| Sca I | agt/act | 138 | 139 | 1662 |
| Xmn I | gaann/nnttc | 206 | 207 | 1594 |
| Dra I | ttt/aaa | 254 | 255 | 1546 |
| Nsi I | atgca/t | 315 | 316 | 1485 |
| Ppu10 I | a/tgcat | 315 | 316 | 1485 |
| Acc65 I | g/gtacc | 348 | 349 | 1452 |
| Ban I | g/gyrcc | 348 | 349 | 1452 |
| Kpn I | ggtac/c | 348 | 349 | 1452 |
| Bsp1407 I | t/gtaca | 357 | 358 | 1443 |
| Spe I | a/ctagt | 488 | 489 | 1312 |
| BspD I | at/cgat | 579 | 580 | 1221 |
| Cla I | at/cgat | 579 | 580 | 1221 |
| Hinf I | g/antc | 622 | 623 | 1178 |
| Tfi I | g/awtc | 622 | 623 | 1178 |
| Avr II | c/ctagg | 763 | 764 | 1037 |
| Drd I | gacnnnn/nngtc | 810 | 811 | 990 |
| Esp3 I | cgtctc   1/5 | 966 | 967 | 834 |
| Bpm I | ctggag   16/14 | 969 | 970 | 831 |
| PflM I | ccannnn/ntgg | 971 | 972 | 829 |
| Bsm I | gaatgc   1/-1 | 1049 | 1050 | 751 |
| Alu I | ag/ct | 1063 | 1064 | 737 |
| BceF I | acggc   12/13 | 1151 | 1152 | 649 |
| Bgl II | a/gatct | 1389 | 1390 | 411 |
| BstY I | r/gatcy | 1389 | 1390 | 411 |
| ApaL I | g/tgcac | 1465 | 1466 | 335 |
| Age I | a/ccggt | 1497 | 1498 | 303 |
| BsrF I | r/ccggy | 1497 | 1498 | 303 |
| Nsp I | rcatg/y | 1551 | 1552 | 249 |
| Nsp7524 I | r/catgy | 1551 | 1552 | 249 |
| NspC I | rcatg/y | 1551 | 1552 | 249 |

```
                          10        20        30        40        50        60
                           |         |         |         |         |         |
Contig# 1                            ||
SMBP prot                    AAAALWLLLLLLPRTRA-DEHEHTYQDKE----------------EVV
Arabidobsis prot     MPSSSSAAVLVFLLLVSLLTPTFA-SDSDHKYQAEE----------------QVT
hMP70 prot           MTVVGNPRSWSCQWLPILILLLGTGHGPGVEGVTHYKAGD----------------PVI
p76 prot             MSARLPVLSPPRWPRLLLLSLLLLGAVPGP--RSGAFYLPGLAPVNFCDEEKKSDECKAEIE
d87444 prot                               MCETSAFYVPGVAPINFHQNDP-------VEI
Emp70 prot           MIYKMAHVQLLLLYFFV--------STVKAFYLPGVAPTTYREND--------NIP 70        80        90       100       110       120
                           |         |         |         |         |         |
Contig# 1             ||   |                              |                   |
SMBP prot            LWMNTVGP---YHNRQE--------------TYKYF--SLPFCVGSKKSISHYHETLGEALQ
Arabidobsis prot     LWVNKVGP---YNNPQE--------------TYNYY--SLPFCRPSGNNVHKW-GGLGEVLG
hMP70 prot           LYVNKVGP---YHNPQE--------------TYHYY--QLPVCCPEK--IRHKSLSLGEVLD
p76 prot             LFVNRLDSVES----------------VLPYEYT--AFDFCQASE--GKRPSENLGQVLF
d87444 prot          KAVKLTSSRT-----------------QLPYEYY--SLPFCQPSK--ITYKAENLGEVLR
Emp70 prot           LLVNHLTPSMNYQHKDEDGNNVSGDKENFLYSYDYYYNRFHFCQPEK--VEKQPESLGSVIF 130       140       150       160       170       180
                           |         |         |         |         |         |
Contig# 1             | | |     |         |         |           |  | |     ||
SMBP prot            GVELEFSGLDIKFKDDVMPATYCEIDLDKEKRDA------FVYAIKNHYWYQMYIDDLPIW-
Arabidobsis prot     GNELIDSEIAIKFMKNVERSVICPLELDEAKVKH------FKDAIESSYWFEFFMGMFHVC-
hMP70 prot           GDRMAESLYEIRFRENVEKRILCHMQLSSAQVEQ------LRQAIEELYYFEFVVDDLPIR-
p76 prot             GERIEPSPYKFTFNKKETCKLVCTKTYHTEKAEDKQKLEFLKKSMLLNYQHHWIVDNMPVTW
d87444 prot          GDRIVNTPFQVLMNSEKKCEVLCSQSNKPVTLTVEQS-RLVAERITEDYYVHLIADNLPVAT
Emp70 prot           GDRIYNSPFQLNMLQEKECESLCKTVIPGDDA-------KFINKLIKNGFFQNWLIDGLPAAR 190       200       210       220       230       240
                           |         |         |         |         |         |
Contig# 1                         ---GIVGE--ADE---------------------------------
SMBP prot            ------------------CFVGELHPDK--------------------NSENGKHVLYTH
Arabidobsis prot     ------------------GFVGYMEESG--------------------FLPHSHKIGL
hMP70 prot           CYDVEDGQRFCNPGFPIGCYIT-------------DKGHAKD---ACVISSDFHERDTF-YL
p76 prot             -RLEL-----YSNRD-----SD------------DKKKEKDVQFEHGYRLGFTDVNKI-TL
d87444 prot          EVYDGRTKTSFYGAGFNLGFVQVTQGTDIEATPKGAETTDKDVELETRNDCNMVKTYELPYF
Emp70 prot 250       260       270       280       290       300       310
                           |         |         |         |         |         |         |
Contig# 1            -NGED---YYLWTYKKLEIGFNGNRIVDVNLTSEGKVK----------------------L
SMBP prot            KNIVVK--YNKDQIIHVNLTQDNPRP-------------------------------L
Arabidobsis prot     WTHLDFHLEFHGD-----------RIIFANVSVRDVKPHSLDG------------------L
hMP70 prot           FNHVDIKIYYH----VVETGSMGARLVAAKLEPKSFKHTHI---DKPDCSGPPMDISN----
p76 prot             HNHLSFILYYHRED-MEEDQEHTYRVVRFEVIPQSIRLEDLKADEKSSCTLPEGTNSSPQEI
d87444 prot          ANHFDIMIEYH------DRGEGNYRVVGVIVEPVSIKRSS-----PGTCE----TTGSPLML
Emp70 prot 320       330       340       350       360       370
                           |         |         |         |         |         |
Contig# 1                                                         | | ||   ||  |  |||
SMBP prot            VPNTKIQMS--YSVKWKKSD-VKFEDRFDKYLDPSFFQH--RIHWFSIFNSFMMVIFLVGLV
Arabidobsis prot     EAGKKMDLT--YSVQWIPTN-VTFARRFDVYLDYPFFEH--QIHWFSIFNSFMMVIFLTGLV
hMP70 prot           RPDEFLGLTHTYSVRWSETS-VERRSDRRRGDDGGFFPRTLEIHWLSIINSMVLVFLLVGFV
p76 prot             KASGEIKIAYTYSVSFEEDDKIRWASRWDYILESMPHT---HIQWFSIMNSLVIVLFLSGMV
d87444 prot          DPTKENQLYFTYSVHWEESD-IKWASRWDTYL-TMSDV---QIHWFSIINSVVVVFFLSGIL
Emp70 prot           DEENDNEVYFTYSVKFNESAT-SWATRWDKYLHVY-DP---SIQWFSLINFSLVVVLLSSVV
```

Fig. 22 B

```
                         380       390       400       410       420       430
                          |  |      |         |         |         |         | |
Contig# 1                 || |      |         |         |         |         | ||
SMBP prot                SMILMRTLRKDYARTSKEEE-MDD-MDRDLGD-EYGWKQVHGDVFRPSSHPLIFSSLIGSGC
Arabidobsis prot         SMILMRTLRNDYAKYAREDDDLES-LERDVSE-ESGWKLVHGDVFRPASSLVLLSAVVGTGA
hMP70 prot               AVILMRVLRNDLARYNLDEETTSAGSGDDFDQGDNGWKIIHTDVFRFPPYRGLLCAVLGVGA
p76 prot                 AMIMLRTLHKDIARYNQ------MDSTED-AQEEFGWKLVHGDIFRPPRKGMLLSVFLGSGT
d87444 prot              SMIIIRTLRKDIANYNK------EDDIED-TMEESGWKLVHGDVFRPPQYOMILSSLLGSGI
Emp70 prot               IHSLLRALKSDFARYNE------LNLDDD-FQEDSGWKLNHGDVFRSPSQSLTLSILVGSGV 440       450       460       470       480       490
                          |         |         |         |  ||      |    || |      |
Contig# 1                 | |       |         | |      ||  |       |    || |      |
SMBP prot                QIFAVSLIVIIVAMIEDLYTER-GSMLSTAIFVYAATSPVNGYFGGSLYARQGGRRWIKQMF
Arabidobsis prot         QLALLVLLVILMAIVGTLYVGR-GAIVTTFIVCYALTSFVSGYVSGGMYSRSGGKHWIKCMV
hMP70 prot               QFLALGTGIIVMALLGMFNVRRHGAINSAAILLYALTCCISGYVSSHFYRQIGGERWVWNII
p76 prot                 QILIMTFVTLFFACLGFLSPANRGALMTCAVVLWVLLGTPAGYVAARFYKSFGGEKWKTNVL
d87444 prot              QLFCMILIVIFVAMLGMLSPSSRGALMTTACFLFMFMGVFGGFSAGRLYRTLKGHRWKKGAF
Emp70 prot               QLFLMVTCSIFFAALGFLSPSSRGSLATVMFILYALFGFVGSYTSMGIYKFFNGPYWKANLI 500       510      .520       530       540       550
                          |         |         |  |      |  |      |  |      |
Contig# 1                 | |       |         |  |      |  |      |  |      |
SMBP prot                IGAFLIPAMVCGTAFFINFIAIYYHASRAIPFGTMVAVCCICFFVILPLNLVGTILGRNLSG
Arabidobsis prot         LTASLFPFLCFGIGFLLNTIAIFYGSLAAIPFGTMVVVFVIWGFISFPLALLGTVVGRNWSG
hMP70 prot               LTTSLFSVPFFLTWSVVNSVHWANGSTQALPATTILLLLTVWLLVGFPLTVIGGIFGKNNAS
p76 prot                 LTSFLCPGIVFADFFIMNLILWGEGSSAAIPFGTLVAILALWFCISVPLTFIGAYFGFKK-N
d87444 prot              CTATLYPGVVFGICFVLNCFIWGKHSSGAVPFPTMVALLCMWFGISLPLVYLGYYFGFRK-Q
Emp70 prot               LTPLLVPGAILLIIALNFFLMFVHSSGVIPASTLFFMVFLWFLFSIPSSFAGSLIARKRCH 560       570       580       590       600       610       620
                          |         ||        |         ||||     | ||||||| |        ||| ||
Contig# 1                 | |||     | |       ||        ||       | |        |         ||| ||
SMBP prot                QPNFPCRVNAVPRPIPEKKWFMEPAVIVCLGGILPFGSIFIEMYFIFTSFWAYKIYYVYGFM
Arabidobsis prot         APNNPCRVKTIPRPIPEKKWYLTPSVVSLMGGLLPFGSIFIEMYFVFTSFWNYKVYYVYGFM
hMP70 prot               PFDAPCRTKNIAREINPQPWYKSTDIHMTVGGFLPFSAISVELYYIFATVWGREQYTLYGIL
p76 prot                 AIEHPVRTNQIPRQIPEQSFYTKPLPGIIMGGILPFGCIFIQLFFILNSIWSHQMYYMFGFL
d87444 prot              PYDNPVRTNQIPRQIPEQRWYMNRFVGILMAGILPFGAMFIELFFIFSAIWENQFYYLFGFL
Emp70 prot               WDEHPTKTNQIARQIPFQPWYLKTIPATLIAGIFPFGSIAVELYFIYTSLWFNKIFYMFGFL 630       640       650       660       670       680
                          | | |     |         | |      | | |    ||| || | |    |         |
Contig# 1                 | | |     |         | |      | | |    ||| || | |    |         |
SMBP prot                MLVLVILCIVTVCVTIVCTYFLLNAEDYRWQWTSFLSAAST-AIYVYMYSFYYYFFKTKMYG
Arabidobsis prot         LLVFVILVIVTVCVTIVGTYFLLNAENYHWQWTSFFSAAST-AVYVYLYSIYYYYVKTKMSG
hMP70 prot               FFVFAILLSVGASISIALTYFQLSGEDRWWWRSVLSVGST-GLFIFLYSVFYYARRSNMSG
p76 prot                 FLVFIILVITCSEATILLCYFHLCAEDHWQWRSFLTSGFT-AVYFLIYAVHYFFSKLQITG
d87444 prot              FLVFIILVVSCSQISIVMVYFQLCAEDRWWWRNFLVSGGS-AFYVLVYAIFYFVNKLDIVE
Emp70 prot               FFSFLLLTLTSSLVTILITYHSLCLENWKWQWRGFIIGGAGCALYVFIHSILF--TKFKLGG 690     · 700       710       720
                          |         |    ||  ||||| |     |         |
Contig# 1                 | |       |    ||  ||||| |     |         |
SMBP prot                LFQTSFYFGYMAVFSTALGIMCGAIGYMGTSAFVRKIYTNVKID
Arabidobsis prot         FFQTSFYFGYTMMFCLGLGILCGAVGYLGSNLFVRRIYRNIKCD
hMP70 prot               AVQTVEFFGYSLLTGYVFFLMLGTISFFSSLKFIRYIYVNLKMD
p76 prot                 TASTILYFGYTMIMVLIFFLFTGTIGFFACFWFVTKIYSVVKVD
d87444 prot              FIPSLLYFGYTALMVLSFWLLTGTIGFYAAYMFVRKIYAAVKID
Emp70 prot               FTTIVLYVGYSSVISLLCCLVTGSIGFISSMLFVRKIYSSIKVD
```

Fig. 24 A

```
1                              CC GCC GCG CTG TGG CTG CTG CTG CTG CTG CCC CGG ACC CGG GCG GAC GAG CAC GAA CAC ACG TAT CAA GAT   74
1                                 A   A   L   W   L   L   L   L   L   L   P   R   T   R   A   D   E   H   E   H   T   Y   Q   D   24

75   AAA GAG GAA GTT GTC TTA TGG ATG AAT ACT GTT GGG CCC TAC CAT AAT CGT CAA GAA ACA TAT CCG TAC TTT TCA CTT CCA TTC TGT GTG   164
25    K   E   E   V   V   L   W   M   N   T   V   G   P   Y   H   N   R   Q   E   T   Y   K   Y   F   S   L   P   F   C   V   54

165  GGG TCA AAA AAA AGT ATC AGT CAT TAC CAT GAA ACT CTG GGA GAA GCA CTT CAA GGG GTT GAA TTG GAA TTT AGT GGT CTG GAT ATT AAA   254
55    G   S   K   K   S   I   S   H   Y   H   E   T   L   G   E   A   L   Q   G   V   E   L   E   F   S   G   L   D   I   K   84

255  TTT AAA GAT GAT GTG ATG CCA GCC ACT TAC TGT GAA ATT GAT TTA GAT AAA GAA AAG AGA GAT GCA TTT GTA TAT CCC ATA AAA AAT CAT   344
85    F   K   D   D   V   M   P   A   T   Y   C   E   I   D   L   D   K   E   K   R   D   A   F   V   Y   P   I   K   N   H   114

345  TAC TGG TAC CAG ATG TAC ATA GAT GAT TTA CCA ATA TGG GGT ATT GTT GGT GAG GCT GAT GAA AAT GGA GAA GAT TAC TAT CTT TGG ACC   434
115   Y   W   Y   Q   M   Y   I   D   D   L   P   I   W   G   I   V   G   E   A   D   E   N   G   E   D   Y   Y   L   W   T   144

435  TAT AAA AAA CTT GAA ATA GGT TTT AAT GGA AAT CGA ATT GTT GAT GTT AAT CTA ACT AGT GAA GGA AAG GTG AAA CTG CTT CCA AAT ACT   524
145   Y   K   K   L   E   I   G   F   N   G   N   R   I   V   D   V   N   L   T   S   E   G   K   V   K   L   V   P   N   T   174

525  AAA ATC CAG ATG TCA TAT TCA GTA AAA TGG AAA AAC TCA GAT GTG AAA TTT GAA GAT CGA TTT GAC AAA TAT CTT GAT CCG TCC TTT TTT   614
175   K   I   Q   M   S   Y   S   V   K   W   K   K   S   D   V   K   F   E   D   R   F   D   K   Y   L   D   P   S   F   F   204

615  CAA CAT CGG ATT CAT TGG TTT TCA ATT TTC AAC TCC TTC ATG ATG GTG ATC TTC TTG GTG GGC TTA GTT TCA ATG ATT TTA ATG AGA ACA   704
205   Q   E   R   I   H   W   F   S   I   F   N   S   F   M   M   V   I   F   L   V   G   L   V   S   M   I   L   M   R   T   234

705  TTA AGA AAA GAT TAT GCT CGG TAC AGT AAA GAG GAA GAA ATG GAT GAT ATG GAT AGA GAC CTA GGA GAT GAA TAT GGA TGG AAA CAG GTG   794
235   L   R   K   D   Y   A   R   Y   S   K   E   E   E   M   D   D   M   D   R   D   L   G   D   E   Y   G   W   K   Q   V   264

795  CAT GGA GAT GTA TTT AGA CCA TCA AGT CAC CCA CTG ATA TTT TCC TCT CTG ATT GGT TCT GGA TGT CAG ATA TTT GCT GTG TCT CTC ATC   884
265   H   G   D   V   F   R   P   S   S   H   P   L   I   F   S   S   L   I   G   S   G   C   Q   I   F   A   V   S   L   I   294

885  GTT ATT ATT GTT GCA ATG ATA GAA GAT TTA TAT ACT GAG ACG GGA TCA ATG CTC AGT ACA GCC ATA TTT GTC TAT GCT GCT ACG TCT CCA   974
295   V   I   I   V   A   M   I   E   D   L   Y   T   E   R   G   S   M   L   S   T   A   I   F   V   Y   A   A   T   S   P   324

975  GTG AAT GGT TAT TTT GGA GGA AGT CTG TAT GCT AGA CAA GGA GGA AGG AGA TGG ATA AAG CAG ATG TTT ATT GGG GCA TTC CTT ATC CCA   1064
325   V   N   G   Y   F   G   G   S   L   Y   A   R   Q   G   G   R   R   W   I   K   Q   M   F   I   G   A   F   L   I   P   354

1065 CCT ATG GTG TGT GGC ACT GCC TTC TTC ATC AAT TTC ATA GCC ATT TAT TAC CAT GCT TCA AGA GCC ATT CCT TTT GGA ACA ATG GTG GCC   1154
355   A   M   V   C   G   T   A   F   F   I   N   F   I   A   I   Y   Y   H   A   S   R   A   I   P   F   G   T   M   V   A   384

1155 GTT TGT TGC ATC TGT TTT TTT GTT ATT CTT CCT CTA AAT CTT GTT GGT ACA ATA CTT GGC CGA AAT CTG TCA GGT CAG CCC AAC TTT CCT   1244
385   V   C   C   I   C   F   F   V   I   L   P   L   N   L   V   G   T   I   L   G   R   N   L   S   G   Q   P   N   F   P   414

1245 TGT GGT GTC AAT GCT GTG CCT CGT CCT ATA CCG GAG AAA AAA TGG TTC ATG GAG CCT GCG GTT ATT GTT TGC CTG GGT GGA ATT TTA CCT   1334
415   C   R   V   N   A   V   P   R   P   I   P   E   K   K   W   F   M   E   P   A   V   I   V   C   L   G   G   I   L   P   444

1335 TTT GGT TCA ATC TTT ATT GAA ATG TAT TTC ATC TTC ACG TCT TTC TGG GCA TAT AAG ATC TAT TAT GTC TAT GGC TTC ATG ATG CTG GTG   1424
445   F   G   S   I   F   I   E   M   Y   F   I   F   T   S   F   W   A   Y   K   I   Y   Y   V   Y   G   F   M   M   L   V   474

1425 CTG GTT ATC CTG TGC ATT GTG ACT GTC TGT GTG ACT ATT GTG TGC ACA TAT TTT CTA CTA AAT GCA GAA GAT TAC CGG TGG CAA TGG ACA   1514
475   L   V   I   L   C   I   V   T   V   C   V   T   I   V   C   T   Y   F   L   L   N   A   E   D   Y   R   W   Q   W   T   504

1515 AGT TTT CTC TCT GCT GCA TCA ACT GCA ATC TAT GTT TAC ATG TAT TCC TTT TAC TAC TAT TTT TTC AAA ACA AAG ATG TAT GGC TTA TTT   1604
505   S   F   L   S   A   A   S   T   A   I   Y   V   Y   M   Y   S   F   Y   Y   Y   F   F   K   T   K   M   Y   G   L   F   534

1605 CAA ACA TCA TTT TAC TTT GGA TAT ATG CCG GTA TTT AGC ACA GCC TTG GGG ATA ATG TGT GGA GCG ATT GGT TAC ATG GGA ACA AGT TTT   1694
535   Q   T   S   F   Y   F   G   Y   M   A   V   F   S   T   A   L   G   I   M   C   G   A   I   G   Y   M   G   T   S   A   564

1695 TTT GTC CGA AAA ATC TAT ACT AAT CTG AAA ATT GAC TAG AGACCCAAGAAAACCTGGAACTTTGGATCAATTTCTTTTTCATAGGGGTGGAACTTGCACAGCAAAA   1800
565   F   V   R   K   I   Y   T   N   V   K   I   D   *                                                                         576
```

Fig. 24 B

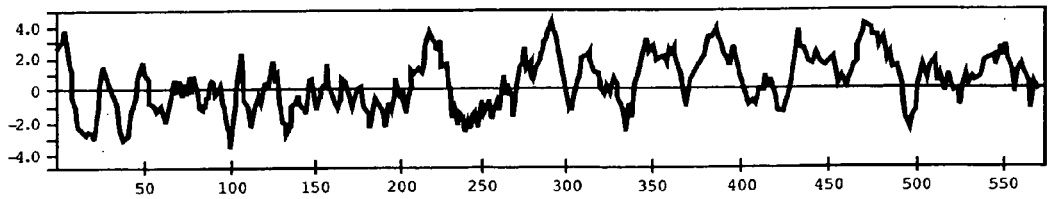

SEQUENCE LISTING

<160> NUMBER OF SEQ ID NOS: 21

<210> SEQ ID NO 1
<211> LENGTH: 439
<212> TYPE: PRT
<213> ORGANISM: Homo sapiens -continued

<400> SEQUENCE: 1

Met Tyr Ile Asp Asp Leu Pro Ile Trp Gly Ile Val Gly Glu Ala Asp
1               5                   10                  15

Glu Asn Gly Glu Asp Tyr Tyr Leu Trp Thr Tyr Lys Lys Leu Glu Ile
            20                  25                  30

Gly Phe Asn Gly Asn Arg Ile Val Asp Val Asn Leu Thr Ser Glu Gly
        35                  40                  45

Lys Val Lys Leu Val Pro Asn Thr Lys Ile Gln Met Ser Tyr Ser Val
    50                  55                  60

Lys Trp Lys Lys Ser Asp Val Lys Phe Glu Asp Arg Phe Asp Lys Tyr
65                  70                  75                  80

Leu Asp Pro Ser Phe Phe Gln His Arg Ile His Trp Phe Ser Ile Phe
                85                  90                  95

Asn Ser Phe Met Met Val Ile Phe Leu Val Gly Leu Val Ser Met Ile
            100                 105                 110

Leu Met Arg Thr Leu Arg Lys Asp Tyr Ala Arg Tyr Ser Lys Glu Glu
        115                 120                 125

Glu Met Asp Asp Met Asp Arg Asp Leu Gly Asp Glu Tyr Gly Trp Lys
130                 135                 140

Gln Val His Gly Asp Val Phe Arg Pro Ser Ser His Pro Leu Ile Phe
145                 150                 155                 160

Ser Ser Leu Ile Gly Ser Gly Cys Gln Ile Phe Ala Val Ser Leu Ile
                165                 170                 175

Val Ile Ile Val Ala Met Ile Glu Asp Leu Tyr Thr Glu Arg Gly Ser
            180                 185                 190

Met Leu Ser Thr Ala Ile Phe Val Tyr Ala Ala Thr Ser Pro Val Asn
        195                 200                 205

Gly Tyr Phe Gly Gly Ser Leu Tyr Ala Arg Gln Gly Arg Arg Trp
    210                 215                 220

Ile Lys Gln Met Phe Ile Gly Ala Phe Leu Ile Pro Ala Met Val Cys
225                 230                 235                 240

Gly Thr Ala Phe Phe Ile Asn Phe Ile Ala Ile Tyr Tyr His Ala Ser
                245                 250                 255

Arg Ala Ile Pro Phe Gly Thr Met Val Ala Val Cys Cys Ile Cys Phe
            260                 265                 270

Phe Val Ile Leu Pro Leu Asn Leu Val Gly Thr Ile Leu Gly Arg Asn
        275                 280                 285

Leu Ser Gly Gln Pro Asn Phe Pro Cys Arg Val Asn Ala Val Pro Arg
    290                 295                 300

Pro Ile Pro Glu Lys Lys Trp Phe Met Glu Pro Ala Val Ile Val Cys
305                 310                 315                 320

Leu Gly Gly Ile Leu Pro Phe Gly Ser Ile Phe Ile Glu Met Tyr Phe
                325                 330                 335

Ile Phe Thr Ser Phe Trp Ala Tyr Lys Ile Tyr Val Tyr Gly Phe
            340                 345                 350

Met Met Leu Val Leu Val Ile Leu Cys Ile Val Thr Val Cys Val Thr
        355                 360                 365

Ile Val Cys Thr Tyr Phe Leu Leu Asn Ala Glu Asp Tyr Arg Trp Gln
    370                 375                 380

Trp Thr Ser Phe Leu Ser Ala Ala Ser Thr Ala Ile Tyr Val Tyr Met
385                 390                 395                 400

Tyr Ser Phe Tyr Tyr Phe Phe Lys Thr Lys Met Tyr Gly Leu Phe
                405                 410                 415

Gln Thr Ser Phe Tyr Phe Gly Tyr Met Ala Val Phe Ser Thr Ala Leu
        420                 425                 430

Gly Ile Met Cys Gly Ala Ile
        435

<210> SEQ ID NO 2
<211> LENGTH: 1317
<212> TYPE: DNA
<213> ORGANISM: Homo sapiens

<400> SEQUENCE: 2

| | |
|---|---|
| atgtacatag atgatttacc aatatggggt attgttggtg aggctgatga aaatggagaa | 60 |
| gattactatc tttggaccta taaaaaactt gaaataggtt ttaatggaaa tcgaattgtt | 120 |
| gatgttaatc taactagtga aggaaaggtg aaactggttc aaatactaa atccagatg | 180 |
| tcatattcag taaatggaaa aaagtcagat gtgaaatttg aagatcgatt tgacaaatat | 240 |
| cttgatccgt cctttttca acatcggatt cattggtttt caattttcaa ctccttcatg | 300 |
| atggtgatct tcttggtggg cttagtttca atgattttaa tgagaacatt aagaaaagat | 360 |
| tatgctcggt acagtaaaga ggaagaaatg gatgatatgg atagagacct aggagatgaa | 420 |
| tatggatgga acaggtgca tggagatgta tttagaccat caagtcaccc actgatattt | 480 |
| tcctctctga ttggttctgg atgtcagata tttgctgtgt ctctcatcgt tattattgtt | 540 |
| gcaatgatag aagatttata tactgagagg ggatcaatgc tcagtacagc catatttgtc | 600 |
| tatgctgcta cgtctccagt gaatggttat tttggaggaa gtctgtatgc tagacaagga | 660 |
| ggaaggagat ggataaagca gatgtttatt ggggcattcc ttatcccagc tatggtgtgt | 720 |
| ggcactgcct tcttcatcaa tttcatagcc atttattacc atgcttcaag agccattcct | 780 |
| tttggaacaa tggtggccgt tgttgcatc tgttttttg ttattcttcc tctaaatctt | 840 |
| gttggtacaa tacttggccg aaatctgtca ggtcagccca actttccttg tcgtgtcaat | 900 |
| gctgtgcctc gtcctatacc ggagaaaaaa tggttcatgg agcctgcggt tattgtttgc | 960 |
| ctgggtggaa ttttaccttt tggttcaatc tttattgaaa tgtatttcat cttcacgtct | 1020 |
| ttctgggcat ataagatcta ttatgtctat ggcttcatga tgctggtgct ggttatcctg | 1080 |
| tgcattgtga ctgtctgtgt gactattgtg tgcacatatt ttctactaaa tgcagaagat | 1140 |
| taccggtggc aatggacaag ttttctctct gctgcatcaa ctgcaatcta tgtttacatg | 1200 |
| tattcctttt actactattt tttcaaaaca aagatgtatg gcttatttca aacatcattt | 1260 |
| tactttggat atatggcggt atttagcaca gccttgggga taatgtgtgg agcgatt | 1317 |

<210> SEQ ID NO 3
<211> LENGTH: 965
<212> TYPE: DNA
<213> ORGANISM: Homo sapiens

<400> SEQUENCE: 3

| | |
|---|---|
| cagatgtcat attcagtaaa atggaaaaag tcagatgtga aatttgaaga tcgatttgac | 60 |
| aaatatcttg atccgtcctt ttttcaacat cggattcatt ggttttcaat tttcaactcc | 120 |
| ttcatgatgg tgatcttctt ggtgggctta gtttcaatga ttttaatgag aacattaaga | 180 |
| aaagattatg ctcggtacag taaagaggaa gaaatggatg atatggatag agacctagga | 240 |
| gatgaatatg gatggaaaca ggtgcatgga gatgtatttta gaccatcaag tcacccactg | 300 |
| atattttcct ctctgattgg ttctggatgt cagatatttg ctgtgtctct catcgttatt | 360 |

-continued

```
attgttgcaa tgatagaaga tttatatact gagaggggat caatgctcag tacagccata      420
tttgtctatg ctgctacgtc tccagtgaat ggttatttta gaggaagtct gtatgctaga      480
caaggaggaa ggagatggat aaagcagatg tttattgggg cattccttat cccagctatg      540
gtgtgtggca ctgccttctt catcaatttc atagccattt attaccatgc ttcaagagcc      600
attccttttg gaacaatggt ggccgtttgt tgcatctgtt tttttgttat tcttcctcta      660
aatcttgttg gtacaatact tggccgaaat ctgtcaggtc agcccaactt tccttgtcgt      720
gtcaatgctg tgcctcgtcc tataccggag aaaaaatggt tcatggagcc tgcggttatt      780
gtttgcctgg gtgaatttt acctttggt tcaatcttta ttgaaatgta tttcatcttc       840
acgtctttct gggcatataa gatctattat gtctatggct tcatgatgct ggtgctggtt      900
atcctgtgca ttgtgactgt ctgtgtgact attgtgtgca catattttct actaaatgca      960
gaaga                                                                   965
```

<210> SEQ ID NO 4
<211> LENGTH: 285
<212> TYPE: DNA
<213> ORGANISM: Homo sapiens

<400> SEQUENCE: 4

```
tcagtaaaat ggaaaaagtc agatgtgaaa tttgaagatc gatttgacaa atatcttgat       60
ccgtcctttt ttcaacatcg gattcattgg ttttcaattt tcaactcctt catgatggtg      120
atcttcttgg tgggcttagt ttcaatgatt ttaatgagaa cattaagaaa agattatgct      180
cggtacagta agaggaaga atggatgat atggatagag acctaggaga tgaatatgga        240
tggaaacagg tgcatggaga tgtatttaga ccatcaagtc accca                      285
```

<210> SEQ ID NO 5
<211> LENGTH: 17
<212> TYPE: PRT
<213> ORGANISM: Artificial sequence
<220> FEATURE:
<223> OTHER INFORMATION: Fragment generated by acidic cleavage of
      polypeptide able to bind ICYP

<400> SEQUENCE: 5

Asp Pro Ser Phe Phe Gln His Arg Ile His Trp Phe Ser Ile Phe Asn
1               5                   10                  15

Ser

<210> SEQ ID NO 6
<211> LENGTH: 17
<212> TYPE: PRT
<213> ORGANISM: Artificial sequence
<220> FEATURE:
<223> OTHER INFORMATION: Fragment generated by acidic cleavage of
      polypeptide able to bind ICYP
<220> FEATURE:
<221> NAME/KEY: MISC_FEATURE
<222> LOCATION: (3)..(3)
<223> OTHER INFORMATION: Xaa can by any amino acid

<400> SEQUENCE: 6

Asp Pro Xaa Phe Phe Gln His Arg Ile His Val Phe Ser Ile Phe Asn
1               5                   10                  15

His

<210> SEQ ID NO 7
<211> LENGTH: 20

```
<212> TYPE: DNA
<213> ORGANISM: Artificial sequence
<220> FEATURE:
<223> OTHER INFORMATION: probe/primer

<400> SEQUENCE: 7
tcagtaaaat ggaaaaagtc                                            20

<210> SEQ ID NO 8
<211> LENGTH: 20
<212> TYPE: DNA
<213> ORGANISM: Artificial sequence
<220> FEATURE:
<223> OTHER INFORMATION: probe/primer

<400> SEQUENCE: 8
tgggtgactt gatggtctaa                                            20

<210> SEQ ID NO 9
<211> LENGTH: 19
<212> TYPE: DNA
<213> ORGANISM: Artificial sequence
<220> FEATURE:
<223> OTHER INFORMATION: probe/primer

<400> SEQUENCE: 9
gctgtgtctc tcatcgtta                                             19

<210> SEQ ID NO 10
<211> LENGTH: 20
<212> TYPE: DNA
<213> ORGANISM: Artificial sequence
<220> FEATURE:
<223> OTHER INFORMATION: probe/primer

<400> SEQUENCE: 10
ccatccatat tcatctccta                                            20

<210> SEQ ID NO 11
<211> LENGTH: 21
<212> TYPE: DNA
<213> ORGANISM: Artificial sequence
<220> FEATURE:
<223> OTHER INFORMATION: probe/primer

<400> SEQUENCE: 11
cggtatagga cgaggcacag c                                          21

<210> SEQ ID NO 12
<211> LENGTH: 18
<212> TYPE: DNA
<213> ORGANISM: Artificial sequence
<220> FEATURE:
<223> OTHER INFORMATION: probe/primer

<400> SEQUENCE: 12
actgaatatg acatctgg                                              18

<210> SEQ ID NO 13
<211> LENGTH: 1800
<212> TYPE: DNA
<213> ORGANISM: Homo sapiens
<220> FEATURE:
<221> NAME/KEY: CDS
<222> LOCATION: (3)..(1730)
<223> OTHER INFORMATION:
```

<400> SEQUENCE: 13

| | |
|---|---|
| cc gcc gcg ctg tgg ctg ctg ctg ctg ctg ccc cgg acc cgg gcg<br>   Ala Ala Leu Trp Leu Leu Leu Leu Leu Pro Arg Thr Arg Ala<br>    1              5                     10                15 | 47 |
| gac gag cac gaa cac acg tat caa gat aaa gag gaa gtt gtc tta tgg<br>Asp Glu His Glu His Thr Tyr Gln Asp Lys Glu Glu Val Val Leu Trp<br>                  20                     25                    30 | 95 |
| atg aat act gtt ggg ccc tac cat aat cgt caa gaa aca tat aag tac<br>Met Asn Thr Val Gly Pro Tyr His Asn Arg Gln Glu Thr Tyr Lys Tyr<br>         35                     40                     45 | 143 |
| ttt tca ctt cca ttc tgt gtg ggg tca aaa aaa agt atc agt cat tac<br>Phe Ser Leu Pro Phe Cys Val Gly Ser Lys Lys Ser Ile Ser His Tyr<br>     50                     55                     60 | 191 |
| cat gaa act ctg gga gaa gca ctt caa ggg gtt gaa ttg gaa ttt agt<br>His Glu Thr Leu Gly Glu Ala Leu Gln Gly Val Glu Leu Glu Phe Ser<br> 65                    70                    75 | 239 |
| ggt ctg gat att aaa ttt aaa gat gat gtg atg cca gcc act tac tgt<br>Gly Leu Asp Ile Lys Phe Lys Asp Asp Val Met Pro Ala Thr Tyr Cys<br>80                     85                     90               95 | 287 |
| gaa att gat tta gat aaa gaa aag aga gat gca ttt gta tat gcc ata<br>Glu Ile Asp Leu Asp Lys Glu Lys Arg Asp Ala Phe Val Tyr Ala Ile<br>                  100                  105               110 | 335 |
| aaa aat cat tac tgg tac cag atg tac ata gat gat tta cca ata tgg<br>Lys Asn His Tyr Trp Tyr Gln Met Tyr Ile Asp Asp Leu Pro Ile Trp<br>          115                  120                125 | 383 |
| ggt att gtt ggt gag gct gat gaa aat gga gaa gat tac tat ctt tgg<br>Gly Ile Val Gly Glu Ala Asp Glu Asn Gly Glu Asp Tyr Tyr Leu Trp<br>         130                   135                140 | 431 |
| acc tat aaa aaa ctt gaa ata ggt ttt aat gga aat cga att gtt gat<br>Thr Tyr Lys Lys Leu Glu Ile Gly Phe Asn Gly Asn Arg Ile Val Asp<br>     145                  150                155 | 479 |
| gtt aat cta act agt gaa gga aag gtg aaa ctg gtt cca aat act aaa<br>Val Asn Leu Thr Ser Glu Gly Lys Val Lys Leu Val Pro Asn Thr Lys<br>160                    165                  170              175 | 527 |
| atc cag atg tca tat tca gta aaa tgg aaa aag tca gat gtg aaa ttt<br>Ile Gln Met Ser Tyr Ser Val Lys Trp Lys Lys Ser Asp Val Lys Phe<br>                  180                  185               190 | 575 |
| gaa gat cga ttt gac aaa tat ctt gat ccg tcc ttt ttt caa cat cgg<br>Glu Asp Arg Phe Asp Lys Tyr Leu Asp Pro Ser Phe Phe Gln His Arg<br>         195                   200                205 | 623 |
| att cat tgg ttt tca att ttc aac tcc ttc atg atg gtg atc ttc ttg<br>Ile His Trp Phe Ser Ile Phe Asn Ser Phe Met Met Val Ile Phe Leu<br>     210                  215                220 | 671 |
| gtg ggc tta gtt tca atg att tta atg aga aca tta aga aaa gat tat<br>Val Gly Leu Val Ser Met Ile Leu Met Arg Thr Leu Arg Lys Asp Tyr<br>225                    230                  235 | 719 |
| gct cgg tac agt aaa gag gaa gaa atg gat gat atg gat aga gac cta<br>Ala Arg Tyr Ser Lys Glu Glu Glu Met Asp Asp Met Asp Arg Asp Leu<br>240                    245                  250              255 | 767 |
| gga gat gaa tat gga tgg aaa cag gtg cat gga gat gta ttt aga cca<br>Gly Asp Glu Tyr Gly Trp Lys Gln Val His Gly Asp Val Phe Arg Pro<br>         260                   265                270 | 815 |
| tca agt cac cca ctg ata ttt tcc tct ctg att ggt tct gga tgt cag<br>Ser Ser His Pro Leu Ile Phe Ser Ser Leu Ile Gly Ser Gly Cys Gln<br>          275                  280                285 | 863 |
| ata ttt gct gtg tct ctc atc gtt att att gtt gca atg ata gaa gat<br>Ile Phe Ala Val Ser Leu Ile Val Ile Ile Val Ala Met Ile Glu Asp<br>         290                   295                300 | 911 |
| tta tat act gag agg gga tca atg ctc agt aca gcc ata ttt gtc tat | 959 |

```
Leu Tyr Thr Glu Arg Gly Ser Met Leu Ser Thr Ala Ile Phe Val Tyr
    305                 310                 315 gct gct acg tct cca gtg aat ggt tat ttt gga gga agt ctg tat gct      1007
Ala Ala Thr Ser Pro Val Asn Gly Tyr Phe Gly Gly Ser Leu Tyr Ala
320                 325                 330                 335 aga caa gga gga agg aga tgg ata aag cag atg ttt att ggg gca ttc      1055
Arg Gln Gly Gly Arg Arg Trp Ile Lys Gln Met Phe Ile Gly Ala Phe
            340                 345                 350 ctt atc cca gct atg gtg tgt ggc act gcc ttc ttc atc aat ttc ata      1103
Leu Ile Pro Ala Met Val Cys Gly Thr Ala Phe Phe Ile Asn Phe Ile
        355                 360                 365 gcc att tat tac cat gct tca aga gcc att cct ttt gga aca atg gtg      1151
Ala Ile Tyr Tyr His Ala Ser Arg Ala Ile Pro Phe Gly Thr Met Val
    370                 375                 380 gcc gtt tgt tgc atc tgt ttt ttt gtt att ctt cct cta aat ctt gtt      1199
Ala Val Cys Cys Ile Cys Phe Phe Val Ile Leu Pro Leu Asn Leu Val
385                 390                 395 ggt aca ata ctt ggc cga aat ctg tca ggt cag ccc aac ttt cct tgt      1247
Gly Thr Ile Leu Gly Arg Asn Leu Ser Gly Gln Pro Asn Phe Pro Cys
400                 405                 410                 415 cgt gtc aat gct gtg cct cgt cct ata ccg gag aaa aaa tgg ttc atg      1295
Arg Val Asn Ala Val Pro Arg Pro Ile Pro Glu Lys Lys Trp Phe Met
            420                 425                 430 gag cct gcg gtt att gtt tgc ctg ggt gga att tta cct ttt ggt tca      1343
Glu Pro Ala Val Ile Val Cys Leu Gly Gly Ile Leu Pro Phe Gly Ser
        435                 440                 445 atc ttt att gaa atg tat ttc atc ttc acg tct ttc tgg gca tat aag      1391
Ile Phe Ile Glu Met Tyr Phe Ile Phe Thr Ser Phe Trp Ala Tyr Lys
    450                 455                 460 atc tat tat gtc tat ggc ttc atg atg ctg gtg ctg gtt atc ctg tgc      1439
Ile Tyr Tyr Val Tyr Gly Phe Met Met Leu Val Leu Val Ile Leu Cys
465                 470                 475 att gtg act gtc tgt gtg act att gtg tgc aca tat ttt cta cta aat      1487
Ile Val Thr Val Cys Val Thr Ile Val Cys Thr Tyr Phe Leu Leu Asn
480                 485                 490                 495 gca gaa gat tac cgg tgg caa tgg aca agt ttt ctc tct gct gca tca      1535
Ala Glu Asp Tyr Arg Trp Gln Trp Thr Ser Phe Leu Ser Ala Ala Ser
            500                 505                 510 act gca atc tat gtt tac atg tat tcc ttt tac tac tat ttt ttc aaa      1583
Thr Ala Ile Tyr Val Tyr Met Tyr Ser Phe Tyr Tyr Tyr Phe Phe Lys
        515                 520                 525 aca aag atg tat ggc tta ttt caa aca tca ttt tac ttt gga tat atg      1631
Thr Lys Met Tyr Gly Leu Phe Gln Thr Ser Phe Tyr Phe Gly Tyr Met
    530                 535                 540 gcg gta ttt agc aca gcc ttg ggg ata atg tgt gga gcg att ggt tac      1679
Ala Val Phe Ser Thr Ala Leu Gly Ile Met Cys Gly Ala Ile Gly Tyr
545                 550                 555 atg gga aca agt gcc ttt gtc cga aaa atc tat act aat gtg aaa att      1727
Met Gly Thr Ser Ala Phe Val Arg Lys Ile Tyr Thr Asn Val Lys Ile
560                 565                 570                 575 gac tagagaccca agaaacctg gaactttgga tcaatttctt tttcataggg            1780
Asp gtggaacttg cacagcaaaa                                                1800

<210> SEQ ID NO 14
<211> LENGTH: 576
<212> TYPE: PRT
<213> ORGANISM: Homo sapiens

<400> SEQUENCE: 14
```

-continued

```
Ala Ala Leu Trp Leu Leu Leu Leu Leu Pro Arg Thr Arg Ala Asp
 1               5                  10                 15

Glu His Glu His Thr Tyr Gln Asp Lys Glu Val Val Leu Trp Met
                20                  25                 30

Asn Thr Val Gly Pro Tyr His Asn Arg Gln Glu Thr Tyr Lys Tyr Phe
                35                  40                 45

Ser Leu Pro Phe Cys Val Gly Ser Lys Lys Ser Ile Ser His Tyr His
 50                  55                  60

Glu Thr Leu Gly Glu Ala Leu Gln Gly Val Glu Leu Glu Phe Ser Gly
 65                  70                  75                 80

Leu Asp Ile Lys Phe Lys Asp Val Met Pro Ala Thr Tyr Cys Glu
                85                  90                 95

Ile Asp Leu Asp Lys Glu Lys Arg Asp Ala Phe Val Tyr Ala Ile Lys
                100                 105                110

Asn His Tyr Trp Tyr Gln Met Tyr Ile Asp Asp Leu Pro Ile Trp Gly
                115                 120                125

Ile Val Gly Glu Ala Asp Glu Asn Gly Glu Asp Tyr Tyr Leu Trp Thr
 130                 135                 140

Tyr Lys Lys Leu Glu Ile Gly Phe Asn Gly Asn Arg Ile Val Asp Val
145                 150                 155                160

Asn Leu Thr Ser Glu Gly Lys Val Lys Leu Val Pro Asn Thr Lys Ile
                165                 170                 175

Gln Met Ser Tyr Ser Val Lys Trp Lys Lys Ser Asp Val Lys Phe Glu
                180                 185                 190

Asp Arg Phe Asp Lys Tyr Leu Asp Pro Ser Phe Phe Gln His Arg Ile
                195                 200                 205

His Trp Phe Ser Ile Phe Asn Ser Phe Met Met Val Ile Phe Leu Val
                210                 215                 220

Gly Leu Val Ser Met Ile Leu Met Arg Thr Leu Arg Lys Asp Tyr Ala
225                 230                 235                240

Arg Tyr Ser Lys Glu Glu Met Asp Asp Met Asp Arg Asp Leu Gly
                245                 250                 255

Asp Glu Tyr Gly Trp Lys Gln Val His Gly Asp Val Phe Arg Pro Ser
                260                 265                 270

Ser His Pro Leu Ile Phe Ser Ser Leu Ile Gly Ser Gly Cys Gln Ile
                275                 280                 285

Phe Ala Val Ser Leu Ile Val Ile Ile Val Ala Met Ile Glu Asp Leu
                290                 295                 300

Tyr Thr Glu Arg Gly Ser Met Leu Ser Thr Ala Ile Phe Val Tyr Ala
305                 310                 315                320

Ala Thr Ser Pro Val Asn Gly Tyr Phe Gly Gly Ser Leu Tyr Ala Arg
                325                 330                 335

Gln Gly Gly Arg Arg Trp Ile Lys Gln Met Phe Ile Gly Ala Phe Leu
                340                 345                 350

Ile Pro Ala Met Val Cys Gly Thr Ala Phe Phe Ile Asn Phe Ile Ala
                355                 360                 365

Ile Tyr Tyr His Ala Ser Arg Ala Ile Pro Phe Gly Thr Met Val Ala
                370                 375                 380

Val Cys Cys Ile Cys Phe Phe Val Ile Leu Pro Leu Asn Leu Val Gly
385                 390                 395                400

Thr Ile Leu Gly Arg Asn Leu Ser Gly Gln Pro Asn Phe Pro Cys Arg
                405                 410                 415
```

```
Val Asn Ala Val Pro Arg Pro Ile Pro Glu Lys Lys Trp Phe Met Glu
            420                 425                 430
Pro Ala Val Ile Val Cys Leu Gly Gly Ile Leu Pro Phe Gly Ser Ile
            435                 440                 445
Phe Ile Glu Met Tyr Phe Ile Phe Thr Ser Phe Trp Ala Tyr Lys Ile
            450                 455                 460
Tyr Tyr Val Tyr Gly Phe Met Met Leu Val Leu Val Ile Leu Cys Ile
465                 470                 475                 480
Val Thr Val Cys Val Thr Ile Val Cys Thr Tyr Phe Leu Leu Asn Ala
            485                 490                 495
Glu Asp Tyr Arg Trp Gln Trp Thr Ser Phe Leu Ser Ala Ala Ser Thr
            500                 505                 510
Ala Ile Tyr Val Tyr Met Tyr Ser Phe Tyr Tyr Phe Phe Lys Thr
            515                 520                 525
Lys Met Tyr Gly Leu Phe Gln Thr Ser Phe Tyr Phe Gly Tyr Met Ala
            530                 535                 540
Val Phe Ser Thr Ala Leu Gly Ile Met Cys Gly Ala Ile Gly Tyr Met
545                 550                 555                 560
Gly Thr Ser Ala Phe Val Arg Lys Ile Tyr Thr Asn Val Lys Ile Asp
            565                 570                 575
```

<210> SEQ ID NO 15
<211> LENGTH: 578
<212> TYPE: PRT
<213> ORGANISM: Homo sapiens
<220> FEATURE:
<221> NAME/KEY: MISC_FEATURE
<223> OTHER INFORMATION: SM binding protein

<400> SEQUENCE: 15

```
Ala Ala Ala Ala Leu Trp Leu Leu Leu Leu Leu Pro Arg Thr Arg
1               5                   10                  15
Ala Asp Glu His Glu His Thr Tyr Gln Asp Lys Glu Glu Val Val Leu
            20                  25                  30
Trp Met Asn Thr Val Gly Pro Tyr His Asn Arg Gln Glu Thr Tyr Lys
            35                  40                  45
Tyr Phe Ser Leu Pro Phe Cys Val Gly Ser Lys Lys Ser Ile Ser His
50                  55                  60
Tyr His Glu Thr Leu Gly Glu Ala Leu Gln Gly Val Glu Leu Glu Phe
65                  70                  75                  80
Ser Gly Leu Asp Ile Lys Phe Lys Asp Asp Val Met Pro Ala Thr Tyr
            85                  90                  95
Cys Glu Ile Asp Leu Asp Lys Glu Lys Arg Asp Ala Phe Val Tyr Ala
            100                 105                 110
Ile Lys Asn His Tyr Trp Tyr Gln Met Tyr Ile Asp Asp Leu Pro Ile
            115                 120                 125
Trp Gly Ile Val Gly Glu Ala Asp Glu Asn Gly Glu Asp Tyr Tyr Leu
            130                 135                 140
Trp Thr Tyr Lys Lys Leu Glu Ile Gly Phe Asn Gly Asn Arg Ile Val
145                 150                 155                 160
Asp Val Asn Leu Thr Ser Glu Gly Lys Val Lys Leu Val Pro Asn Thr
            165                 170                 175
Lys Ile Gln Met Ser Tyr Ser Val Lys Trp Lys Lys Ser Asp Val Lys
            180                 185                 190
Phe Glu Asp Arg Phe Asp Lys Tyr Leu Asp Pro Ser Phe Phe Gln His
            195                 200                 205
```

-continued

```
Arg Ile His Trp Phe Ser Ile Phe Asn Ser Phe Met Met Val Ile Phe
    210                 215                 220
Leu Val Gly Leu Val Ser Met Ile Leu Met Arg Thr Leu Arg Lys Asp
225                 230                 235                 240
Tyr Ala Arg Tyr Ser Lys Glu Glu Met Asp Asp Met Asp Arg Asp
                245                 250                 255
Leu Gly Asp Glu Tyr Gly Trp Lys Gln Val His Gly Asp Val Phe Arg
            260                 265                 270
Pro Ser Ser His Pro Leu Ile Phe Ser Ser Leu Ile Gly Ser Gly Cys
        275                 280                 285
Gln Ile Phe Ala Val Ser Leu Ile Val Ile Val Ala Met Ile Glu
    290                 295                 300
Asp Leu Tyr Thr Glu Arg Gly Ser Met Leu Ser Thr Ala Ile Phe Val
305                 310                 315                 320
Tyr Ala Ala Thr Ser Pro Val Asn Gly Tyr Phe Gly Gly Ser Leu Tyr
                325                 330                 335
Ala Arg Gln Gly Gly Arg Arg Trp Ile Lys Gln Met Phe Ile Gly Ala
            340                 345                 350
Phe Leu Ile Pro Ala Met Val Cys Gly Thr Ala Phe Phe Ile Asn Phe
        355                 360                 365
Ile Ala Ile Tyr Tyr His Ala Ser Arg Ala Ile Pro Phe Gly Thr Met
    370                 375                 380
Val Ala Val Cys Cys Ile Cys Phe Phe Val Ile Leu Pro Leu Asn Leu
385                 390                 395                 400
Val Gly Thr Ile Leu Gly Arg Asn Leu Ser Gly Gln Pro Asn Phe Pro
                405                 410                 415
Cys Arg Val Asn Ala Val Pro Arg Pro Ile Pro Glu Lys Lys Trp Phe
            420                 425                 430
Met Glu Pro Ala Val Ile Val Cys Leu Gly Gly Ile Leu Pro Phe Gly
        435                 440                 445
Ser Ile Phe Ile Glu Met Tyr Phe Ile Phe Thr Ser Phe Trp Ala Tyr
    450                 455                 460
Lys Ile Tyr Tyr Val Tyr Gly Phe Met Met Leu Val Leu Val Ile Leu
465                 470                 475                 480
Cys Ile Val Thr Val Cys Val Thr Ile Val Cys Thr Tyr Phe Leu Leu
                485                 490                 495
Asn Ala Glu Asp Tyr Arg Trp Gln Trp Thr Ser Phe Leu Ser Ala Ala
            500                 505                 510
Ser Thr Ala Ile Tyr Val Tyr Met Tyr Ser Phe Tyr Tyr Phe Phe
    515                 520                 525
Lys Thr Lys Met Tyr Gly Leu Phe Gln Thr Ser Phe Tyr Phe Gly Tyr
530                 535                 540
Met Ala Val Phe Ser Thr Ala Leu Gly Ile Met Cys Gly Ala Ile Gly
545                 550                 555                 560
Tyr Met Gly Thr Ser Ala Phe Val Arg Lys Ile Tyr Thr Asn Val Lys
                565                 570                 575
Ile Asp
```

<210> SEQ ID NO 16
<211> LENGTH: 589
<212> TYPE: PRT
<213> ORGANISM: Arabidopsis thaliana
<220> FEATURE:
<221> NAME/KEY: misc_feature
<223> OTHER INFORMATION: endomembrane protein 70

<400> SEQUENCE: 16

```
Met Pro Ser Ser Ser Ala Ala Val Leu Val Phe Leu Leu Leu Val
1               5                   10                  15

Ser Leu Leu Thr Pro Thr Phe Ala Ser Asp Ser Asp His Lys Tyr Gln
            20                  25                  30

Ala Glu Glu Gln Val Thr Leu Trp Val Asn Lys Val Gly Pro Tyr Asn
        35                  40                  45

Asn Pro Gln Glu Thr Tyr Asn Tyr Tyr Ser Leu Pro Phe Cys Arg Pro
    50                  55                  60

Ser Gly Asn Asn Val His Lys Trp Gly Gly Leu Gly Glu Val Leu Gly
65              70                  75                  80

Gly Asn Glu Leu Ile Asp Ser Glu Ile Ala Ile Lys Phe Met Lys Asn
                85                  90                  95

Val Glu Arg Ser Val Ile Cys Pro Leu Glu Leu Asp Glu Ala Lys Val
            100                 105                 110

Lys His Phe Lys Asp Ala Ile Glu Ser Ser Tyr Trp Phe Glu Phe Phe
        115                 120                 125

Met Gly Met Phe His Val Cys Cys Phe Val Gly Glu Leu His Pro Asp
    130                 135                 140

Lys Asn Ser Glu Asn Gly Lys His Val Leu Tyr Thr His Lys Asn Ile
145                 150                 155                 160

Val Val Lys Tyr Asn Lys Asp Gln Ile Ile His Val Asn Leu Thr Gln
                165                 170                 175

Asp Asn Pro Arg Pro Leu Glu Ala Gly Lys Lys Met Asp Leu Thr Tyr
            180                 185                 190

Ser Val Gln Trp Ile Pro Thr Asn Val Thr Phe Ala Arg Arg Phe Asp
        195                 200                 205

Val Tyr Leu Asp Tyr Pro Phe Phe Glu His Gln Ile His Trp Phe Ser
    210                 215                 220

Ile Phe Asn Ser Phe Met Met Val Ile Phe Leu Thr Gly Leu Val Ser
225                 230                 235                 240

Met Ile Leu Met Arg Thr Leu Arg Asn Asp Tyr Ala Lys Tyr Ala Arg
                245                 250                 255

Glu Asp Asp Asp Leu Glu Ser Leu Glu Arg Asp Val Ser Glu Ser
            260                 265                 270

Gly Trp Lys Leu Val His Gly Asp Val Phe Arg Pro Ala Ser Ser Leu
        275                 280                 285

Val Leu Leu Ser Ala Val Val Gly Thr Gly Ala Gln Leu Ala Leu Leu
    290                 295                 300

Val Leu Leu Val Ile Leu Met Ala Ile Val Gly Thr Leu Tyr Val Gly
305                 310                 315                 320

Arg Gly Ala Ile Val Thr Thr Phe Ile Val Cys Tyr Ala Leu Thr Ser
                325                 330                 335

Phe Val Ser Gly Tyr Val Ser Gly Met Tyr Ser Arg Ser Gly Gly
            340                 345                 350

Lys His Trp Ile Lys Cys Met Val Leu Thr Ala Ser Leu Phe Pro Phe
        355                 360                 365

Leu Cys Phe Gly Ile Gly Phe Leu Leu Asn Thr Ile Ala Ile Phe Tyr
    370                 375                 380

Gly Ser Leu Ala Ala Ile Pro Phe Gly Thr Met Val Val Val Phe Val
385                 390                 395                 400
```

```
Ile Trp Gly Phe Ile Ser Phe Pro Leu Ala Leu Leu Gly Thr Val Val
                405                 410                 415

Gly Arg Asn Trp Ser Gly Ala Pro Asn Asn Pro Cys Arg Val Lys Thr
            420                 425                 430

Ile Pro Arg Pro Ile Pro Glu Lys Lys Trp Tyr Leu Thr Pro Ser Val
        435                 440                 445

Val Ser Leu Met Gly Gly Leu Leu Pro Phe Gly Ser Ile Phe Ile Glu
    450                 455                 460

Met Tyr Phe Val Phe Thr Ser Phe Trp Asn Tyr Lys Val Tyr Tyr Val
465                 470                 475                 480

Tyr Gly Phe Met Leu Leu Val Phe Val Ile Leu Val Ile Val Thr Val
                485                 490                 495

Cys Val Thr Ile Val Gly Thr Tyr Phe Leu Leu Asn Ala Glu Asn Tyr
                500                 505                 510

His Trp Gln Trp Thr Ser Phe Phe Ser Ala Ala Ser Thr Ala Val Tyr
            515                 520                 525

Val Tyr Leu Tyr Ser Ile Tyr Tyr Tyr Val Lys Thr Lys Met Ser
        530                 535                 540

Gly Phe Phe Gln Thr Ser Phe Tyr Phe Gly Tyr Thr Met Met Phe Cys
545                 550                 555                 560

Leu Gly Leu Gly Ile Leu Cys Gly Ala Val Gly Tyr Leu Gly Ser Asn
                565                 570                 575

Leu Phe Val Arg Arg Ile Tyr Arg Asn Ile Lys Cys Asp
            580                 585

<210> SEQ ID NO 17
<211> LENGTH: 606
<212> TYPE: PRT
<213> ORGANISM: Homo sapiens
<220> FEATURE:
<221> NAME/KEY: misc_feature
<223> OTHER INFORMATION: transmembrane 9 superfamily, protein member 1
      precursor (hMP70)

<400> SEQUENCE: 17

Met Thr Val Val Gly Asn Pro Arg Ser Trp Ser Cys Gln Trp Leu Pro
1               5                   10                  15

Ile Leu Ile Leu Leu Leu Gly Thr Gly His Gly Pro Gly Val Glu Gly
            20                  25                  30

Val Thr His Tyr Lys Ala Gly Asp Pro Val Ile Leu Tyr Val Asn Lys
        35                  40                  45

Val Gly Pro Tyr His Asn Pro Gln Glu Thr Tyr His Tyr Tyr Gln Leu
    50                  55                  60

Pro Val Cys Cys Pro Glu Lys Ile Arg His Lys Ser Leu Ser Leu Gly
65                  70                  75                  80

Glu Val Leu Asp Gly Asp Arg Met Ala Glu Ser Leu Tyr Glu Ile Arg
                85                  90                  95

Phe Arg Glu Asn Val Glu Lys Arg Ile Leu Cys His Met Gln Leu Ser
            100                 105                 110

Ser Ala Gln Val Glu Gln Leu Arg Gln Ala Ile Glu Glu Leu Tyr Tyr
        115                 120                 125

Phe Glu Phe Val Val Asp Asp Leu Pro Ile Arg Gly Phe Val Gly Tyr
    130                 135                 140

Met Glu Glu Ser Gly Phe Leu Pro His Ser His Lys Ile Gly Leu Trp
145                 150                 155                 160

Thr His Leu Asp Phe His Leu Glu Phe His Gly Asp Arg Ile Ile Phe
```

-continued

```
                165                 170                 175
Ala Asn Val Ser Val Arg Asp Val Lys Pro His Ser Leu Asp Gly Leu
                180                 185                 190
Arg Pro Asp Glu Phe Leu Gly Leu Thr His Thr Tyr Ser Val Arg Trp
                195                 200                 205
Ser Glu Thr Ser Val Glu Arg Ser Asp Arg Arg Gly Asp Asp
                210                 215                 220
Gly Gly Phe Phe Pro Arg Thr Leu Glu Ile His Trp Leu Ser Ile Ile
225                 230                 235                 240
Asn Ser Met Val Leu Val Phe Leu Leu Val Gly Phe Val Ala Val Ile
                245                 250                 255
Leu Met Arg Val Leu Arg Asn Asp Leu Ala Arg Tyr Asn Leu Asp Glu
                260                 265                 270
Glu Thr Thr Ser Ala Gly Ser Gly Asp Asp Phe Asp Gln Gly Asp Asn
                275                 280                 285
Gly Trp Lys Ile Ile His Thr Asp Val Phe Arg Phe Pro Pro Tyr Arg
                290                 295                 300
Gly Leu Leu Cys Ala Val Leu Gly Val Gly Ala Gln Phe Leu Ala Leu
305                 310                 315                 320
Gly Thr Gly Ile Ile Val Met Ala Leu Leu Gly Met Phe Asn Val His
                325                 330                 335
Arg His Gly Ala Ile Asn Ser Ala Ala Ile Leu Leu Tyr Ala Leu Thr
                340                 345                 350
Cys Cys Ile Ser Gly Tyr Val Ser Ser His Phe Tyr Arg Gln Ile Gly
                355                 360                 365
Gly Glu Arg Trp Val Trp Asn Ile Ile Leu Thr Thr Ser Leu Phe Ser
                370                 375                 380
Val Pro Phe Phe Leu Thr Trp Ser Val Val Asn Ser Val His Trp Ala
385                 390                 395                 400
Asn Gly Ser Thr Gln Ala Leu Pro Ala Thr Thr Ile Leu Leu Leu Leu
                405                 410                 415
Thr Val Trp Leu Leu Val Gly Phe Pro Leu Thr Val Ile Gly Gly Ile
                420                 425                 430
Phe Gly Lys Asn Asn Ala Ser Pro Phe Asp Ala Pro Cys Arg Thr Lys
                435                 440                 445
Asn Ile Ala Arg Glu Ile Asn Pro Gln Pro Trp Tyr Lys Ser Thr Asp
450                 455                 460
Ile His Met Thr Val Gly Gly Phe Leu Pro Phe Ser Ala Ile Ser Val
465                 470                 475                 480
Glu Leu Tyr Tyr Ile Phe Ala Thr Val Trp Gly Arg Glu Gln Tyr Thr
                485                 490                 495
Leu Tyr Gly Ile Leu Phe Phe Val Phe Ala Ile Leu Leu Ser Val Gly
                500                 505                 510
Ala Ser Ile Ser Ile Ala Leu Thr Tyr Phe Gln Leu Ser Gly Glu Asp
                515                 520                 525
Tyr Arg Trp Trp Trp Arg Ser Val Leu Ser Val Gly Ser Thr Gly Leu
                530                 535                 540
Phe Ile Phe Leu Tyr Ser Val Phe Tyr Ala Arg Arg Ser Asn Met
545                 550                 555                 560
Ser Gly Ala Val Gln Thr Val Glu Phe Phe Gly Tyr Ser Leu Leu Thr
                565                 570                 575
Gly Tyr Val Phe Phe Leu Met Leu Gly Thr Ile Ser Phe Phe Ser Ser
                580                 585                 590
```

-continued

Leu Lys Phe Ile Arg Tyr Ile Tyr Val Asn Leu Lys Met Asp
         595                 600                 605

<210> SEQ ID NO 18
<211> LENGTH: 662
<212> TYPE: PRT
<213> ORGANISM: Homo sapiens
<220> FEATURE:
<221> NAME/KEY: misc_feature
<223> OTHER INFORMATION: multispanning membrane protein p76

<400> SEQUENCE: 18

Met Ser Ala Arg Leu Pro Val Leu Ser Pro Arg Trp Pro Arg Leu
1               5                   10                  15

Leu Leu Leu Ser Leu Leu Leu Gly Ala Val Pro Gly Pro Arg Ser
                20                  25                  30

Gly Ala Phe Tyr Leu Pro Gly Leu Ala Pro Val Asn Phe Cys Asp Glu
            35                  40                  45

Glu Lys Lys Ser Asp Glu Cys Lys Ala Glu Ile Glu Leu Phe Val Asn
    50                  55                  60

Arg Leu Asp Ser Val Glu Ser Val Leu Pro Tyr Glu Tyr Thr Ala Phe
65                  70                  75                  80

Asp Phe Cys Gln Ala Ser Glu Gly Lys Arg Pro Ser Glu Asn Leu Gly
                85                  90                  95

Gln Val Leu Phe Gly Glu Arg Ile Glu Pro Ser Pro Tyr Lys Phe Thr
            100                 105                 110

Phe Asn Lys Lys Glu Thr Cys Lys Leu Val Cys Thr Lys Thr Tyr His
        115                 120                 125

Thr Glu Lys Ala Glu Asp Lys Gln Lys Leu Glu Phe Leu Lys Lys Ser
    130                 135                 140

Met Leu Leu Asn Tyr Gln His His Trp Ile Val Asp Asn Met Pro Val
145                 150                 155                 160

Thr Trp Cys Tyr Asp Val Glu Asp Gly Gln Arg Phe Cys Asn Pro Gly
                165                 170                 175

Phe Pro Ile Gly Cys Tyr Ile Thr Asp Lys Gly His Ala Lys Asp Ala
            180                 185                 190

Cys Val Ile Ser Ser Asp Phe His Glu Arg Asp Thr Phe Tyr Ile Phe
        195                 200                 205

Asn His Val Asp Ile Lys Ile Tyr Tyr His Val Val Glu Thr Gly Ser
    210                 215                 220

Met Gly Ala Arg Leu Val Ala Ala Lys Leu Glu Pro Lys Ser Phe Lys
225                 230                 235                 240

His Thr His Ile Asp Lys Pro Asp Cys Ser Gly Pro Pro Met Asp Ile
                245                 250                 255

Ser Asn Lys Ala Ser Gly Glu Ile Lys Ile Ala Tyr Thr Tyr Ser Val
            260                 265                 270

Ser Phe Glu Glu Asp Asp Lys Ile Arg Trp Ala Ser Arg Trp Asp Tyr
        275                 280                 285

Ile Leu Glu Ser Met Pro His Thr His Ile Gln Trp Phe Ser Ile Met
    290                 295                 300

Asn Ser Leu Val Ile Val Leu Phe Leu Ser Gly Met Val Ala Met Ile
305                 310                 315                 320

Met Leu Arg Thr Leu His Lys Asp Ile Ala Arg Tyr Asn Gln Met Asp
                325                 330                 335

Ser Thr Glu Asp Ala Gln Glu Glu Phe Gly Trp Lys Leu Val His Gly

-continued

```
                    340                 345                 350
Asp Ile Phe Arg Pro Pro Arg Lys Gly Met Leu Leu Ser Val Phe Leu
            355                 360                 365
Gly Ser Gly Thr Gln Ile Leu Ile Met Thr Phe Val Thr Leu Phe Phe
        370                 375                 380
Ala Cys Leu Gly Phe Leu Ser Pro Ala Asn Arg Gly Ala Leu Met Thr
385                 390                 395                 400
Cys Ala Val Val Leu Trp Val Leu Leu Gly Thr Pro Ala Gly Tyr Val
                405                 410                 415
Ala Ala Arg Phe Tyr Lys Ser Phe Gly Gly Glu Lys Trp Lys Thr Asn
            420                 425                 430
Val Leu Leu Thr Ser Phe Leu Cys Pro Gly Ile Val Phe Ala Asp Phe
        435                 440                 445
Phe Ile Met Asn Leu Ile Leu Trp Gly Glu Gly Ser Ser Ala Ala Ile
    450                 455                 460
Pro Phe Gly Thr Leu Val Ala Ile Leu Ala Leu Trp Phe Cys Ile Ser
465                 470                 475                 480
Val Pro Leu Thr Phe Ile Gly Ala Tyr Phe Gly Phe Lys Lys Asn Ala
                485                 490                 495
Ile Glu His Pro Val Arg Thr Asn Gln Ile Pro Arg Gln Ile Pro Glu
            500                 505                 510
Gln Ser Phe Tyr Thr Lys Pro Leu Pro Gly Ile Ile Met Gly Gly Ile
        515                 520                 525
Leu Pro Phe Gly Cys Ile Phe Ile Gln Leu Phe Ile Leu Asn Ser
    530                 535                 540
Ile Trp Ser His Gln Met Tyr Tyr Met Phe Gly Phe Leu Phe Leu Val
545                 550                 555                 560
Phe Ile Ile Leu Val Ile Thr Cys Ser Glu Ala Thr Ile Leu Leu Cys
                565                 570                 575
Tyr Phe His Leu Cys Ala Glu Asp Tyr His Trp Gln Trp Arg Ser Phe
            580                 585                 590
Leu Thr Ser Gly Phe Thr Ala Val Tyr Phe Leu Ile Tyr Ala Val His
        595                 600                 605
Tyr Phe Phe Ser Lys Leu Gln Ile Thr Gly Thr Ala Ser Thr Ile Leu
    610                 615                 620
Tyr Phe Gly Tyr Thr Met Ile Met Val Leu Ile Phe Phe Leu Phe Thr
625                 630                 635                 640
Gly Thr Ile Gly Phe Phe Ala Cys Phe Trp Phe Val Thr Lys Ile Tyr
                645                 650                 655
Ser Val Val Lys Val Asp
            660

<210> SEQ ID NO 19
<211> LENGTH: 586
<212> TYPE: PRT
<213> ORGANISM: Homo sapiens
<220> FEATURE:
<221> NAME/KEY: misc_feature
<223> OTHER INFORMATION: GenBank No. D87444

<400> SEQUENCE: 19

Met Arg Pro Leu Pro Gly Ala Leu Gly Val Ala Ala Ala Ala Leu Trp
1               5                   10                  15
Leu Leu Leu Leu Leu Leu Pro Arg Thr Arg Ala Asp Glu His Glu His
            20                  25                  30
```

-continued

```
Thr Tyr Gln Asp Lys Glu Glu Val Val Leu Trp Met Asn Thr Val Gly
            35                  40                  45
Pro Tyr His Asn Arg Gln Glu Thr Tyr Lys Tyr Phe Ser Leu Pro Phe
        50                  55                  60
Cys Val Gly Ser Lys Lys Ser Ile Ser His Tyr His Glu Thr Leu Gly
 65                  70                  75                  80
Glu Ala Leu Gln Gly Val Glu Leu Glu Phe Ser Gly Leu Asp Ile Lys
                85                  90                  95
Phe Lys Asp Asp Val Met Pro Ala Thr Tyr Cys Glu Ile Asp Leu Asp
            100                 105                 110
Lys Glu Lys Arg Asp Ala Phe Val Tyr Ala Ile Lys Asn His Tyr Trp
            115                 120                 125
Tyr Gln Met Tyr Ile Asp Asp Leu Pro Ile Trp Gly Ile Val Gly Glu
            130                 135                 140
Ala Asp Glu Asn Gly Glu Asp Tyr Tyr Leu Trp Thr Tyr Lys Lys Leu
145                 150                 155                 160
Glu Ile Gly Phe Asn Gly Asn Arg Ile Val Asp Val Asn Leu Thr Ser
                165                 170                 175
Glu Gly Lys Val Lys Leu Gly Ser Lys Tyr Tyr Asn Pro Asp Val Ile
            180                 185                 190
Phe Ser Lys Met Glu Lys Ser Asp Val Lys Phe Glu Asp Arg Phe Asp
            195                 200                 205
Asn Ile Leu Ile Val Leu Phe Ser His Arg Ile His Trp Phe Ser Ile
            210                 215                 220
Phe Asn Ser Phe Met Met Val Ile Phe Leu Val Gly Leu Val Ser Met
225                 230                 235                 240
Ile Leu Met Arg Thr Leu Arg Lys Asp Tyr Ala Arg Tyr Ser Lys Glu
                245                 250                 255
Glu Glu Met Asp Asp Met Asp Arg Asp Leu Gly Asp Glu Tyr Gly Trp
            260                 265                 270
Lys Gln Val His Gly Asp Val Phe Arg Pro Ser Ser His Pro Leu Ile
            275                 280                 285
Phe Ser Ser Leu Ile Gly Ser Gly Cys Gln Ile Phe Ala Val Ser Leu
            290                 295                 300
Ile Val Ile Ile Val Ala Met Ile Glu Asp Leu Tyr Thr Glu Arg Gly
305                 310                 315                 320
Ser Met Leu Ser Thr Ala Ile Phe Val Tyr Ala Ala Thr Ser Pro Val
                325                 330                 335
Asn Gly Tyr Phe Gly Gly Ser Leu Tyr Ala Arg Gln Gly Gly Arg Arg
            340                 345                 350
Trp Ile Lys Gln Met Phe Ile Gly Ala Phe Leu Ile Pro Ala Met Gly
            355                 360                 365
Val His Cys Leu Leu His Gln Phe His Ser His Leu Leu Pro Cys Phe
            370                 375                 380
Lys Ser His Ser Phe Trp Asn Asn Gly Gly Arg Leu Leu His Leu Phe
385                 390                 395                 400
Phe Cys Tyr Ser Ser Ser Lys Ser Cys Trp Tyr Asn Thr Trp Pro Lys
                405                 410                 415
Ser Val Arg Ser Ala Gln Leu Ser Leu Ser Cys Gln Cys Cys Ala Ser
            420                 425                 430
Ser Tyr Thr Gly Glu Lys Met Val His Gly Ala Ala Val Ile Val Cys
            435                 440                 445
Leu Gly Gly Ile Leu Pro Phe Gly Ser Ile Phe Ile Glu Met Tyr Phe
```

```
        450                 455                 460
Ile Phe Thr Ser Phe Trp Ala Tyr Lys Ile Tyr Val Tyr Gly Phe
465                 470                 475                 480

Met Met Leu Val Leu Val Ile Leu Cys Ile Val Thr Val Cys Val Thr
                485                 490                 495

Ile Val Cys Thr Tyr Phe Leu Leu Asn Ala Glu Asp Tyr Arg Trp Gln
            500                 505                 510

Trp Thr Ser Phe Leu Ser Ala Ala Ser Thr Ala Ile Tyr Val Tyr Met
            515                 520                 525

Tyr Ser Phe Tyr Tyr Tyr Phe Phe Lys Thr Lys Met Tyr Gly Leu Phe
530                 535                 540

Gln Thr Ser Phe Tyr Phe Gly Tyr Met Ala Val Phe Ser Thr Ala Leu
545                 550                 555                 560

Gly Ile Met Cys Gly Ala Ile Gly Tyr Met Gly Thr Ser Ala Phe Val
                565                 570                 575

Arg Lys Ile Tyr Thr Asn Val Lys Ile Asp
                580                 585

<210> SEQ ID NO 20
<211> LENGTH: 667
<212> TYPE: PRT
<213> ORGANISM: Saccharomyces cerevisiae
<220> FEATURE:
<221> NAME/KEY: misc_feature
<223> OTHER INFORMATION: Emp70 (p24a 70 kDa precursor)

<400> SEQUENCE: 20

Met Ile Tyr Lys Met Ala His Val Gln Leu Leu Leu Tyr Phe Phe
1               5                   10                  15

Val Ser Thr Val Lys Ala Phe Tyr Leu Pro Gly Val Ala Pro Thr Thr
                20                  25                  30

Tyr Arg Glu Asn Asp Asn Ile Pro Leu Leu Val Asn His Leu Thr Pro
            35                  40                  45

Ser Met Asn Tyr Gln His Lys Asp Glu Asp Gly Asn Asn Val Ser Gly
    50                  55                  60

Asp Lys Glu Asn Phe Leu Tyr Ser Tyr Asp Tyr Tyr Asn Arg Phe
65              70                  75                  80

His Phe Cys Gln Pro Glu Lys Val Glu Lys Gln Pro Glu Ser Leu Gly
                85                  90                  95

Ser Val Ile Phe Gly Asp Arg Ile Tyr Asn Ser Pro Phe Gln Leu Asn
            100                 105                 110

Met Leu Gln Glu Lys Glu Cys Glu Ser Leu Cys Lys Thr Val Ile Pro
        115                 120                 125

Gly Asp Asp Ala Lys Phe Ile Asn Lys Leu Ile Lys Asn Gly Phe Phe
    130                 135                 140

Gln Asn Trp Leu Ile Asp Gly Leu Pro Ala Ala Arg Glu Val Tyr Asp
145                 150                 155                 160

Gly Arg Thr Lys Thr Ser Phe Tyr Gly Ala Gly Phe Asn Leu Gly Phe
                165                 170                 175

Val Gln Val Thr Gln Gly Thr Asp Ile Glu Ala Thr Pro Lys Gly Ala
            180                 185                 190

Glu Thr Thr Asp Lys Asp Val Glu Leu Glu Thr Arg Asn Asp Cys Asn
        195                 200                 205

Met Val Lys Thr Tyr Glu Leu Pro Tyr Phe Ala Asn His Phe Asp Ile
    210                 215                 220
```

-continued

```
Met Ile Glu Tyr His Asp Arg Gly Glu Gly Asn Tyr Arg Val Val Gly
225                 230                 235                 240

Val Ile Val Glu Pro Val Ser Ile Lys Arg Ser Ser Pro Gly Thr Cys
                245                 250                 255

Glu Thr Thr Gly Ser Pro Leu Met Leu Asp Glu Glu Asn Asp Asn Glu
            260                 265                 270

Val Tyr Phe Thr Tyr Ser Val Lys Phe Asn Glu Ser Ala Thr Ser Trp
        275                 280                 285

Ala Thr Arg Trp Asp Lys Tyr Leu His Val Tyr Asp Pro Ser Ile Gln
290                 295                 300

Trp Phe Ser Leu Ile Asn Phe Ser Leu Val Val Leu Leu Ser Ser
305                 310                 315                 320

Val Val Ile His Ser Leu Leu Arg Ala Leu Lys Ser Asp Phe Ala Arg
                325                 330                 335

Tyr Asn Glu Leu Asn Leu Asp Asp Phe Gln Glu Asp Ser Gly Trp
            340                 345                 350

Lys Leu Asn His Gly Asp Val Phe Arg Ser Pro Ser Gln Ser Leu Thr
        355                 360                 365

Leu Ser Ile Leu Val Gly Ser Gly Val Gln Leu Phe Leu Met Val Thr
370                 375                 380

Cys Ser Ile Phe Phe Ala Ala Leu Gly Phe Leu Ser Pro Ser Ser Arg
385                 390                 395                 400

Gly Ser Leu Ala Thr Val Met Phe Ile Leu Tyr Ala Leu Phe Gly Phe
                405                 410                 415

Val Gly Ser Tyr Thr Ser Met Gly Ile Tyr Lys Phe Phe Asn Gly Pro
            420                 425                 430

Tyr Trp Lys Ala Asn Leu Ile Leu Thr Pro Leu Leu Val Pro Gly Ala
        435                 440                 445

Ile Leu Leu Ile Ile Ile Ala Leu Asn Phe Phe Leu Met Phe Val His
450                 455                 460

Ser Ser Gly Val Ile Pro Ala Ser Thr Leu Phe Phe Met Val Phe Leu
465                 470                 475                 480

Trp Phe Leu Phe Ser Ile Pro Ser Ser Phe Ala Gly Ser Leu Ile Ala
                485                 490                 495

Arg Lys Arg Cys His Trp Asp Glu His Pro Thr Lys Thr Asn Gln Ile
            500                 505                 510

Ala Arg Gln Ile Pro Phe Gln Pro Trp Tyr Leu Lys Thr Ile Pro Ala
        515                 520                 525

Thr Leu Ile Ala Gly Ile Phe Pro Phe Gly Ser Ile Ala Val Glu Leu
530                 535                 540

Tyr Phe Ile Tyr Thr Ser Leu Trp Phe Asn Lys Ile Phe Tyr Met Phe
545                 550                 555                 560

Gly Phe Leu Phe Ser Phe Leu Leu Leu Thr Leu Thr Ser Ser Leu
                565                 570                 575

Val Thr Ile Leu Ile Thr Tyr His Ser Leu Cys Leu Glu Asn Trp Lys
            580                 585                 590

Trp Gln Trp Arg Gly Phe Ile Gly Gly Ala Gly Cys Ala Leu Tyr
        595                 600                 605

Val Phe Ile His Ser Ile Leu Phe Thr Lys Phe Lys Leu Gly Gly Phe
610                 615                 620

Thr Thr Ile Val Leu Tyr Val Gly Tyr Ser Ser Val Ile Ser Leu Leu
625                 630                 635                 640

Cys Cys Leu Val Thr Gly Ser Ile Gly Phe Ile Ser Ser Met Leu Phe
```

```
                    645                 650                 655
Val Arg Lys Ile Tyr Ser Ser Ile Lys Val Asp
            660                 665

<210> SEQ ID NO 21
<211> LENGTH: 15
<212> TYPE: PRT
<213> ORGANISM: artificial
<220> FEATURE:
<223> OTHER INFORMATION: N-terminus of ICYP receptor, for generating
      antibodies

<400> SEQUENCE: 21

Phe Phe Gln His Arg Ile His Val Phe Ser Ile Phe Asn His Cys
1               5                   10                  15
```

MAMMALIAN ICYP (IODOCYANOPINDOLOL) RECEPTOR AND ITS APPLICATIONS

This application is a national phase application filed under 35 U.S.C. §371 of PCT Application No. PCT/EP97/07339, filed Dec. 12, 1997, which claims priority to European Patent Application No. 96 402719.7, filed Dec. 12, 1996.

The present invention relates to an isolated and substantially pure mammal polypeptide different from known adrenergic, serotonine and dopamine receptors, existing at least on mammalian muscle and eosinophils membranes, for instance in rat, guinea pig and humans.

The invention also relates:

to plasmids containing the genes coding for said polypeptide, to host cells transformed by genes coding for the above mentioned polypeptide, to nucleotide probes capable of hybridizing with the genes coding for the above mentioned polypeptide, and to polyclonal and monoclonal antibodies directed against the above mentioned polypeptide and which can be used for the purpose of in vitro diagnosis, A wide variety of membrane receptors for hormones and neuro-transmitters transmitters are composed of a single polypeptide chain containing seven hydrophilic sequences and may be coupled to guanine-nucleotide-binding regulatory G proteins, which upon activation by agonists or antagonists, stimulate or inhibit various effectors such as enzymes or ion channels.

Among the family of seven transmembrane domains receptors are those for adrenaline and other catecholamines, the adrenergic receptors and those for acetyl-choline and related muscarinic ligands, the muscarinic cholinergic receptors. Other similar proteins belonging to this growing family are those for serotonine, for dopamine, for tachykinins and for the pituitary glycoprotein hormones, to mention but a few.

The existence of atypical adrenergic receptors (AR), in adipocytes, in gastrointestinal tissues and in skeletal muscles has been well-established. Atypical β-adrenergic receptors (β-ARs) are defined as β-AR that can not be classified as typical β-ARs (β1-AR and β2-AR) with low β-AR antagonist effect, showing a propranolol (a classical non-selective β-AR antagonist)-resistant feature.

For instance, McLaughlin, MacDonald and co-workers characterized β-AR in rat colon (McLaughlin, MacDonald, 1990, MacDonald and Lamont, 1993; McKean and MacDonald, 1995). Propranolol was a weak antagonist against isoproterenol and BRL-37344. The propranolol-resistant responses of isoproterenol were antagonized by cyanopindolol with a $pA_2$ value of 7.12 under blockade of β1- and β2-AR effects. They reported that responses to isoproterenol in rat colon were mediated largely through β3-AR with small contribution of β1-AR and β2-AR (McKean and MacDonald, 1995). This observation is supported by Ek et al., 1986, who found β1- and β2-AR in rat colon membranes by [$^{125}$I]-pindolol binding studies. Thus, rat colon has mainly β3-AR in addition to β1- and β2-ARs. Like in guinea pig ileum, cyanopindolol acted as an antagonist at rat atypical β-AR, while it acted as a β1-, β2-AR antagonist having β3-AR agonist potency at human and mouse β3-AR (Blin et al., 1993).

Most of the pharmacological features of atypical β-ARs can be explained by β3-AR-activity; however, lack of β3-AR transcripts in skeletal muscles, or heterogeneous responses in vascular smooth muscles remained unexplained and show the complexity found in the field of receptors.

The invention solves an unresolved question with regard to the existence of polypeptide having a receptor activity other than that of β3-adrenergic receptors; in fact, it provides access to a novel receptor class present at least in muscles and in eosinophils, which displays transmembrane domains and may have signal transduction function.

The Inventors have now found, unexpectedly, that in rat colon smooth muscle membranes, there is a non-adrenergic, non-serotonine and non-dopamine receptor mediating at least inhibition of depolarized colon tonus.

The subject of the present invention is a substantially pure mammal polypeptide containing sites such that when said sites are exposed at the surface of a cell, they are able of binding iodocyanopindolol (ICYP) under blockade of α, β1, β2, β3-AR, serotonine 5-$HT_{1A}$ and serotonine 5-$HT_{1B}$ receptors, said binding being saturable, reversible, able to be displaced by a β-adrenergic receptor agonist SM-11044 with stereo-selectivity selectively but not by isoproterenol, norepinephrine, epinephrine, serotonine, dopamine or BRL-37344, and not being blocked by propanolol said polypeptide (1) having an apparent molecular weight of about 30-40 kDa when labeled with $^{125}$I-iodocyanopindolol after photo-affinity labeling and separation by electrophoresis and an apparent molecular weight of about 60-80 kDa in Western blot, and (2) generating a fragment having the following formula $DPX_1FFQHRIHX_2FSIFNX_3$ by acidic cleavage, wherein, $X_1$ represents S (SEQ ID No.5) or X (SEQ ID No.6), $X_2$ represents V (SEQ ID No.6) or W (SEQ ID No.05) and $X_3$ represents S (SEQ ID No.5) or H (SEQ ID No.6), said polypeptide being present at least on muscles and eosinophils membranes and being a non-adrenergic receptor.

Said new non-adrenergic receptor has the following affinities with different β3-AR agonists and antagonists:

SM-11044 stimulates guinea pig ileum relaxation of KCl-induced tonus more efficiently than rat white adipocyte lipolysis; SM-11044 and BRL-35135A, a potent β3-AR agonist, display the additional property of inhibiting leukotriene B4 induced-guinea pig eosinophil chemotaxis, whereas isoproterenol and BRL-37344 had no such effect. This inhibition was unaffected by the non-selective β-AR antagonist, propranolol, but was antagonized by alprenolol, β1-, β2-AR antagonist/β3-AR partial agonist.

While rat colon indeed contains β3-AR (Bensaid M. et al., 1993) in addition to β2-AR with a small population of β1-AR (Arunlakshana O. et al., 1959), the instant invention clearly shows the existence of a novel functional binding site in rat colon. This site was characterized by ligand binding and photoaffinity labeling, revealing a novel binding protein, designated here Ro-SMBP (SM-11044 binding protein or Rodent SM-binding protein).

Said new non-adrenergic SM-binding protein has also been found in human muscles (smooth and striated) (Hu-SMBP); it contains at least the sequence SEQ ID NO:1.

According to an advantageous embodiment of said protein it consists of SEQ ID NO: 14.

Said protein contains a hydrophobic C-terminal region of 356 residues, which may contain up to nine transmembrane regions.

The invention also relates to an isolated and purified nucleic acid which encodes a mammalian receptor as hereabove defined and fragments thereof.

In humans, said coding sequence includes at least SEQ ID NO:2.

According to an advantageous embodiment of said coding sequence, it consists of SEQ ID NO: 13, which corresponds to SMBP cDNA.

The said SEQ ID NO: 13 comprises in particular the following single restriction sites: BstU I, Hha I, HinP I, Ava I, Sma I, Xma I, BsaA I, Apa I, Ban II, Bsp120 I, EcoO 109 I, Sca I, Xmn I, Dra I, Nsi I, Ppu10 I, Acc65 I, Ban I, Kpn I, Bsp1407 I, Spe 1, BspD I, Cla I, Hinf I, Tfi I, Avr II, Drd 1, Esp3 I, Bpm I, PflM I, Bsm I, Alu I, BceF I, Bg1 II, BstY I, ApaL I, Age I, BsrF I, Nsp I, Nsp7524 I, NspC I, as located in FIGS. 19, 20 and 21.

This sequence encodes a polypeptide of 576 amino acid residues which contains a hydrophilic N-terminal region of 220 residues and a hydrophobic C-terminal region of 356 residues.

Said nucleic acid sequences in different mammals at least hybridizes with:

a 900 bp of SEQ ID NO:3, or a 300 bp of SEQ ID NO:4.

Said fragments are useful for detection of the gene coding for the instant new non-adrenergic receptor.

The subject of the present invention is also cDNA clones, characterized in that they comprise a sequence fragment coding for the instant non-adrenergic receptor.

According to the invention, the clone designated 24.3 comprises 1,7 kb and includes SEQ ID NO:2; it encodes the instant Hu-SMBP.

The invention also relates to synthetic or non-synthetic nucleotide probes, characterized in that they hybridize with one of the nucleic acid as defined above or with their complementary sequences or their corresponding RNA, these probes being such that they do not hybridize with the genes or the messenger RNA coding for β-adrenergic receptors.

Said probes are selected, for instance, from the group consisting of the hereabove mentioned 900 bp (SEQ ID NO:3) and 300 bp (SEQ ID NO:4) fragments and from SEQ ID NO:7 to SEQ ID NO:12, optionally labeled using a label such as a radio active isotope, a suitable enzyme or a fluorochrome.

SEQ ID NO:7 to SEQ ID NO:12 may be used as primers for amplifying one of the instant nucleic acid sequence.

The hybridization conditions are defined as follows, for the probes possessing more than 100 nucleotides: 600 mM NaCl; 60 mM Na-citrate; 8 mM Tris-HCl pH 7,5; 50 mM Na-phosphate; 1% Ficoll; 1% polyvinylpyrrolidone; 1% bovine serum albumine; 40% formamide; 0.2% SDS; 50 μg/ml salmon sperm DNA.

The invention also relates to recombinant plasmid, cosmid or phage in particular for cloning and/or expression, containing a nucleic acid sequence of the invention at one of its cloning sites (non essential for its replication).

According to an advantageous embodiment of the said plasmid, it further comprises an origin of replication for replication in a host cell, at least one gene whose expression permits selection of said host cell transformed with said plasmid, and a regulatory sequence, including a promoter permitting expression of a polypeptide having a non-adrenergic activity as defined hereabove, in said host cell.

According to an advantageous arrangement of this embodiment, the said plasmid is pcDNA3 into which is inserted, in a multisite linker, SEQ ID NO:2, wherein said plasmid is deposited with the Collection Nationale de Cultures de Microorganismes [National Collection of Microorganism Cultures] (CNCM held by the PASTEUR INSTITUTE, dated Dec. 10, 1996, under No. I-1795.

The invention also relates to a host cell transformed by a recombinant plasmid as previously defined comprising the elements of regulation making possible the expression of the nucleotide sequence coding for the instant polypeptide in this host.

Such a cell is capable of expressing a SMBP according to the instant invention.

According to an advantageous embodiment, the host cell consists, in particular, in mammalian cell lines.

The invention also relates to antibodies directed specifically against the instant polypeptide, these antibodies being such that they recognize neither known α or β adrenergic, nor serotonine, nor dopamine receptors.

Advantageously, said new non-adrenergic receptor according to the invention constitute a tool for the selection of ligand participating in the activation or in the inhibition of these receptors.

The invention also relates to a method for assaying a substance for agonist or antagonist activity towards a polypeptide according to the invention, which method comprises:

placing the substance in contact with tissue membrane proteins or a transformed host cell expressing a polypeptide according to the invention under conditions which permit binding between said polypeptide binding sites and an agonist or an antagonist thereto and measuring an appropriate transduction signal.

The invention also relates to a process for studying the binding affinity of a compound for a polypeptide according to the invention, which process comprises:

transforming a host cell by an expression vector comprising a nucleotide sequence coding for the instant receptor, culturing said transformed host cell under conditions which permit the expression of said receptor encoded by said nucleotide sequence and the transfer of the expressed receptor polypeptide to the membrane of the said transformed host cell so that transmembrane sequences of said receptor polypeptide are embedded in the cell membranes of the transformed host cell;

placing said transformed host cell in contact with said compound and measuring the quantity of said compound bond to said receptor polypeptide.

The invention also relates to a process for studying the binding affinity of a compound for a polypeptide according to the invention, which process comprises:

extracting membrane proteins corresponding to the instant receptor polypeptide from appropriate tissues or cells such as muscles, placing said membrane proteins in contact with said compound and measuring the quantity of said compound bond to said receptor polypeptide.

Functional roles of this polypeptide receptor would involve relaxation of depolarized-intestinal smooth muscle or inhibition of eosinophil chemotaxis.

Specific agonist for this new receptor will display at least a therapeutic potentiality in gastrointestinal diseases based on depolarized-tonus, allergic asthma and hypereosinophilic syndrome based on eosinophil accumulation.

Thus, the instant polypeptide receptor makes possible to develop drugs for at least gastrointestinal diseases based on depolarized-tonus, allergic asthma and hypereosinophilic syndrome.

Besides the foregoing arrangements, the invention also comprises other arrangements which will become apparent from the description which follows, reference being made to the attached drawings wherein:

FIG. 1: Preparative SDS-PAGE followed by autoradiography of 50 mg solubilized rat colon membranes photoaffinity-labeled with 0.5 nM [$^{125}$I]-ICYP-diazirine in the presence of 10 µM 5-HT, 10 µM phentolamine and 20 µM propranolol;

FIG. 2: Analytical chemical cleavage of SMBP. The isolated-labeled protein of 34 kDa was incubated with distilled water (lane 1), 70% formic acid (lane 2), 10% cyanogen bromide in 70% formic acid (lane 3), 75% trifluoroacetic acid (lane 4) or 10% cyanogen bromide in 75% trifluoroacetic acid (lane 5) for 24 h at room temperature, separated by Tricine-SDS-PAGE followed by autoradiography. Arrows show 8, 10 and 12 kDa labeled fragments;

FIG. 3: Preparative cyanogen bromide-cleavage of SMBP. The isolated-labeled proteins of 34 kDa were incubated with 10% cyanogen bromide in 70% formic acid for 24 h at room temperature. An aliquot of the cleaved-products was resolved on tricine-SDS-PAGE followed by autoradiography. Arrows show 8, 10 and 12 kDa labeled fragments.

FIG. 4: Analytical chemical cleavage of SMBP. FIG. 4a: the partially purified labeled proteins were incubated with distilled water (lane 1), 70% formic acid (lane 2) or 1% cyanogen bromide in 70% formic acid (lane 3) for 24 h at room temperature or FIG. 4b: the partially purified labeled proteins were incubated with distilled water (lane 1), 70% formic acid (lane 2) for 72 h at 37° C., separated by Tricine-SDS-PAGE and subjected to autoradiography.

FIG. 5: Preparative acid-cleavage of SMBP. The isolated-labeled protein of 34 kDa was incubated with 70% formic acid for 72 h at 37° C. An aliquot of the cleaved-products was resolved on tricine-SDS-PAGE followed by autoradiography. Attows shows 8 kDa labeled fragment.

FIG. 6: Reverse-phase HPLC purification of the photoaffinity-labeled formic acid-cleaved 8 kDa fragment. The fragment isolated from tricine-SDS-PAGE gels was further purified by reverse-phase HPLC. Fragment was eluted from the C4 column with a linear gradient of 30-98% buffer B in 120 min (----). Radioactive profile for 8 kDa labeled fragment was shown (●). Based on the amount of recovered radioactivity, HPLC column recovery was 91.6%.

FIG. 7: Enzyme immunoassay (ELISA) of antiserum (●), preimmunized-serum (○) or affinity-purified antibody (■, α8-antibody) on plate coated with free peptide. Rabbit polyclonal antibody was raised against the synthetic peptide corresponding to the N-terminal sequence of the 8 kDa fragment.

FIG. 8: Immunoprecipitation of the solubilized photoaffinity-labeled SMBP. Solubilized-rat colon membranes photoaffinity-labeled with 1.5 nM [$^{125}$I]-ICYP-diazirine in the presence of 10 µM 5-HT, 10 µM phentolamine, 20 µM propranolol and 1.1 mM ascorbic acid were immunoprecipitated by ½₀₀ diluted-preimmunized serum (lane 1) or 10 µg of α8-antibody (lane 2).

FIG. 9: Western blotting of the rat colon membrane proteins. Lane 1 shows control (½₀₀ diluted-preimmunized serum was used). The 70 kDa band was detected by 2 µg/ml α8-antibody (lane 2). The detection was inhibited when antibody was preincubated with 10 µg/ml specific peptide (lane 3).

FIG. 10: Relationship between the efficacy of β-AR agonists in the rat colon and white adipocytes, in the presence of 10 µM phentolamine and 1 µM propranolol. The linear regression line of the four agonists, except SM-11044, is shown in figure (r=0.97, p<0.05). The correlation coefficient, when calculated with SM-11044, was not significant (r=0.87, p>0.05). Data represent mean pD2 values±SEM (from Table 1).

FIG. 11: Time-course of association (○, solid line) and dissociation (●, dashed line) of 1 nM [$^{125}$I]-ICYP specific binding to rat colon membranes, in the presence of 10 µM 5-HT, 10 µM phentolamine and 20 µM propranolol. Reversibility of binding was obtained by the addition of 100 µM SM-11044 at equilibrium (30 min). Data represent mean of two experiments performed in duplicate.

FIG. 12: Total, non-specific and specific binding of [$^{125}$I]-ICYP to rat colon membranes, in the presence of 10 µM 5-HT, 10 µM phentolamine and 20 µM propranolol. Non-specific binding was determined in the presence of 100 µM SM-11044. Data represent mean of two experiments performed in duplicate. The inset shows Scatchard's plot of the specific binding (r=−0.978, p<0.001). The Kd was 11.0±0.95 nM and the Bmax was 716.7±21.12 fmol/mg protein.

FIG. 13: Displacement of 1 nM [$^{125}$I]-ICYP specific binding to rat colon membranes by (a) catecholamines, 5-HT and (b) stereo-isomers of SM-11044, in the presence of 10 µM 5-HT, 10 µM phentolamine and 20 µM propranolol. Data represent mean of two to four experiments performed in duplicate.

FIG. 14: SDS-PAGE followed by autoradiography of solubilized rat colon membranes photoaffinity-labeled with 1.5 nM [$^{125}$I]-ICYP-diazirine in the presence of 10 µM 5-HT, 10 µM phentolamine and different competitors, Lane 1, control; lane 2, displacement by 20 µM propranolol; lane 3, displacement by 20 µM propranolol and 100 µM BRL-37344; lane 4, displacement by 20 µM propranolol and 100 µM SM-11044.

FIG. 15: Two-dimensional SDS-PAGE followed by autoradiography of solubilized rat colon membranes photoaffinity-labeled with 1.5 nM [$^{125}$I] ICYP-diazirine in the presence of 10 µM 5-HT, 10 µM phentolamine and 20 µM propranolol.

FIG. 16: Tryptic cleavage of the photoaffinity-labeled rat colon membranes. The partially purified labeled proteins were incubated without (lane 1) or with 50 µg trypsin (lane 2) for 24 h at 37° C., separated by Tricine-SDS-PAGE and subjected to autoradiography.

FIG. 17: Displacement of 1 nM [$^{125}$I]-ICYP specific binding to rat skeletal muscle membranes by SM-11044 and (−)isoproterenol, in the presence of 10 µM 5-HT, 10 µM phentolamine and 20 µM propranolol. Data represent mean±S.E.M of two experiments performed in duplicate.

FIG. 18: Human multiple tissue northern blot hybridized with labeled 300 bp probe. Washes at 2×SSC, 0.05% S.D.S., at room temperature and exposure on Hyperfilm MP with two intensifying screens at −80° C. for three days. (A) Northern blot hybridization was performed on polyadenylated mRNA from 8 different smooth and striated human muscles. (B) similar analysis with a variety of non muscular tissues (heart, brain, placenta, lung, liver, kidney and pancreas). On the left: scale indicates RNA molecular weight marker in kilobases (Kb).

FIGS. 19, 20 and 21 illustrate the restriction map of SEQ ID NO: 13 (all sites: FIG. 19(A)-(F); unique sites only: FIG. 20 and FIG. 21).

FIG. 22 illustrates a sequence comparison of SMBP (SEQ ID NO: 15) with known proteins (Arabidobsis Emp70 protein (SEQ ID NO: 16), hMP70 protein (SEQ ID NO: 17), multimembrane spanning p76 protein (SEQ ID NO: 18), GenBank No. D87444 protein (SEQ ID NO: 19) and S. cerevisiae Emp70 protein (SEQ ID NO: 20)).

Figure 23:
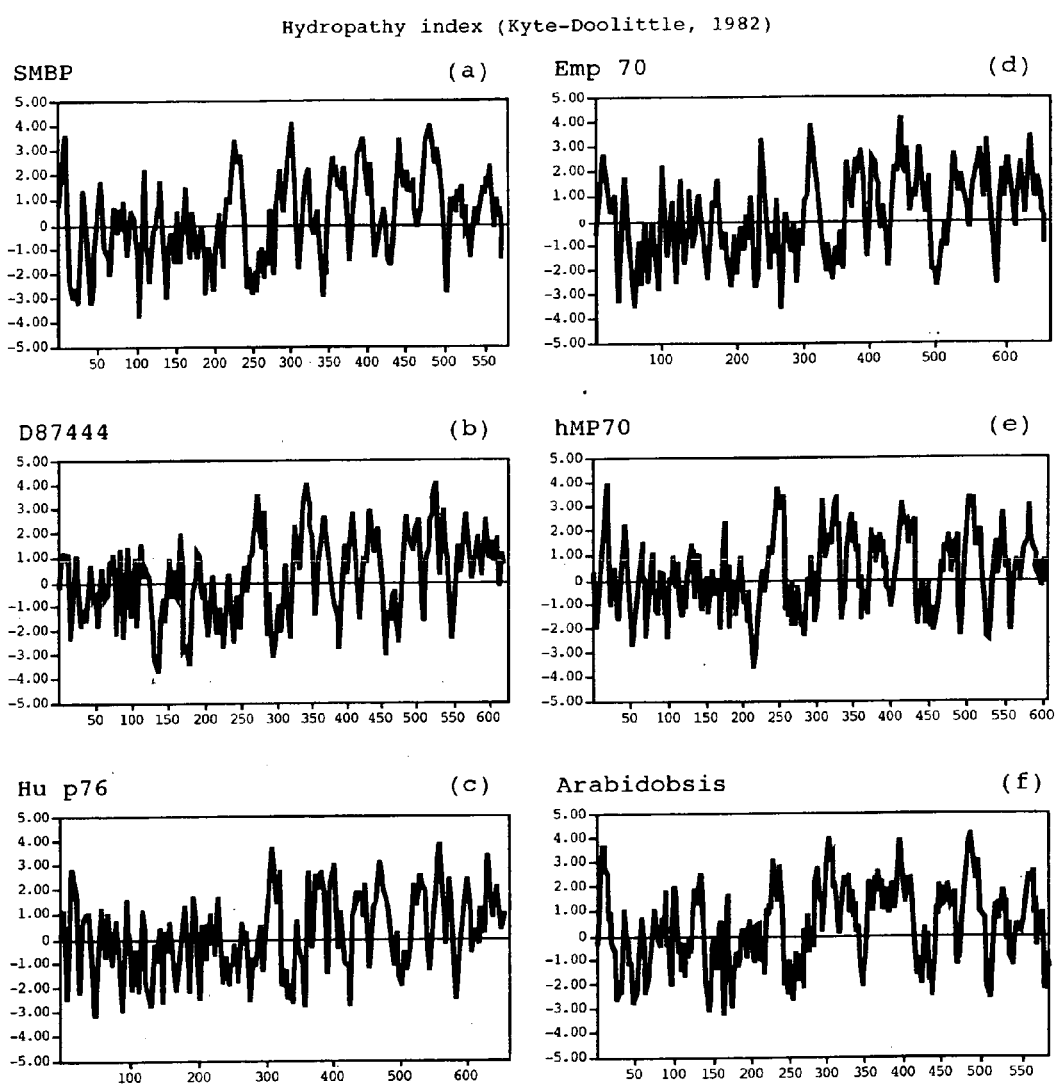
Figure 23:
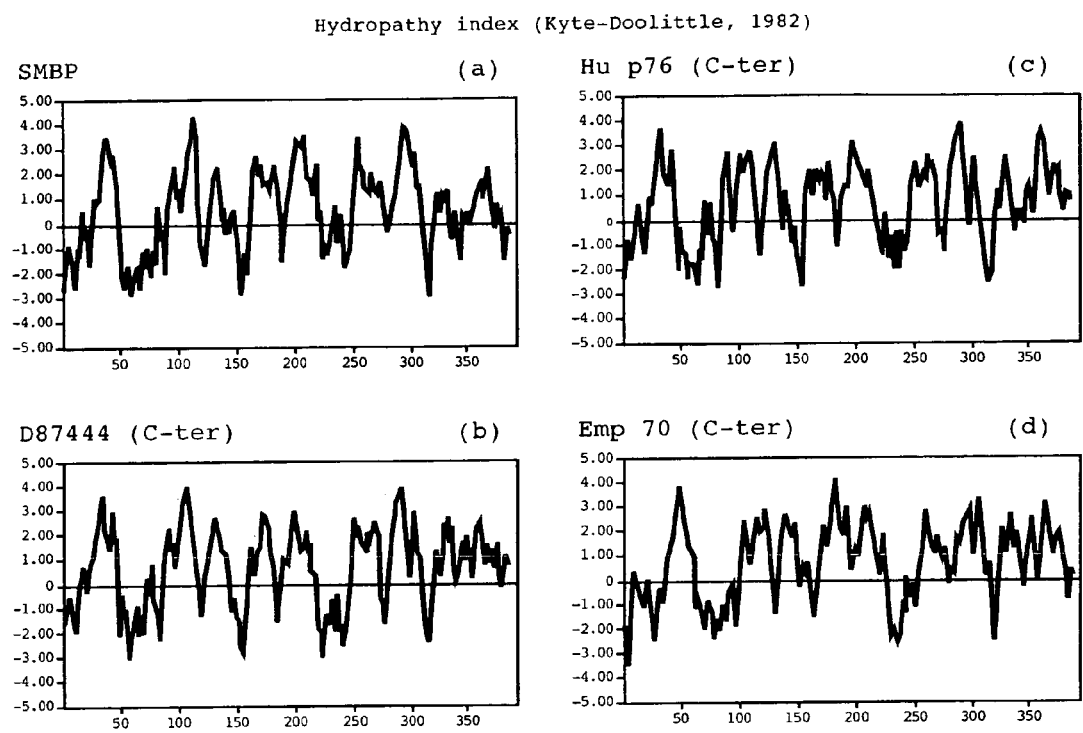

FIG. 23 illustrates (A) a comparison of hydropathy profiles (Kyte & Doolittle) by GeneJockey Sequence Processor program between SMBP (a) and the homologous proteins D87444 (b), Hu p76 (c), hMP70 (e), Emp70 from yeast (d) and Arabidobsis protein (f). (B) Comparison of the hydropathy profiles (Kyte & Doolittle method) of the C-terminal hydrophobic region between SMBP (a) and the homologous proteins D87444 (b), Hu p76 (c) and Emp70 of yeast (d).

FIG. 24 illustrates the sequences (A) and positions (B) corresponding to the hydrophobic stretches (boxes in FIG. 24A), in relation to the nucleic acid (SEQ ID NO: 13) and protein (SEQ ID NO: 14) sequences.

Figure 25:
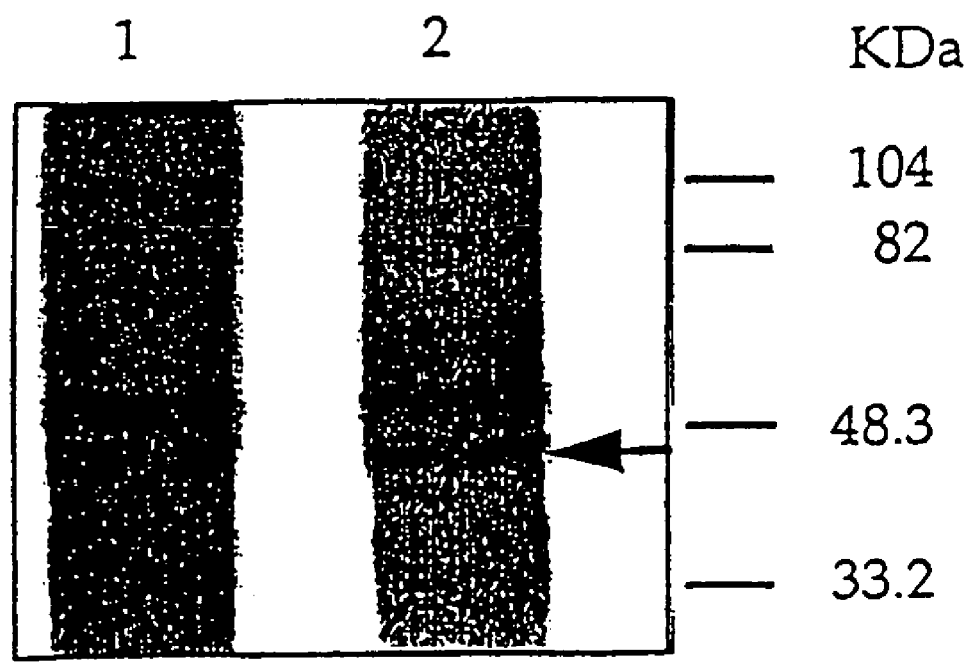

FIG. 25 illustrates immunoprecipitation of ($^{125}$I)-iodinated cell membrane proteins by α8-antibody: lane 1: COS cells transfected with a vector containing the angiotensin receptor AT2R; lane 2: COS cells transfected with a vector containing the SMBP nucleotide sequence.

EXAMPLE 1

Isolation and Characterization of the Instant Receptor in Rat Colon Smooth Muscle Membranes 1) Materials and Methods SM-11044 ((L)-threo-3-(3,4-dihydroxyphenyl)-N-[3-(4-fluorophenyl) propyl] serine pyrrolidine amide hydrobromide) and (±)-cyanopindolol were synthesized at Sumitomo Pharmaceuticals (Osaka, Japan). (−)-3-[$^{125}$I] iodocyanopindolol ([$^{125}$I]-ICYP) and (±)-3 [$^{125}$I]-iodocyanopindolol-diazirine ([$^{125}$I]-ICYP-diazirine) were purchased from Amersham (Buckinghamshire, England). All other materials were reagent grade.

Rat Colon Membrane Preparation

Frozen rat colons (SD strains, male and female) were purchased from Pel-Freeze Biologicals (Arkansas, USA). Membranes from colon smooth muscles were prepared as essentially described by Ek et al., 1986, with the slight following modifications. The colon segment was washed in ice-cold Tris-saline (10 mM Tris/HCl, 154 mM NaCl, (pH 7.4)), cut open longitudinally and the mucosa was removed by scrubbing with a glass slide on ice-cold plastic plate. The smooth muscle preparations were homogenized with a Polytron homogenizer for 1 min. The homogenate was filtered through a gauze and centrifuged (1,500×g for 20 min at 4° C.), the supernatant was collected and centrifuged (50,000×g for 20 min at 4° C.). The pellet comprising the membranes was resuspended in Tris-saline and was stored at −80° C. until use. The protein concentration was determined by Bio-Rad protein assay kit (Bio-Rad USA).

Binding Assays in Rat Colon Membranes

Saturation binding studies were performed in a final volume of 200 μl of Tris-saline containing 50 μg membrane proteins and different concentrations (0.05-25 nM) of [$^{125}$I]-ICYP, in the presence of 10 μM serotonine (5-HT), 10 μM phentolamine, 20 μM (±) propranolol and 1.1 mM ascorbic-acid pH 7.4), to block possible 5-HT receptors, ARs and oxidation of catecholamines, respectively. The [$^{125}$I]-ICYP was used after removing methyl alcohol by compressed air to avoid the influence of the solvent. Incubations were carried out at 37° C. for 30 min in a shaking water-bath incubator and terminated by addition of 4 ml of ice-cold Tris-saline followed by rapid filtration under vacuum on Whatman GF/B filter presoaked in Tris-saline containing 0.1% polyethyleneimine (pH 7.4). The filters were washed three times with 4 ml of ice-cold Tris-saline, transferred to plastic tubes and counted in a γ-counter.

Photoaffinity Labeling of the Rat Colon Membranes

Photoaffinity labeling was performed in a final volume of 10 ml of Tris-saline containing 50 mg membranes, 0.5 nM [$^{125}$I]-ICYP-diazirine, supplemented with 10 μM 5-HT, 10 μM phentolamine, 20 μM (±) propranolol and 1.1 mM ascorbic acid (pH 7.4) were incubated at 37° C. for 60 min in the dark in a shaking water-bath incubator; the reaction was terminated by addition of 20 ml of ice-cold Tris-saline followed by a rapid centrifugation (50,000×g for 10 min at 4° C.). The membranes were resuspended in 2-3 ml of the same buffer and irradiated with a UV lamp for 110 min with cooling by circulating water (Guillaume et al., 1994). The labeled membranes were diluted with 20 ml of ice-cold Tris-saline, centrifuged (50000×g for 30 min at 4° C.). The labeled membranes were immediately denatured in SDS-reducing buffer (5% SDS, 1% 2β-mercaptoethanol, 10% glycerol, 0.002% bromophenol blue, 50 mM Tris/HCl, pH 6.8) for 1 h or more at room temperature before electrophoresis.

Preparative SDS-PAGE and Extraction of the Photoaffinity-Labelled Proteins

Preparative SDS-PAGE was performed with a large size (160 mm width×200 mm height×3 mm thickness) of 12% separating and 4% stacking polyacrylamide gels (40% T, 2.6% C) under reducing conditions essentially according to the methods of Laemmli, 1970. After electrophoresis, the gels were packed in a plastic bag and auto-radiographed for 3 days at 4° C. on X-OMAT™ AR film (Eastman Kodak Co., USA). The photoaffinity labeled proteins were extracted by passive extraction, as follows. The radioactive 34 kDa band was cut out and crushed to small pieces of less than 3×3×3 mm³ by squeezing out using 10 ml disposable plastic syringe (Terumo, Japan). The gels were immersed in twice volume of 100 mM Tris/HCl (pH 8.0) containing 0.1% SDS (extraction buffer), and incubated for 16 h at 37° C. with rotating. The extract was recovered using a SPIN-XII (0.45 μm pore size, Costar, USA) at 1,500×g for 30 min. The remaining gel pieces were again immersed in twice volume of extraction buffer, incubated for 2 h at 37° C. with rotating, and the extract was recovered as described above. The two extracts were combined and concentrated to at maximum 0.5 ml using Centriprep 10 and Centricon 10 (Amicon, USA) and kept at −20° C.

Chemical Cleavage of the Extracts from Preparative SDS-PAGE and Purification by HPLC The 34 kDa photoaffinity-labeled protein extracted from the preparative SDS-PAGE were washed twice by distilled water using Centricon 10 lyophilized by vacuum concentrator and treated with 200 μl of 70% formic acid or 10% CNBr/70% formic acid for 24 h at room temperature, or 70% formic acid for 72 h at 37° C. in the dark. The cleaved products were diluted with 500 μl distilled water and lyophilized. This washing procedure was repeated three times. The cleaved products were dissolved in SDS-reducing buffer and neutralized by addition of aliquots of 30% NaOH until changing the coloration to blue, and were separated by tricine-SDS-PAGE. The gels were dried and autoradiographed. The labeled bands were cut out, passively extracted and blotted on PVDF membranes by centrifugation (ProSpin™, Applied Biosystems, USA). The membranes were washed 3 times with 1 ml of 20% methanol to remove SDS and salts. The fragments were extracted by 200 μl of 75% hexafluoro-isopropanol. Each elution was dried to 20 μl in vacuum concentrator, dissolved in 75 μl DMSO and 75 μl of starting buffer (15% acetonitrile-15% isopropanol-0.5% TFA; buffer A) and loaded on a C4 reverse phase column (Aquapore Butyl BU-300, 2.1 mm ID, 10 mm length, Applied Biosystems). Separation was carried out by a 120 min gradient elution at 40 °C. with 50% acetonitrile-50% isopropanol containing 0.5% TFA (buffer B) at a flow rate of 0.35 ml/min using a Waters 625 LC System. The gradient started from 30% to 98% buffer B. The elution of fragments was monitored by the absorbance at 210 and 275 nm, and the elution of radioiodinated products was monitored by γ-counting of the fractions.

Tricine-SDS-PAGE

Chemical cleaved fragments were separated on a Tricine gel system under reducing conditions (Schägger H. et al., 1987) using 18% polyacrylamide separating get containing 10.7% glycerol. The gels aged for 16 h to allow for decomposition of reactive chemical intermediates after polymerization.

Amino Acid Sequencing

Amino acid sequence determination was performed by Edman degradation, 1967, with an Applied Biosystems 473A protein sequencer. Samples were applied to precycled filters, coated with Polybrene (Biobrene, Applied Biosystems) to reduce peptide-wash-out and to improve initial yields.

Antibody Preparation

Antibody was prepared as essentially described by Guillaume et al. (Eur. J. Biochem., 1994, 224, 761-770).

Briefly, based on the determined amino acid sequences, peptides were synthesized adding a cysteine residue at C-terminal residue to facilitate coupling to the carrier protein (Keyhole limpet hemocyanin, KLH). The synthetic peptides were conjugated to KLH through their cysteine residues. A 0.4 mg of the peptide-conjugate, suspended in Freund's complete adjuvant, was intradermally injected into rabbit. Boosters were given 4 times at 2 weeks intervals by injection of a 0.2 mg of the peptide-conjugate suspended in Freund's incomplete adjuvant. Two weeks later the final immunization, antiserum was recovered from whole blood.

Antibody was purified by affinity chromatography on a column containing the synthetic peptide coupled to activated thiol-Sepharose-4B (Pharmacia) through a cysteine at C-terminal residue, and the antibody titer level against the free peptide without conjugation to KLH was determined by ELISA.

Immunoprecipitation

Total amounts of 10 mg membranes were photoaffinity-labeled with 1.5 nM [$^{125}$I]-ICYP-diazirine in the presence of 10 μM, 5-HT, 10 μM phentolamine, 20 μM propranolol and 1.1 mM ascorbic acid in 10 ml of Tris-saline (pH 7.4). Membranes were solubilized at 1 mg membrane protein/ml of Tris-saline containing 2% n-octylglucoside (n-octyl β-D-glucopyranoside, Sigma) for 2 h on ice with occasional mixing. The solubilized-proteins were separated from the insoluble material by centrifugation (200,000 ×g, 30 min at 4° C.). The proteins were treated with 8 M urea for 1 h at room temperature with occasional mixing and were washed 5 times with Tris-saline using Centricon 10. The solubilized-membrane proteins were dissolved in 1 ml Tris-saline containing 0.1% Tween-20 and were incubated with 10 μg antibody and 50 μl protein-A-agarose beads (Boehringer-Mannheim. Germany) for 16 h at 4° C. with rotating. The precipitant was gently washed 5 times with ice-cold Tris-saline containing 0.1% Tween-20 and denatured in SDS-reducing buffer for more than 1 h at room temperature. The immunoprecipitated proteins were subjected to 12% SDS-PAGE and autoradiographed.

Western Blotting

Photoaffinity-labeled membranes (40 μg protein) were separated by 12% SDS-PAGE. Electrotransfer of proteins onto nitrocellulose was carried out essentially according to Towbin et al., 1979, on a Trans-Blot SD apparatus (Bio-Rad) for 1 h at a current intensity of 1 mA/cm$^2$. Nitrocellulose membranes were washed three times with Dulbecco's phosphate buffered saline (PBS) containing 0.2% Tween-20 and were saturated in PBS containing 5% skimmed milk powder and 0.2% Tween-20 for 1 h at room temperature. Antibody (2 μg/ml in PBS containing 1% skimmed milk powder and 0.2% Tween-20; buffer C) was allowed to react for 16 h at 4° C.

After three times washing in buffer C, the nitrocellulose strips were incubated for 45 min at room temperature with peroxidase-conjugated affinity-purified Goat anti-rabbit IgG (Jackson Immuno-Research Laboratories, USA) at a 1/2500 dilution in buffer C, washed three times in buffer C. After washing in PBS containing 0.2% Tween-20, reactive bands were visualized with an ECL kit (Amersham, England). In inhibition experiments, antibody was preincubated for 2 h at 37° C. with free peptide at a concentration of 10 μg/ml in buffer C.

2) Results

Extraction of the Photoaffinity-Labeled SMBP

Membrane proteins of 2.0 g were collected from 600 rat colon smooth muscles. The ligand binding activity of SMBP was assessed by [$^{125}$I]-ICYP under blockade of adrenergic and serotonine receptors. Scatchard plot analysis revealed a single class of binding sites with a dissociation constant (Kd) of 7.22±0.007 nM and a maximum number of binding sites (Bmax) of 1.13 ±0.071 pmol/mg membrane protein (two independent experiments performed duplicate, expressed as means±SD).

Figure 1:
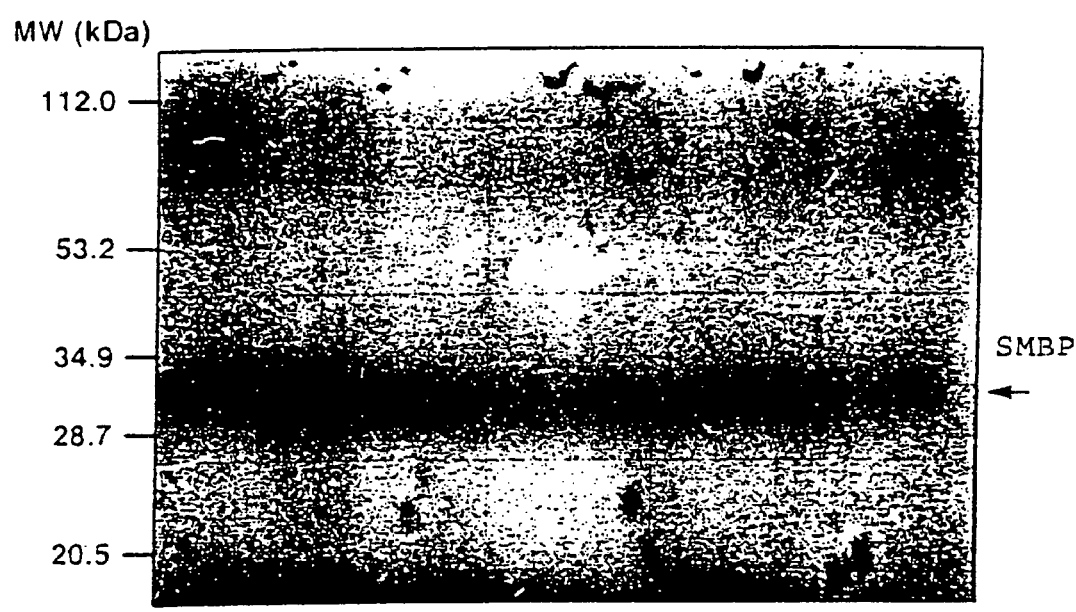

The SMBP was too hydrophobic to separate by any column chromatography such as reverse-phase HPLC with C4 column (Aquapore Butyl BU-300, Applied Biosystems), ion exchange chromatography (Aquapore Weak Anion AX-300, Applied Biosystems), chromatofocusing (PBE 94 and Polybuffer 74, Pharmacia), hydroxyapatite chromatography (BioGel HPHT, Bio-Rad). Preparative SDS-PAGE was performed to separate SMBP just after the photoaffinity labeling. Fifty mg of the labeled-membranes could be loaded on a set of polyacrylamide gels without serious diffusion of the 34 kDa labeled-SMBP (FIG. 1). The passive extraction of 34 kDa bands yielded 79.3-86.2% of the total radioactive proteins in gels.

Chemical Cleavage, Purification and Sequencing

Figure 2:
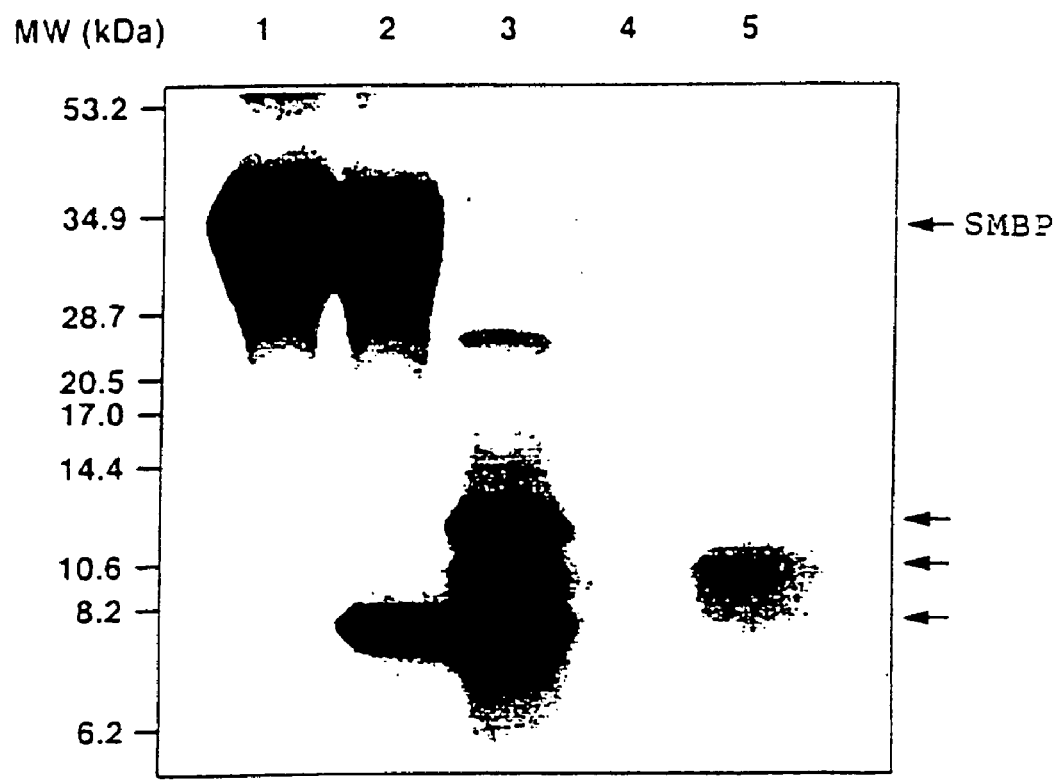

Chemical cleavage has some advantage in contrast to proteolytic digestion; it avoids contamination by protease itself, and produces limited numbers of large fragments. Analytically, each 1 mg of the labeled 34 kDa protein was treated with 10% CNBr in 70% formic acid or in 75% TFA to compare the effect of acid. In formic acid condition, CNBr generated three labeled fragments of 8, 10 and 12 kDa, and formic acid alone generated a single 8 kDa labeled fragment. In the acid condition with TFA, most of the labeling was dissociated by acid itself, a single 10 kDa labeled fragment was observed by CNBr cleavage (FIG. 2).

Figure 3:
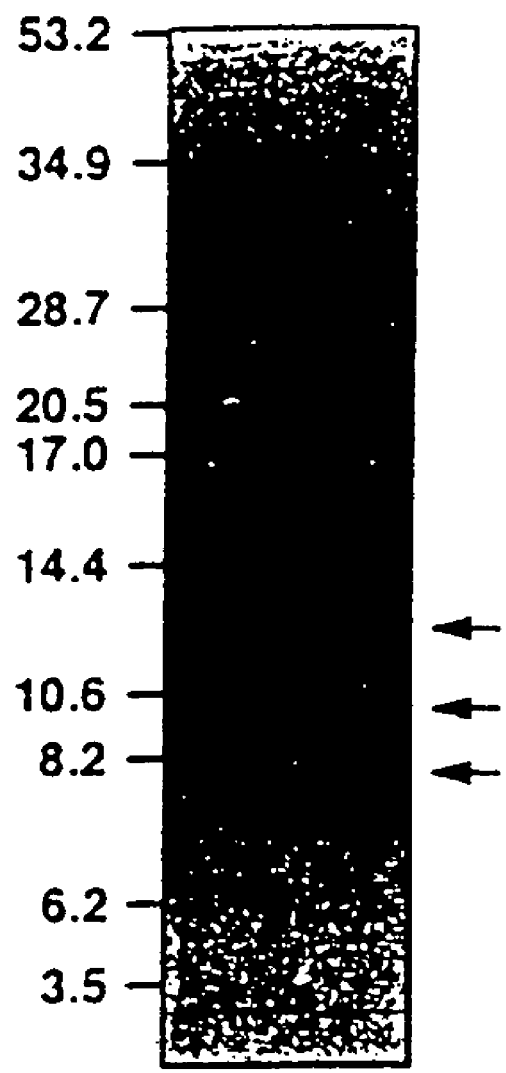

The extract of the labeled 34 kDa protein from 400 mg membranes (411794 cpm) was preparatively cleaved by CNBr/formic acid, and an aliquot of the cleaved-products was resolved on tricine-SDS-PAGE gels. Three labeled fragments of major 12 kDa and minor 8 and 10 kDa were observed on autoradiogram of coomasie blue stained gels (FIG. 3).

Figure 4:
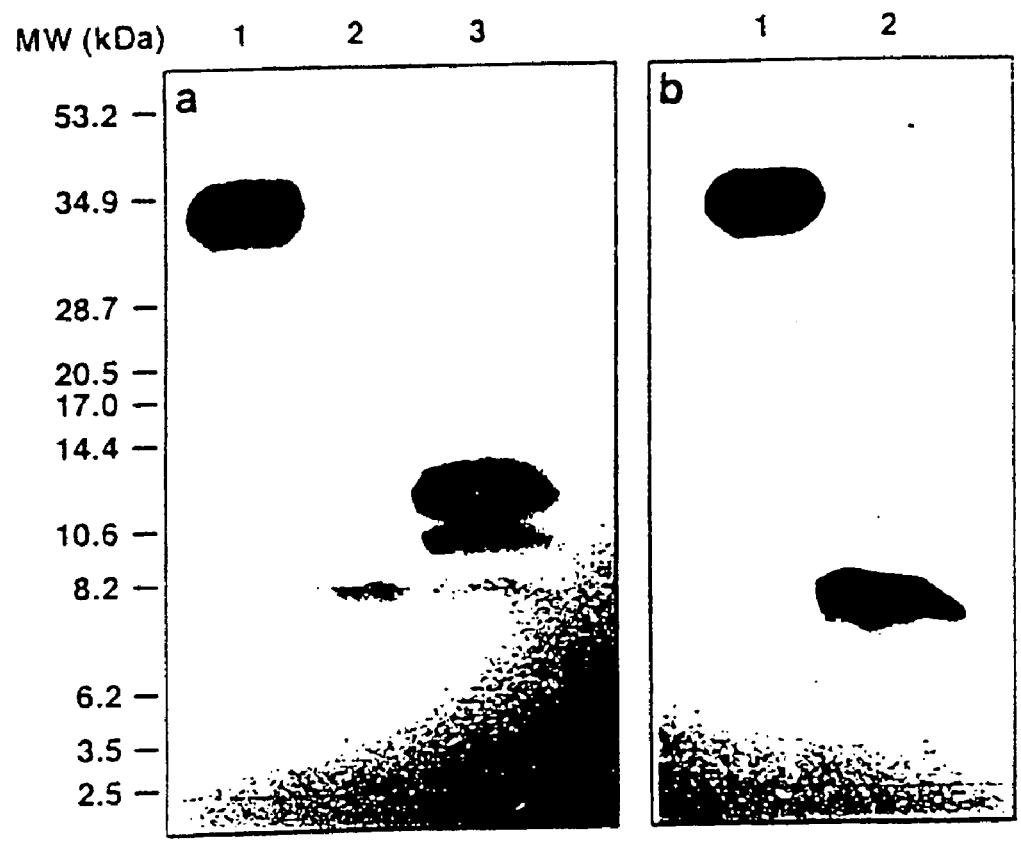

Cleavage at methionine residues by CNBr/formic acid treatment for 24 h at room temperature of the photoaffinity-labeled 34 kDa protein yielded three labelled-fragments (8, 10 and 12 kDa, FIG. 4a, lane 3). Treatment by formic acid alone generated a single 8 kDa fragment (FIG. 4a, lane 2), and the density of the 8 kDa band increased upon prolonged incubation (for 72 h at 37° C., FIG. 4b, lane 2).

Figure 5:
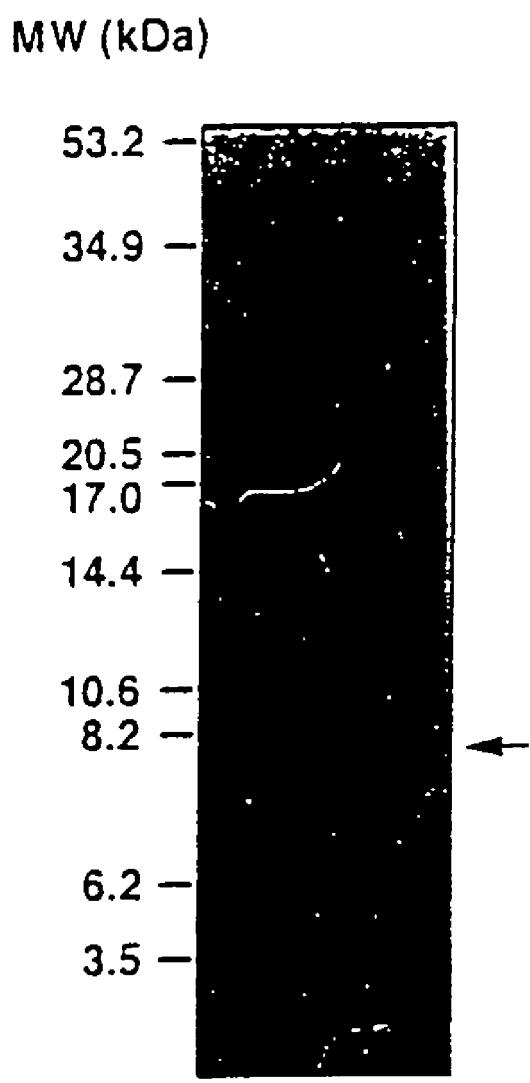
Figure 6:
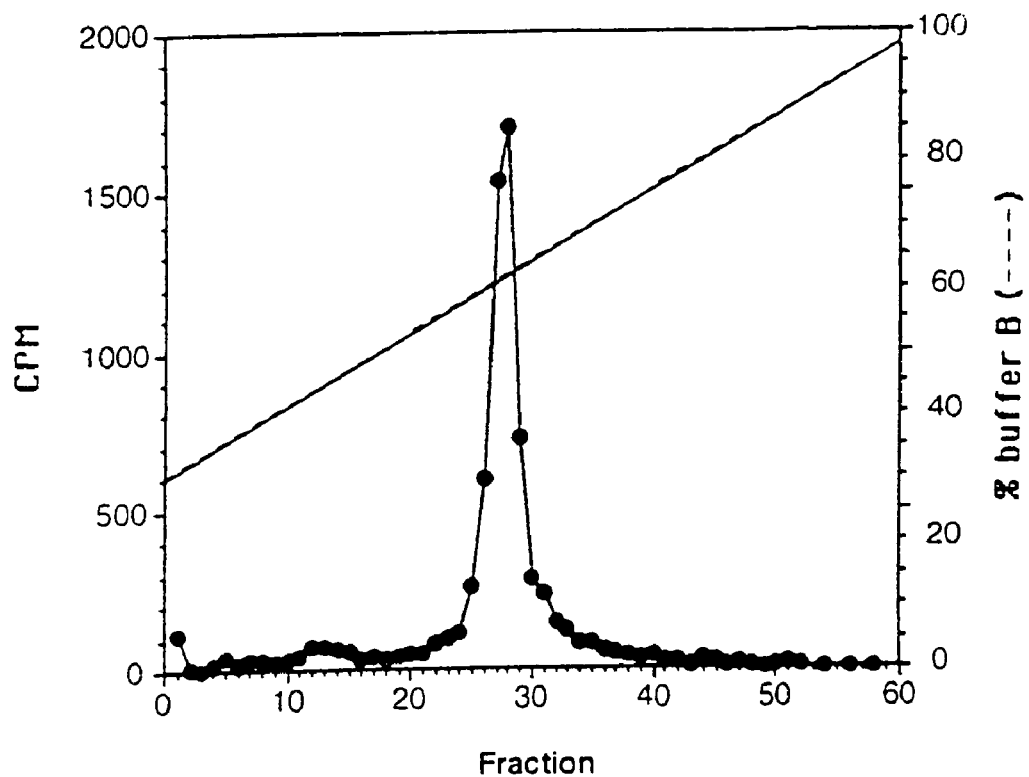

The extract of the labeled 34 kDa protein from 400 mg membrane (381198 cpm) was preparatively cleaved by formic acid, and an aliquot of the cleaved-products was resolved on tricine SDS-PAGE gels. A single labeled-fragment of 8 kDa was observed on autoradiogram of coomasie blue stained-gels (FIG. 5). The radioactive 8 kDa fragment (total 21400 cpm) in preparative scale was extracted by passive extraction from tricine-SDS-PAGE gels without coomasie blue staining, and was blotted on PVDF membranes (19581 cpm). The fragment was extracted from PVDF membranes (10045 cpm) and further purified by reverse-phase HPLC. One radioactive peak was observed at 62% buffer B (fraction no 27 and 28; total 3239 cpm, FIG. 6). Total recovery yield of the initial radioactivity was 91.6%. The peak fractions were submitted to protein sequencer, and the resulting amino acid sequence was determined as follows:

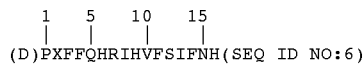
(D)PXFFQHRIHVFSIFNH(SEQ ID NO:6)

Parenthesis; expected amino acid

X; undetermined amino acid.

Analytical CNBr-cleavage indicated that cleavage at methionine residue in the presence of TFA, which improve the cleave at CNBr-resistant bonds such as Met-Thr or Met-Ser (Fontana A. et al., 1986), generated a single 10 kDa fragment.

In formic acid condition, CNBr generated three labeled fragments of 8, 10 and 12 kDa, and formic acid alone generated a single 8 kDa labeled fragment. These data suggest that 12 kDa fragment contains a CNBr-resistant methionine residue cleaved to 10 kDa by CNBr/TFA and that the 8 kDa fragment by formic acid alone is a product by cleavage at acid-sensitive bond such as Asp-Pro.

Immunoprecipitation and Western blotting

Figure 7:
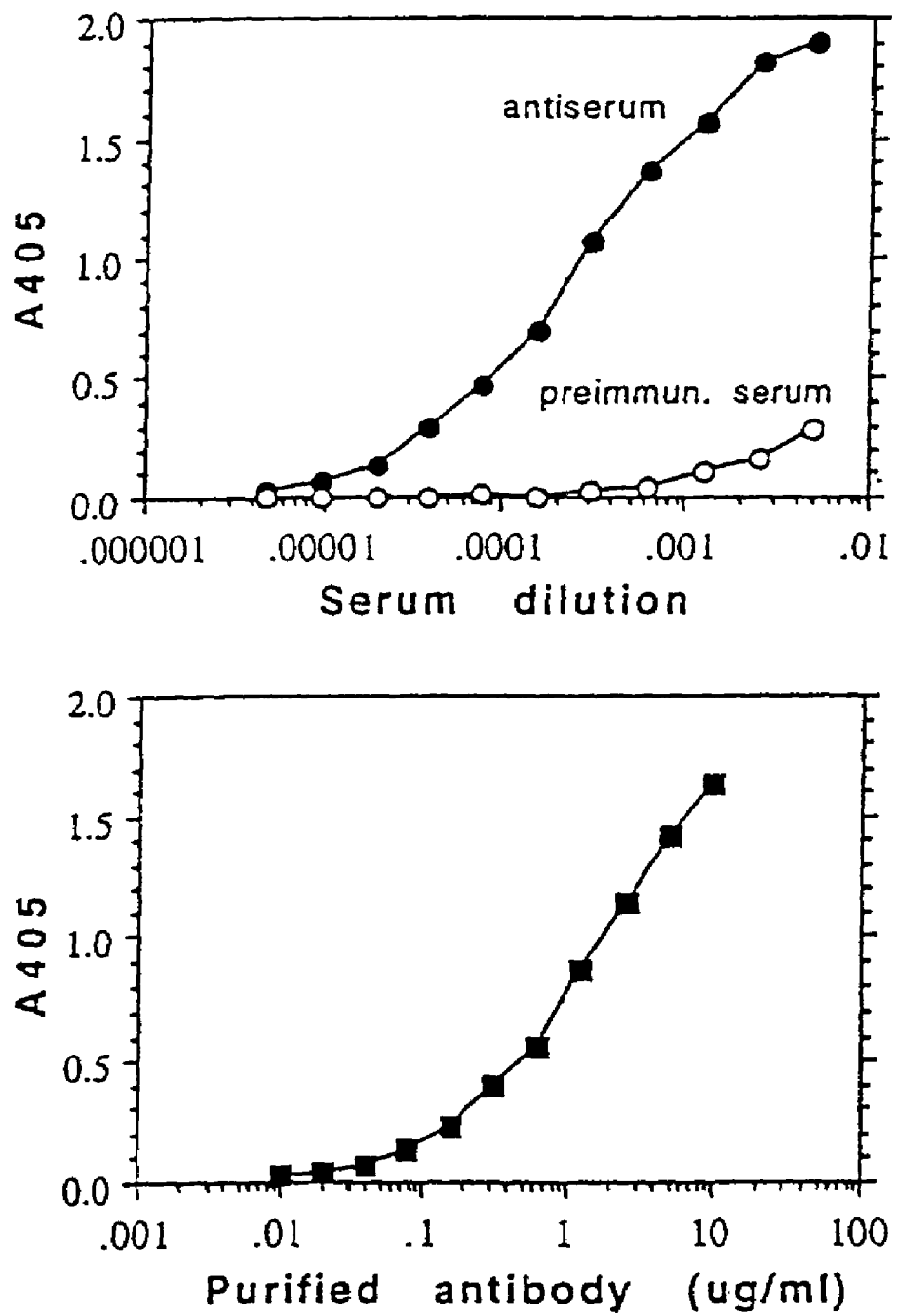

The peptide corresponding to the N-terminal sequence of the 8 kDa fragment (Acetyl-FFQHRIHVFSIFNHC) (SEQ ID NO: 21) was coupled to KLH and the conjugate was used to raise antibody with high titer. The antibody response was observed at $2 \times 10^{-5}$ dilution of antiserum and 0.08 µg/ml of affinity purified antibody (α8-antibody) as assessed by ELISA against free peptide without conjugation to KLH (FIG. 7)

Figure 8:
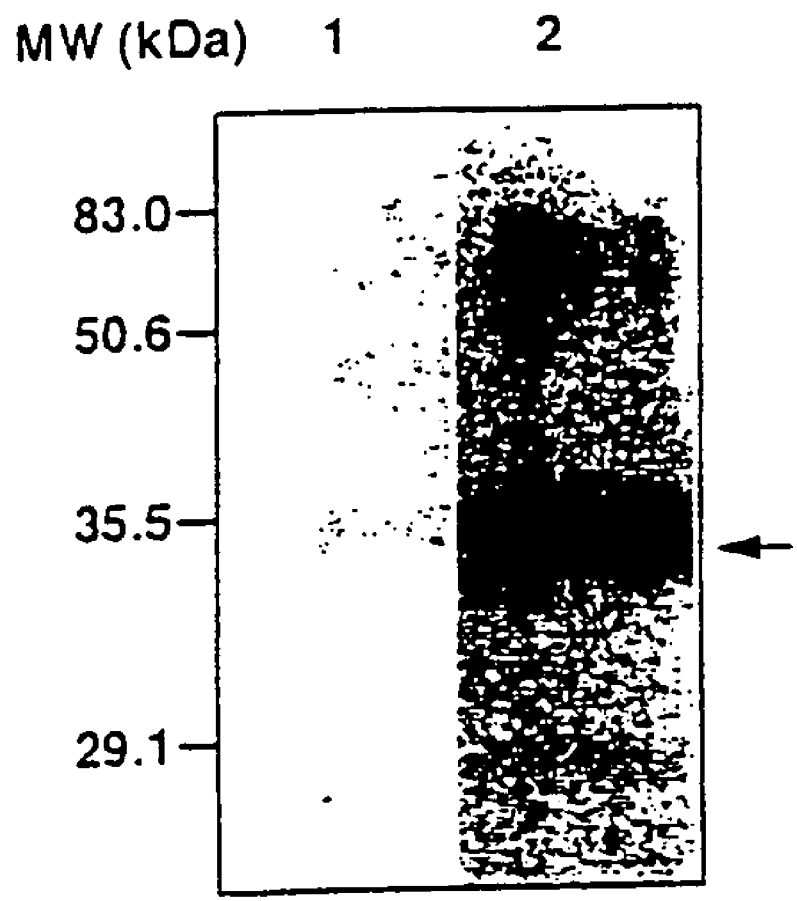

The synthetic peptide corresponding to the 8 kDa-fragment was hydro-phobic and could not be dissolved in a buffer without dimethyl sulfoxide. Initially, the labeled 34 kDa protein, extracted from preparative SDS-PAGE gels., was used after removing SDS, but no labeled protein was immunoprecipitated. After solubilization of the photoaffinity-labeled membranes by n-octylglucoside followed by denaturation with urea, the α8-antibody immunoprecipitated the labeled 34 kDa SMBP (FIG. 8).

Figure 9:
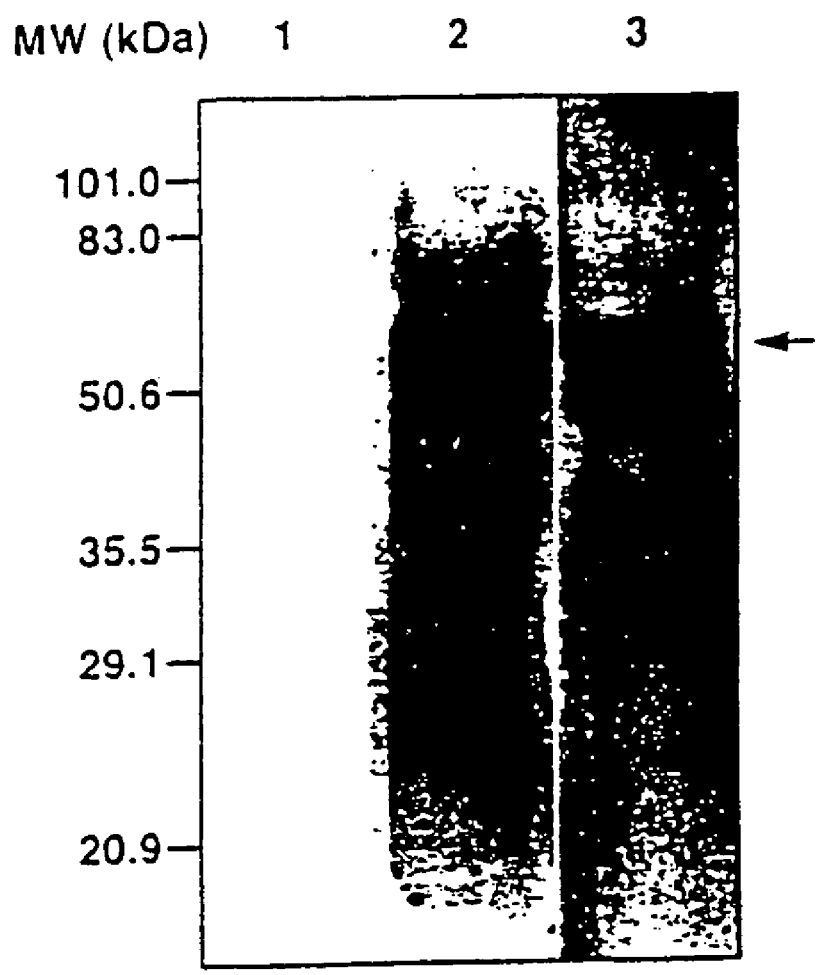

The α8-antibody recognized only a 70 kDa band by western blotting. The specificity of the antibody was demonstrated by the ability of the free peptide to inhibit the binding of the antibody to the 70 kDa protein (FIG. 9). In a separate experiment, photoaffinity-labeled SMBP was purified by two-dimensional electrophoresis in preparative scale, and the 34 kDa labeled spot in gels was isolated, extracted and subjected to SDS-PAGE. Two labeled bands of 34 and 70 kDa derived from 34 kDa were observed, indicating that the 70 kDa protein could be dimer.

EXAMPLE 2

Pharmacological Properties of the Rat Receptor According to Example 1

Catecholamine-induced relaxant responses which are resistant to blockade of α-, β1- and β2-adrenoceptors (ARs) have been described in a number of gastro-intestinal smooth muscle preparations, such as guinea pig ileum (Bond R. A. et al., 1988), rat proximal colon (Croci T. et al., 1988), rat distal colon (McLaughlin D. P. et al., 1990), rat gastric fundus (McLaughlin D. P. et al., 1991) and rat jejunum (Van der Vliet A. et al., 1990). Manara et al., 1990, actually reported that the phenylethanolamino-tetralines-stimulated rat colon relaxation paralleled rat adipocyte lipolysis, suggesting that this response predominantly involved the β3-AR.

1) Materials and Methods

Chemicals

SM-11044 ((L)-threo-3-(3,4-dihydroxyphenyl)-N-[3-(4-fluorophenyl) propyl]serine pyrrolidine amide hydrobromide), SM-14786 ((D)-threo isomer of SM-11044), SM-14011 ((DL)-threo-isomer of SM-11044), SM-14010 ((DL)-erythro-isomer of SM-11044), BRL-35135A ((R*R*)-(+)-4-[2'-[2-hydroxy 2-(3-chlorophenyl) ethyl amino]propyl]phenoxyacetic acid methyl ester), BRL-37344 (acid metabolite of BRL-35135A) and (($^{125}$I)-cyanopindolol were synthesised at Sumitomo Pharmaceuticals (Osaka, Japan). CGP-12177A and CGP-20712A were gifts from Ciba-Geigy Corporation (Basal, Switzerland). ICI-198157 ((RS)-4-[2-[(2-hydroxy-3-phenoxypropyl) amino]ethoxy]phenoxyacetic acid methyl ester), ICI-201651 (acid metabolite of ICI-198157) and ICI-215001 ((S)-isomer of ICI-201651) and ICI-118551 were obtained from Zeneca Pharmaceuticals (Macclesfield, England). SR-58611A ((RS)-N-(7 carbethoxymethoxyl-1,2, 3,4-tetrahydronaphth-2-yl)-2-hydroxy-2-(3 chlorophenyl) ethanamine hydro-chloride) was a gift from Sanofi-Midy (Milano, Italy). (+)-Carazolol was obtained from Boehringer Mannheim (Mannheim, Germany). (+)-Bupranolol was a gift from Schwarz Pharma (Monheim, Germany). (−)-3-[$^{125}$I]iodocyanopindolol ([$^{125}$I]-ICYP) and (+)-3 [$^{125}$I]-iodocyanopindolol-diazirine ([$^{125}$I]-ICYP-diazirine) were purchased from Amersham (Buckinghamshire, England). All other drugs were purchased from Sigma Chemical Co. (St. Louis, Mo., USA).

Relaxation of Rat Colon

Rat colon segment (2 cm) was suspended in organ bath containing 10 ml modified-Tyrode solution (Sugasawa T. et al. Eur. J. Pharmacol., 1992, 216, 207-215). The Tyrode solution contained 0.5 µM atropine, 0.5 µM desmethylimipramine, 30 µM hydrocortisone, 30 µM ascorbic acid, 10 µM phentolamine and 1 µM propranolol throughout study, in order to inhibit spontaneous contraction, neuronal and extraneuronal uptake of norepinephrine, oxidation of catecholamines, possible α, β1- and β2-AR effects, respectively.

The relaxant action of agonists was determined by measuring relaxation of KCl (100 mM)-induced tonus evoked by cumulative addition of the agonists as described previously (Sugasawa T. et al. cited above). In the case of testing the effect of cyanopindolol, it was added 5-10 min before the addition of agonist.

Lipolysis in Rat White Adipocytes

White adipocytes were isolated from epididymal fat pads of male Wistar rats (190-230 g) and lipolysis was determined according to the previous report (Sugasawa T. et al. cited above). The cells were preincubated for 5 min at 37° C. in the presence of 30 μM ascorbic acid, 10 μM phentolamine and 1 μM propranolol.

Agonists were then applied and incubated for 90 min. In the case of testing the effect of cyanopindolol, it was added 5 min before the addition of agonist.

Schild Plot

Agonist concentration-ratios (CR) were determined from the $EC_{50}$ values of the concentration-response curves of agonists with or without cyanopindolol, according to the method of Arunlakshana et al., 1959.

Linear regression analysis was used to estimate the $pA_2$ value and slope of the line, after confirming that the regression was linear and the slope was not significantly different from unity (Cochran-cox test, p>0.05). The $EC_{50}$ values were calculated using the computer program, InPlot™.

Statistical Analysis

Results are expressed as mean±SEM. Statistical significance between two data sets was examined by Student's t-test or Cochran-cox test, depending on the homogeneity of the variances. Duncan's multiple range test was used for multiple data sets. A probability level of p<0.05 was considered to be significant.

Membrane Preparation

Membranes from the colon smooth muscle and from skeletal muscle were prepared from male Wistar rats (300-360 g) as essentially mentioned in example 1.

Binding Assays in Membranes

Saturation binding studies were performed in a final volume of 200 μl of Tris-saline containing 50 μg membrane proteins and different concentrations (0.05-25 nm) of $[^{125}I]$-ICYP, supplemented with 10 μM serotonine (5-HT), 10 μM phentolamine, 20 μM propranolol and 1.1 mM ascorbic acid (pH 7.4), to block possible 5-HT receptors, ARs and oxidation of catecholamines, respectively. The $[^{125}I]$-ICYP was used after removing methyl alcohol by compressed air to avoid the influence of the solvent. Incubations were carried out at 37° C. for 30 min in a shaking water-bath incubator and terminated by addition of 4 ml of ice-cold Tris-saline followed by rapid filtration under vacuum on Whatman GF/B filter presoaked in Tris-saline containing 0.1% polyethyleneimine (pH 7.4). The filters were washed three times with 4 ml of ice-cold Tris-saline, transferred to plastic tubes and counted in a γ-counter.

Competition assays were performed against 1 nM $[^{125}I]$-ICYP. Non-specific binding was determined in the presence of 100 μM SM-11044. The inhibition constant, Ki, of a ligand was calculated using the equation described by Cheng and Prusoff (Biochem. Pharmacol., 1973, 22, 3099-3108). Hill coefficient was calculated by linear regression using saturation experiment data. Pseudo-Hill coefficient and $IC_{50}$ were determined by the computer program, InPlot™ (GraphPad Software, CA, USA).

Photoaffinity Labeling of the Membranes

Photoaffinity labeling was performed in a final volume of 1 ml of Tris-saline containing 0.5 mg membranes, 1.5 nM $[^{125}I]$-ICYP-diazirine, supplemented with 10 μM 5-HT, 10 μM phentolamine, 20 μM propranolol and 1.1 mM ascorbic acid (pH 7.4). Incubations were carried out in the presence or absence of competitor at 37° C. for 45 min in the dark in a shaking water-bath incubator and terminated by addition of 10 ml of ice-cold Tris-saline followed by a rapid centrifugation (150,000×g for 10 min at 4° C.). The membranes were irradiated with a UV lamp for 5 min with cooling by circulating water. The labeled membranes were diluted with 10 ml of ice-cold Tris-saline, centrifuged (150,000×g for 30 min at 4° C.), and the pellet was resuspended in Tris-saline and kept at −80° C.

SDS-PAGE

SDS-PAGE was performed under reducing conditions essentially as described by Laemmli, 1970, using 12% polyacrylamide gels (40% T, 2.6% C). The photoaffinity-labelled membranes were incubated in SDS-sample buffer (5% SDS, 1% 2β-mercaptoethanol, 10% glycerol, 0.002% bromophenol blue, 50 mM Tris/HCl, (pH 6.8)) for at least 1 h at room temperature. After electrophoresis, the gels were dried and autoradiographed on X-OMAT™ AR film (Eastman Kodak Co., NY, USA), as specified in example 1, chapter <<(preparative SDS-PAGE>>.

Two-Dimensional PAGE of Photoaffinity-Labeled Membranes

Photoaffinity-labeled membranes in the presence of 10 μM 5-HT, 10 μM phentolamine and 20 μM propranolol were solubilized in IEF-sample buffer (8 M urea, 0.3% SDS, 5.6% Triton X-100, 2.8% 2β-mercaptethanol, 1.1% Bio-Lyte ⅝ ampholyte and 0.6% Bio-Lyte 8/10 ampholyte (Bio-Rad)) and 30 μg of membrane proteins were submitted to IEF electrophoresis in a 5-10 pI range of 4% polyacrylamide tube gels containing 2.0% Bio-Lyte ⅝ ampholyte, 1.0% Bio-Lyte 8/10 ampholyte, 8 M urea and 2% Triton X-100. The second dimension was conducted on SDS-PAGE of 9% polyacrylamide gels. The gels were then dried and submitted to autoradiography as described above.

Cleavage by Endoglycosidase or N-Glycopeptidase F

Photoaffinity-labeled membranes in the presence of 10 μM 5-HT, 10 μM phentolamine and 20 μM propranolol were treated with N glycopeptidase F (PNGase F, EC 3.2.2.18) or endoglycosidase (Endo Hf, EC 3.2.1.96), using kits according to the manufacturer's specifications (New England Bio-Labs, MA, USA). Briefly, the membranes were solubilized in 0.5% SDS and 1% 2β-mercaptethanol, and 40 μg of membrane proteins were incubated with 5000 units of PNGase F in the presence of 1% NP-40 or with 2000 units of Endo Hf for 3 h at 37° C. The digested samples were subjected to SDS-PAGE of 12% polyacrylamide gels. The gels were then dried and submitted to autoradiography as described above.

Wheat Germ Agglutinine (WGA)—Sepharose Chromatography

Photoaffinity-labeled membranes in the presence of 10 μM 5-HT, 10 μM phentolamine and 20 μM propranolol were solubilized in 1% Triton X 100 in Tris-saline at 4° C. for 16 h. The solubilized material was collected after centrifugation (200,000×g for 1 h at 4° C.) and diluted to 0.1% Triton X-100 by Tris-saline. One milliliter gel bed volume of WGA-sepharose 6 MB (Sigma) was washed and equilibrated with 30 ml of 0.1% Triton X-100 in Tris-saline (buffer A), and 1 ml of solubilized material containing 200 μg membrane proteins was loaded at room temperature. The unretained fraction was recycled three times. After washing with 10 ml of buffer A, the bound material was eluted with 5 ml of 300 nM N-acetyl-D-glucosamine (Merck) in buffer A. The fractions were subjected to SDS-PAGE of 12% polyacrylamide gels. The gels were then dried and submitted to autoradiography as described above.

Tryptic Cleavage

The photoaffinity-labeled membranes were subjected to SDS-PAGE of 12% polyacrylamide gels. The gels were then dried and submitted to autoradiography as described above. The radioactive band at 34 kDa was excised, immersed in distilled water and minced to small pieces (2 mm width×2 mm height). The isolated gel pieces corresponding to 800 µg membrane proteins was digested in 500 µl of 100 mM Tris/HCl (pH 8.0) containing 0.1% SDS and 50 µg trypsin (EC 3.4.21.4, Type IX from Porcine Pancreas, Sigma) for 24 h at 37° C. according to the method of Kawasaki H. et al., 1990. After digestion, the supernatant was recovered and filtrated using a SPIN-X filter (0.45 mm pore size, Costar, MA, USA). The gel pieces were crushed through a nylon mesh (200 mesh) by centrifugation for 10 min at 14,000×g. A 2-fold volume of 100 mM Tris/HCl containing 0.1% SDS was added to the crushed gels, and a second extraction was performed by incubation for 2 h at 37° C. with rotating. After incubation, the supernatants were recovered by SPIN-X filter. The two extracts were combined, vacuum concentrated and submitted to Tricine-SDS-PAGE.

Chemical Cleavage

The 34 kDa photoaffinity-labeled protein was isolated by SDS-PAGE and extracted with 100 mM Tris/HCl (pH 8.0) containing 0.1% SDS as described above. The extracts were combined and concentrated by Centricon 10 (Amicon. MA, USA) and washed twice by distilled water. The extracts were lyophilised by vacuum concentrator and treated with 200 µl of 70% formic acid or 1% CNBr/70% formic acid for 24 h at room temperature, or 70% formic acid for 72 h at 37° C. in the dark. The cleaved products were diluted with 500 gi distilled water and lyophilised. This washing procedure was repeated three times. The cleaved products were separated by Tricine SDS-PAGE.

Tricine-SDS-PAGE

Tryptic and chemical cleaved fragments were separated on a Tricine gel system under reducing conditions (Schagger H. et al., 1987) using 18% polyacrylamide separating gel containing 10.7% glycerol. After electrophoresis, the gels were stained with 0.25% Coomassie brilliant blue R-250 (Sigma) in 40% methanol and 10% acetic acid, and destained in 10% acetic acid. The gels were then dried and submitted to autoradiography as described above.

2) Results

Functional Studies in Rat Colon and White Adipocytes

Under blockade of $\alpha$-, $\beta$1- and $\beta$2-ARs (in the presence of 10 µM phentolamine and 1 µM propranolol), a number of 1-AR agonists relaxed KCl-induced tonus in rat colon smooth muscle segment, giving a rank order of potency of BRL-37344>SM-11044>>isoproterenol >>norepinephrine= epinephrine (Table 1).

TABLE 1

Agonist efficiency in rat colon relaxation and rat white adipocyte lipolysis in the presence of 10 µM phentolamine and 1 µM propranolol

| | Rat colon | | | Rat white/adipocytes | | |
|---|---|---|---|---|---|---|
| Agonist | $pD_2$ | IA | n | $pD_2$ | IA | n |
| (−)-isoproterenol | 6.64 ± 0.22 | 1.00 ± 0.063 | 5 | 5.86 ± 0.07 | 1.00 ± 0.037 | 5 |
| (−)-norepinephrine | 5.85 ± 0.27 | 0.85 ± 0.168 | 4 | 5.40 ± 0.10 | 1.02 ± 0.058 | 5 |
| (−)-epinephrine | 5.92 ± 0.06 | 0.86 ± 0.137 | 6 | 5.16 ± 0.06 | 0.91 ± 0.036 | 5 |
| BRL-37344 | 7.50 ± 0.18 | 1.00 ± 0.126 | 8 | 7.25 ± 0.09 | 0.72 ± 0.0333** | 5 |
| SM-11044 | 7.29 ± 0.21 | 1.48 ± 0.166* | 7 | 5.96 ± 0.11 | 0.86 ± 0.054 | 5 |

Statistical significance between IA values; * $p < 0.05$, ** $p < 0.01$ vs isoproterenol (Duncan's multiple range test).

Figure 10:
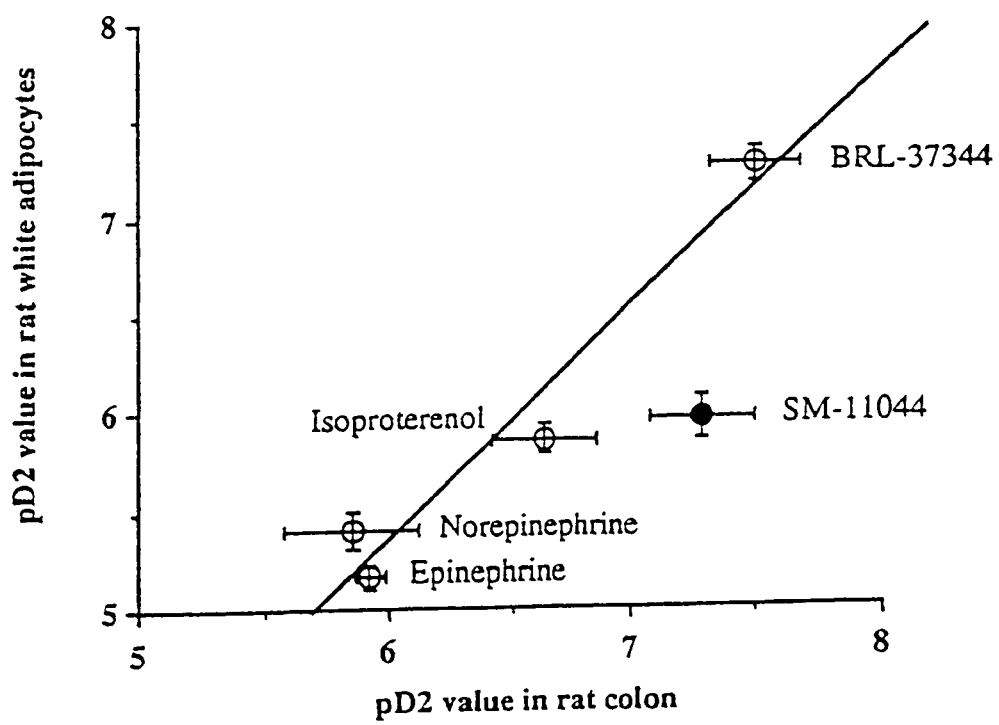

The IA value of SM-11044 was significantly higher than that of isoproterenol (Duncan's multiple range test, $p<0.05$), indicating different modes of action. In rat white adipocytes, the same agonists stimulated lipolysis with a rank order of potency of BRL-37344>>SM-11044=isoproterenol >norepinephrine >epinephrine (Table 1). The linear regression line for isoproterenol, norepinephrine, epinephrine and BRL-37344 reveals a significant correlation ($r=0.97$, $p<0.05$) between agonist induced rat colon relaxation and adipocyte lipolysis (FIG. 10), suggesting that both effects predominantly involve the same atypical $\beta$-, that is $\beta$3-AR stimulation. In contrast to the four ligands, SM-11044 stimulated colon relaxation more efficiently than adipocyte lipolysis (FIG. 10). Indeed, the correlation coefficient ceased to be significant when linear regression was analyzed with all agonists including SM-11044 ($r=0.87$, $p>0.05$). These data suggest that SM-11044 acts on $\beta$3-AR and additional functional site that mediates relaxation in rat colon. Antagonism of cyanopindolol for SM-11044 and for isoproterenol was compared in both preparations. Cyanopindolol itself, up to the concentration of 10 µM used here, had no effect on the degree of tonus induced by KCl in rat colon and did not stimulate lipolysis in rat white adipocytes. Cyanopindolol antagonised agonist-induced rat colon relaxation in a concentration-dependent manner, with $pA_2$ values for SM-11044 of 8.31 (slope=0.78) and for isoproterenol of 7.65 (slope=1.03) (Table 2).

TABLE 2 pA$_2$ values for cyanopindolol in rat colon and rat white adipocytes in the presence of 10 μM phentolamine and 1 μM propranolol.

| Agonist | Rat colon | | | Rat white adipocytes | | |
|---|---|---|---|---|---|---|
| | pA$_2$ | Slope | n | pA$_2$ | Slope | n |
| (−)-isoproterenol | 7.65 ± 0.48 | 1.03 ± 0.08 | 5 | 7.44 ± 0.61 | 1.08 ± 0.10 | 4 |
| SM-11044 | 8.31 ± 0.88 | 0.78 ± 0.11 | 5 | 7.32 ± 1.51 | 0.96 ± 0.21 | 4 |

Cyanopindolol also antagonized agonist-induced rat white adipocyte lipolysis in a concentration-dependent manner, with pA$_2$ values for SM 11044 of 7.32 (slope=0.96) and for isoproterenol of 7.44 (slope=1.08) (Table 2). The similar pA$_2$ values for isoproterenol in colon (7.65), SM-11044 in adipocytes (7.32) and isoproterenol in adipocytes (7.44) with the slopes close to unity, indicating the competitive antagonism of cyanopindolol for both agonists binding to β3-AR. All slopes of Schild plots were not significantly different from unity. However, only the slope for SM-11044 in rat colon (0.78) seemed to be lower than unity with high pA2 value (8.31), suggesting that SM-11044 and cyanopindolol compete not only binding to β3-AR but also to additional functional site on rat colon.

Binding Assays in Rat Colon Membranes

Figure 11:
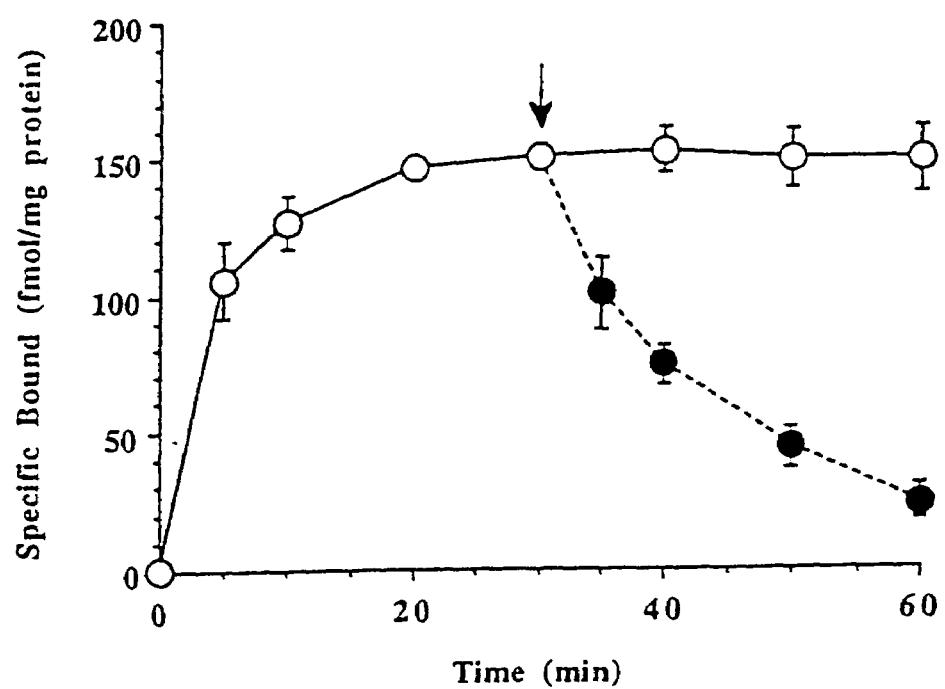
Figure 12:
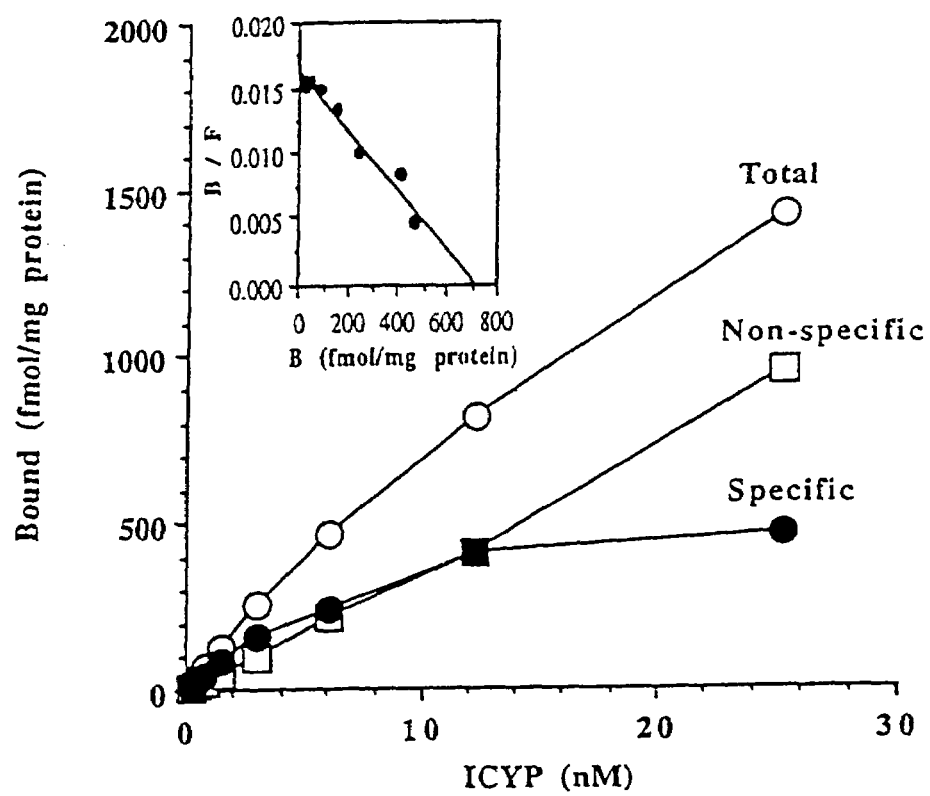

In order to identify the predicted functional site, being competed by SM-11044 and cyanopindolol, binding studies in rat colon smooth muscle membranes were performed using [$^{125}$I]-ICYP for radioligand and SM-11044 for non-specific binding determination, under blockade of serotonine, α-, β1-, β2- and also β3-adrenergic receptors (in the presence of 10 μM 5-HT, 10 μM phentolamine and 20 μM propranolol). The time course of specific binding of [$^{125}$I]-ICYP (1 nM) to rat colon membranes was illustrated in FIG. 11. Specific binding achieved equilibrium levels at 30 min (82.7±1.9%, n=2), and was reversed by addition of SM-11044. The results of a saturation experiment with increasing amount of [$^{125}$I]-ICYP, carried out at equilibrium (30 min incubation), are illustrated in FIG. 12. Scatchard plot analysis revealed a single class of binding sites with a dissociation constant (Kd) of 11.0±0.95 nM, and a maximum number of binding sites (Bmax) of 716.7±21.12 fmol/mg protein (r=−0.978, p<0.001). Hill plot analysis of the saturation curve yielded a coefficient of 0.99±0.03 (r=0.998, p<0.0001), indicating the absence of cooperativity.

Figure 13:
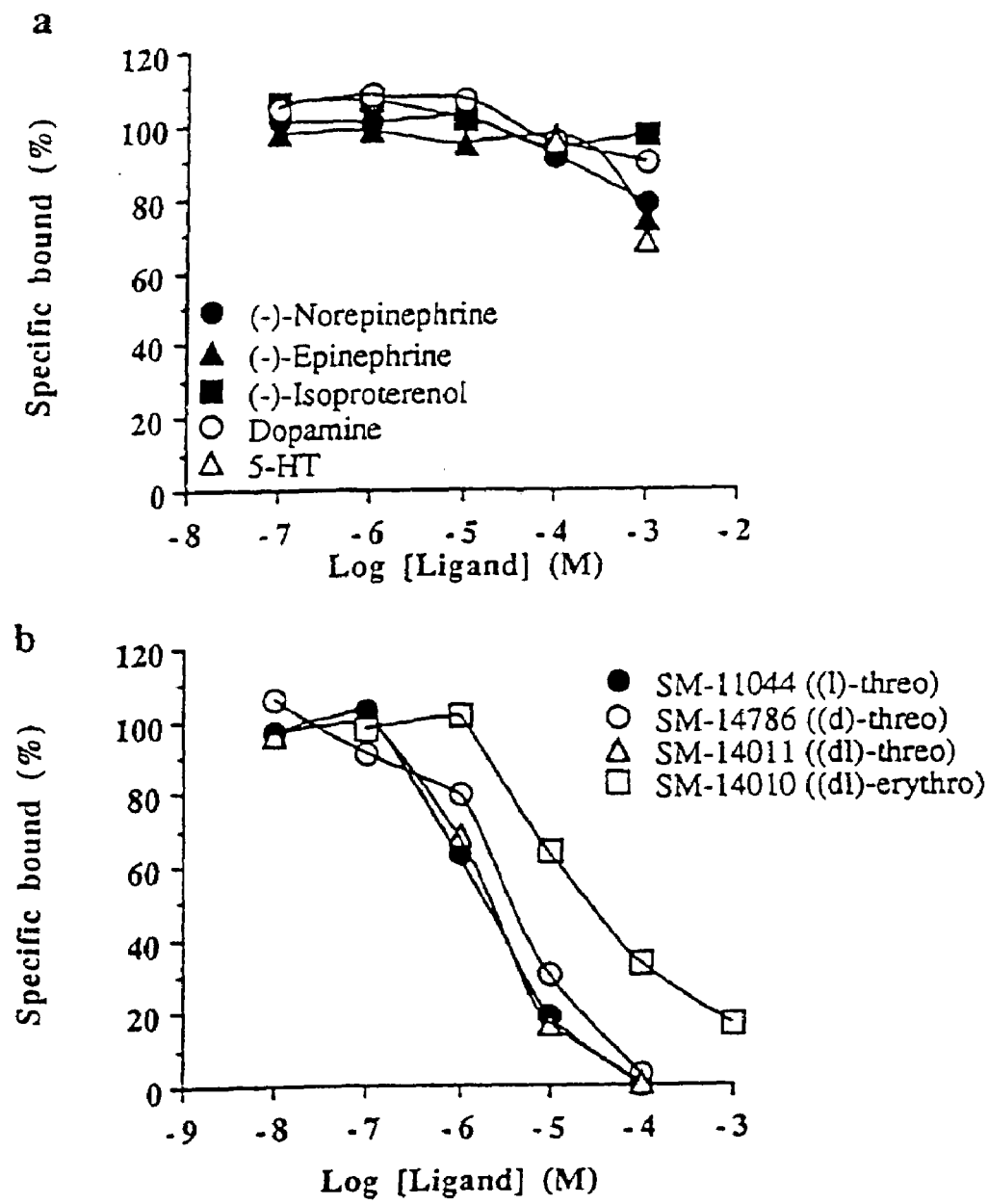

In competition binding studies, specific binding was not displaced by isoproterenol, norepinephrine, epinephrine, dopamine nor 5-HT, up to the concentration of 1 mM (FIG. 13a, Table 1). The competition binding by isomers of SM-11044 was stereo-selective, SM-14011 (the racemic threo isomer, Ki 2.0 μM) being 15 times more effective than SM-14010 (the racemic erythro-isomer, Ki 29.3 μM) (FIG. 13b, Table 3). The β1-AR antagonist, CGP20712A and the β3-AR agonist, BRL-37344 did not displace the specific binding up to the concentration of 100 μM; the β2-AR antagonist, ICI-118551 was effective with a relatively high Ki (28.5 μM) (Table 3). Cyanopindolol was the most effective competitor with a Ki of 0.11 μM, and pindolol had no effect up to the concentration of 100 μM. Carazolol, a ligand structurally related to cyanopindolol, was less effective, in spite of being more lipophilic (Table 3). Interestingly, BRL-35135A (methyl ester of BRL-37344) and ICI 198157 (methyl ester of ICI-201651; ICI-215001, a (S)-enantiometer of ICI-201651) displaced the specific binding, whereas the corresponding acid metabolites were inactive (Table 3). The specific binding was significantly reduced by GTP (29.8±2.7% inhibition at 300 μM (p<0.01) and 98.2+1.3% at 1 mM (p<0.001), n=2, respectively).

TABLE 3

Affinity (Ki) values of various ligands on [$^{125}$I]-ICYP specific binding to rat colon membranes in the presence of 10 μM 5-HT, 10 μM phentolamine and 20 μM propranolol

| Ligands | Ki (μM) | Pseudo-Hill coefficient |
|---|---|---|
| Catecholamines and 5-HT | | |
| (−)-isoproterenol | >1000 | |
| (−)-norepinephrine | >1000 | |
| (−)-epinephrinllle | >1000 | |
| Dopamine | >1000 | |
| 5-HT | >1000 | |
| SM-11044 and stereo-isomers | | |
| SM-11044 ((l)-threo) | 1.8 ± 0.3 | 1.00 ± 0.12 |
| SM-14786 ((d)-threo) | 3.7 ± 0.4 | 0.92 ± 0.15 |
| SM-14011 ((dl)-threo) | 2.0 ± 0.5 | 1.07 ± 0.15 |
| SM-14010 ((dl)-erythro) | 29.3 ± 10.3 | 0.67 ± 0.13 |
| β1-antagonist | | |
| CGP-20712A | >100 | |
| β2-antagonist | | |
| ICI-118551 | 28.5 ± 3.6 | 0.89 ± 0.14 |
| β3-agonists | | |
| BRL-35135A (ester) | 1.4 ± 0.1 | 0.80 ± 0.14 |
| BRL-37344 (acid metabolite) | >100 | |
| ICI-198157 (ester) | 29.4 ± 8.9 | 0.96 ± 0.23 |
| ICI-215001 (acid metabolite) | >100 | |
| ICI-201651 (acid metabolite) | >100 | |
| SR-58611A (ester) | 5.9 ± 1.0 | 1.21 ± 0.21 |
| β1-, β2-antagonists having β3-partial agonist potencies | | |
| CGP-12177A | >100 | |
| (±)-cyanopindolol | 0.11 ± 0.02 | 1.01 ± 0.14 |
| (±)-pindolol | >100 | |
| (±)-carazolol | 8.1 ± 1.7 | 0.77 ± 0.11 |
| (±)-alprenolol | 13.3 ± 2.4 | 0.85 ± 0.24 |
| β1-, β2-, β3-antagonist | | |
| (±)-bupranolol | 11.3 ± 0.8 | 1.08 ± 0.08 |

Photoaffinity Labeling Study

Figure 14:
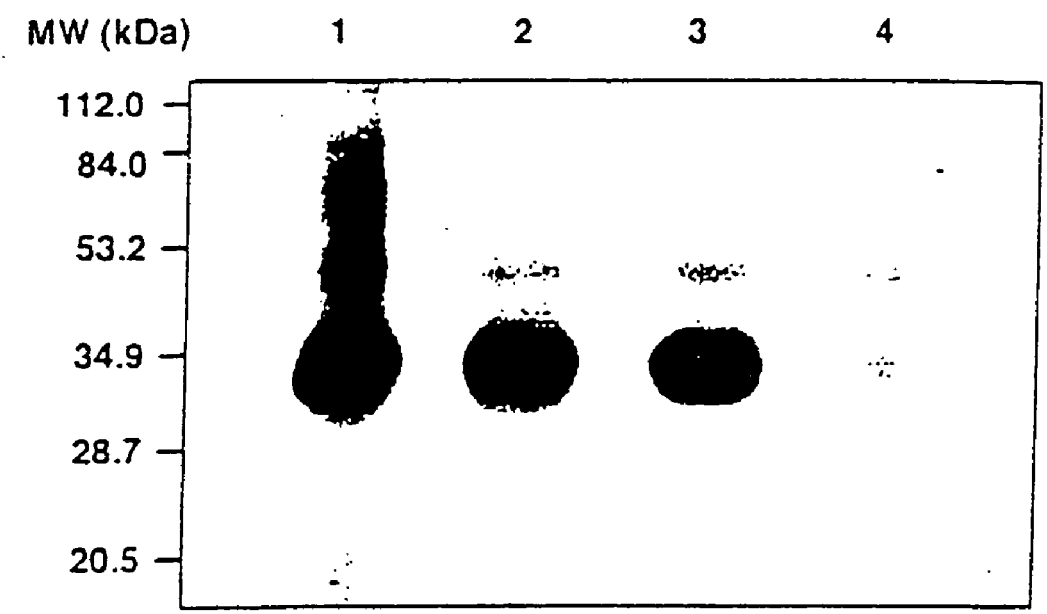

Photoaffinity labeling was performed to visualize the specific binding site in rat colon membranes using [$^{125}$I]-ICYP-diazirine. In the presence of 10 μM 5-HT and 10 μM phentolamine, but in the absence of propranolol, a single dense band of 34 kDa was visualized in addition to two broad-bands with apparent molecular masses of 50 and 70 kDa. (FIG. 14, lane 1). In contrast, in the presence of 20 μM propranolol, 10 μM 5-HT and 10 μM phentolamine, that is, in the same conditions of the competition binding assay with

[$^{125}$I] ICYP, only the 34 kDa band remained visible (FIG. 14, lane 2). These results suggest that the two broad bands are β-ARs. Moreover, the 34 kDa band was not displaced by 100 μM BRL-37344, but was displaced by 100 μM SM-11044 (FIG. 14, lanes 3 and 4, respectively). These data support the results of the competition binding assay, suggesting the existence of a single specific binding site for [$^{125}$I]-ICYP and SM-11044.

Figure 15:
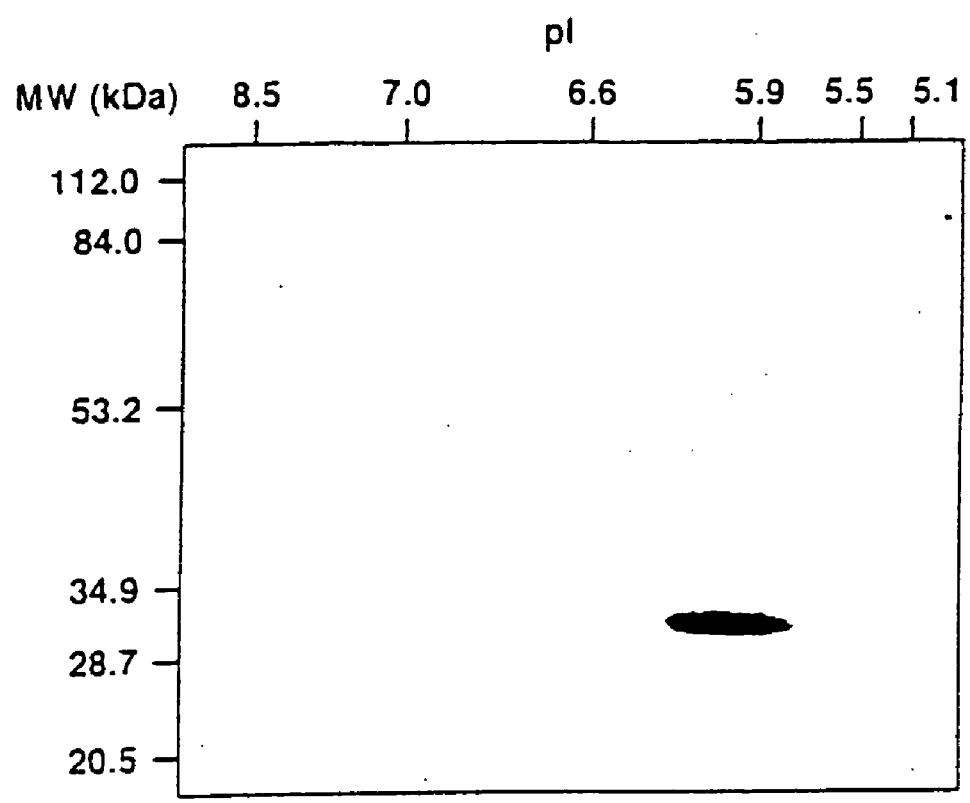
Figure 16:
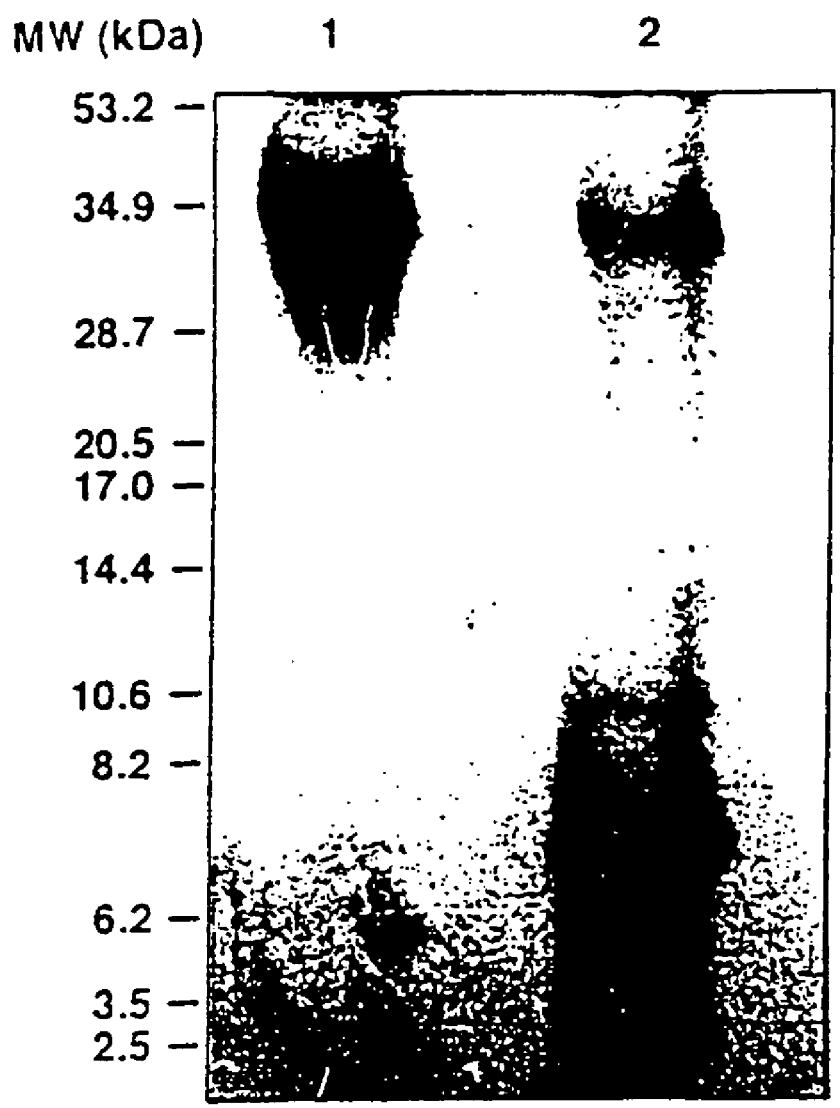

Two-dimensional PAGE of the photoaffinity-labeled membranes confirmed the labeling of a single 34 kDa polypeptide chain corresponding to a pI of 6.0 (FIG. 15). The molecular size of the photoaffinity-labeled 34 kDa protein was not modified by the enzymatic treatments with endoglycosidase or N glycopeptidase F, whereas both enzymes reduced the molecular size of ovalbumin from 43 kDa to 40kDa. Solubilized photoaffinity-labeled 34 kDa protein (373,298 cpm), were applied to a WGA-sepharose column. The unretained fraction contained 35.7% of the radioactivity, and washed out fractions contained 53.3% of the radioactivity. The specific sugar, 300 mM N-acetyl-D-glucosamine, eluted only 2.3% of the radiolabeled material. The eluted fraction was subjected to SDS-PAGE after concentration, but the photoaffinity-labeled 34 kDa band was not detected. A single 7 kDa labeled-peptide was generated upon digestion of the photoaffinity-labeled 34 kDa protein with trypsin (FIG. 16). Recovery yields in final extracts from the gel pieces were 62.7% for the labeled 34 kDa protein and 90.4% for the in-situ generated tryptic peptides.

Binding Studies in Rat Skeletal Muscle Membrane Preparation

Figure 17:
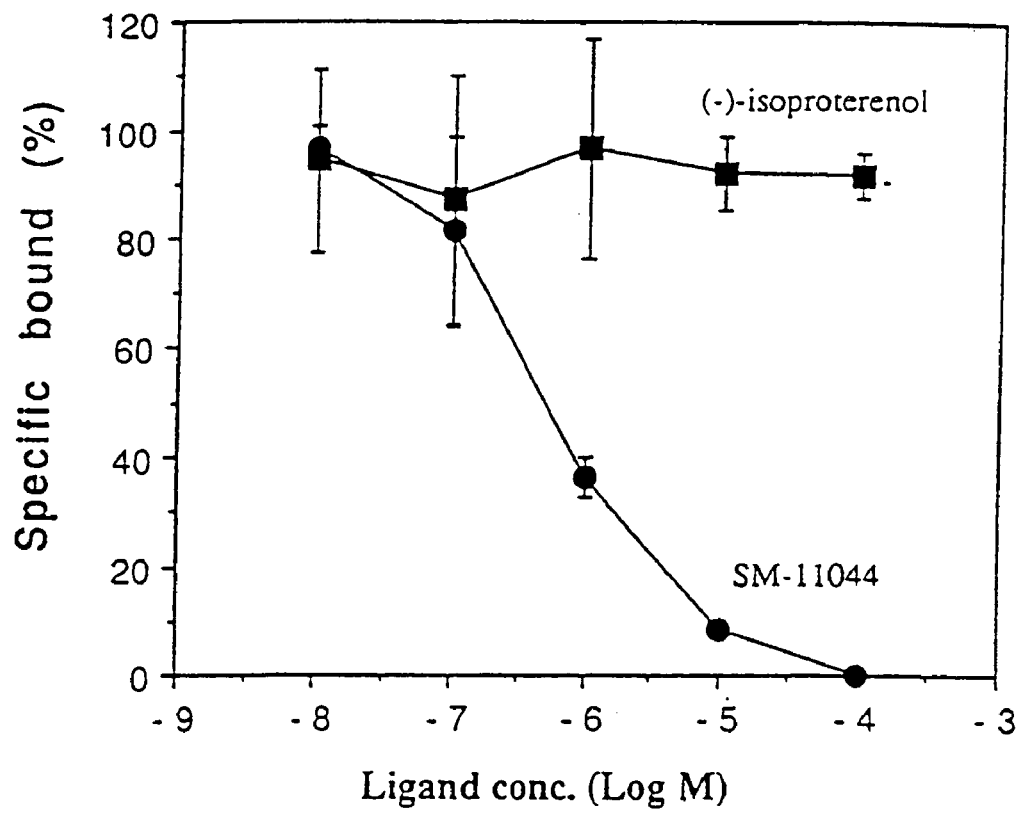

[$^{125}$I]-ICYP specific binding to skeletal muscle membranes was not displaced by isoproterenol up to concentrations of $10^{-4}$ M. In contrast, SM-11044 displaced the binding in a concentration-dependent manner (FIG. 17).

Pharmacological Definition of the Instant Receptor

SM-11044, a β-AR, agonist, showed atypical agonist effects such as relaxant responses in guinea pig ileum and rat colon intestines, and inhibition of guinea pig eosinophil chemotaxis.

Cyanopindolol competitively antagonized the responses to isoproterenol and SM-11044 at β3-AR with similar $pA_2$ values (7.32~7.65) in rat colon intestinal segments and rat white adipocytes. The values were also similar to those reported at β3-AR on rat white adipocytes (Kirkham D. et al., 1992), rat colon, rat gastric fundus (McLaughlin and MacDonald, 1989, 1990), and guinea pig ileum (Blue D. R. et al., 1989). In contrast, cyanopindolol antagonized the additional atypical effect of the SM-11044-induced colon relaxation with higher $pA_2$ value (8.31) along with low slope of Schild plots (0.78). The results demonstrated the existence of at least two different affinity sites including β3-AR in rat colon. Thus, cyanopindolol and SM-11044 competed not only at β3-AR but also at another atypical binding site. SM-11044 stimulated relaxant responses of the KCl-induced depolarized colon tonus through both sites.

Initial comparison with atypical effects between guinea pig ileum and rat white adipocytes could not exclude species-related difference. However, the difference of atypical effects between rat white adipocytes and rat colon intestines are now evident, that is not species-related phenomenon.

Detection of the binding site: radioligand binding assay was performed using rat colon smooth muscle membranes based on the results in functional studies that SM-11044 and cyanopindolol competed the sites. In general, if same origin of ligands are used for both radioligand and <<cold>> ligand, physically- or chemically-related non-specific binding can not be excluded.

Furthermore, $pA_2$ value of cyanopindolol was 8.31 and $pD_2$ value of SM-11044 was 7.29 in rat colon, suggesting 10-fold higher affinity of cyanopindolol pindolol than that of SM-11044 at the two atypical components (β3-AR and another site). Therefore, [$^{125}$I]-ICYP and SM-11044 were used as radioligand and <<cold>> ligand, respectively.

[$^{125}$I]-ICYP can bind to β1-, β2-, β3-ARs, serotonine 5-HT$_{1A}$ and 5-HT$_{1B}$-receptors (Tate K. M. et al., 1991; Hoyer D. et al., 1994). In contrast, specific binding was obtained under blockade of these known receptors. Competition binding studies revealed that the binding site was indeed different from these receptors. Natural AR ligands (epinephrine and norepinephrine) and classical β-AR ligand (isoproterenol) showed no affinity, suggesting that the binding site is different from ARs. Several synthetic β-AR ligands including β3-AR agonists (BRL-35135A, SR-58611A and ICI-198157) showed affinity. Atypical effects that could not be explained by β3-AR can be resolved by the existence of this binding site. Indeed, similar binding sites under blockade of β-ARs and serotonine receptors were observed in rat skeletal muscle membranes.

Biochemical Characterization by Photoaffinity-Labeling Study

The binding site in rat colon smooth muscle membranes was visualized by [$^{125}$I]-ICYP-diazirine, a photoaffinity ligand corresponding to [$^{125}$I]-ICYP. The apparent molecular size of the site was 34 kDa with an isoelectric point (pI) of 6.0. Deduced molecular sizes of rat β3-ARs, serotonine 5-HT$_{1A}$ and 5-HT$_{1B}$ receptors are 43.2-50.5 kDa (β1-AR, 50.5 kDa; β2-AR, 46.9 kDa; β3-AR, 43.2 kDa; 5-HT$_{1A}$, 46.4 kDa, 5-HT$_{1B}$, 43.2 kDa) (Machida et al., 1990; Gocayne et al., 1987; Muzzin P. et al., 1991; Granneman J G. et al., 1991; Albert A. et al., 1990; Fujiwara et al., 1990, Voigt et al., 1991). In cells or tissues, these receptors are normally glycosylated, then the sizes are usually bigger than the deduced sizes. In contrast, the size of 34 kDa seemed to be smaller than these cloned rat receptors. One explanation may be devoid of N-linked glycosylation. The isoelectric point indicates that the binding site is an acidic protein like β3-ARs (Fraser C. M., 1984). Chemical cleavage at mostly methionine residues resulted in 10 and 12 kDa, and acid cleavage at mainly asparagine-proline bonds resulted in 8 kDa, indicating this protein contains methionine residues and may include asparagine-proline bonds.

EXAMPLE 3

Isolation and Characterization of the Instant Receptor in Human Skeletal Muscle

Preparation of Probes:

SEQ ID NO: 6 has been compared to GenBank and EMBL data base by tblastn program (Altschul S. F. et al., 1990); in dbest data base, a human expressed sequence tag (EST) with almost 100% homology with SEQ ID NO: 6 was found; it corresponds to SEQ ID NO: 5, found in *H. sapiens* as a partial cDNA sequence, clone 72F05, translated in frame 1 in the form of SEQ ID NO: 5. However, it was not known whether or not said SEQ ID NO: 5 could have any biological function.

In view to obtain the instant non-adrenergic receptor including SEQ ID NO. 1 or NO. 14, plasmid DNA containing human clone designated 72FO5 (EMBL accession no. z28655) (Auffray C. et al., 1995), including the corresponding coding sequence of SEQ ID NO. 5 was obtained from Genethon, France and was used for preparing probes useful for hybridization assays.

900 bp probe (SEQ ID NO: 3):

Cutting said plasmid DNA with restriction endonuclease EcoRI (New England Biolabs ref 101 S) released a 0.9 kb insert corresponding to clone 72F05. This fragment was isolated using QiaEX II agarose gel extraction kit (Qiagen ref. 20021).

300 bp probe (SEQ ID NO: 4):

1) Design of sens and anti-sens primers for PCR:
sens primer: S4 (SEQ ID NO: 7)
anti-sens primer: S6 (SEQ ID NO: 8).

2) PCR on clone 72F05:

Amplification was performed on 1 ng of plasmid DNA corresponding to clone 72F05, in the presence of the following reagents: each primer at 0.25 µM; 10% DMSO; 2.5 U of Taq polymerase (Promega); 0.25 µM of dNTP (dATP; dCTP; dGTP; dTTP); reaction buffer was supplied by Promega and supplemented with 1.5 mM MgCl$_2$.

PCR was performed on Perkin Elmer <<Gene Amp PCR System 9600>>

| using the following conditions: | 4 min at 95° C. | |
|---|---|---|
| | 30 sec at 95° C. | |
| | 30 sec at 48° C. | 30 cycles |
| | 30 sec at 72° C. | |
| | 4 min at 72° C. | |

Under these conditions, a 0.3 kb fragment corresponding to the published sequence of clone 72F05 was amplified. The fragment was isolated using QiaEXII agarose gel extraction kit (Qiagen ref. 20021).

Radiolabeling of Probes:

By random priming (Feinberg et al., 1983) 50 µCi of dATP α32P (ICN ref 39010 X) were incorporated to radiolabel DNA fragments.

Northern Blot:

A human multiple tissue northern blot was purchased from Clontech (ref. 7765-1).

This blot ready to hybridize contained in each lane approximately 2 µg of polyadenylated mRNA from 8 different human muscles (smooth and striated):

lanes 1-8 in order: human skeletal muscle, uterus (no endometrium), colon (no mucosa), small intestine, bladder, heart, stomach, and prostate (see FIG. 18A).

The membrane was hybridized following the suppliers instructions with labeled 300 bp probe (SEQ ID NO: 4) (10$^6$ cpm/ml) during 24 hours.

Washes were carried out under different stringency:

1) low stringency: 2×SSC; 0.05% S.D.S. at room temperature.

Exposition of Amersham Hyperfilm MP at −80° C. for 3 days using two intensifying screens showed three different fragments: 2 major bands are present in all samples; one at 3.4 kb and one at 3.8 kb. One fainter band, around 7 kb is found in all samples.

2) high stringency: 0.1×SSC; 0.05% S.D.S. at 50° C.; same exposition showed the same fragments in all samples.

Figure 18:
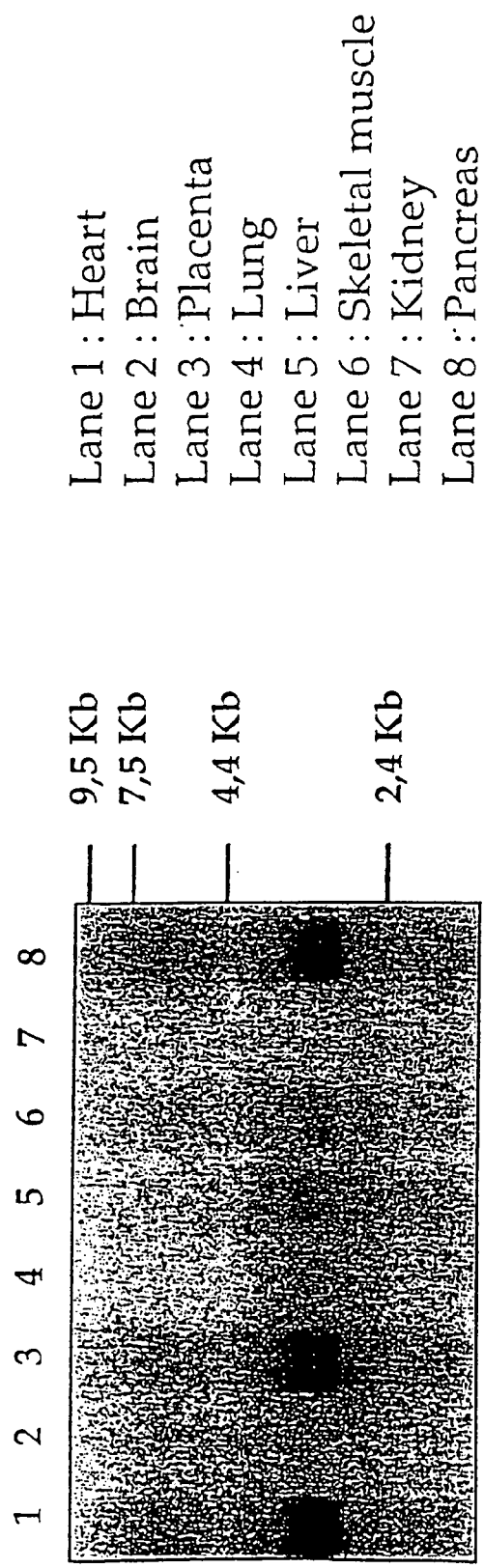
Figure 19:
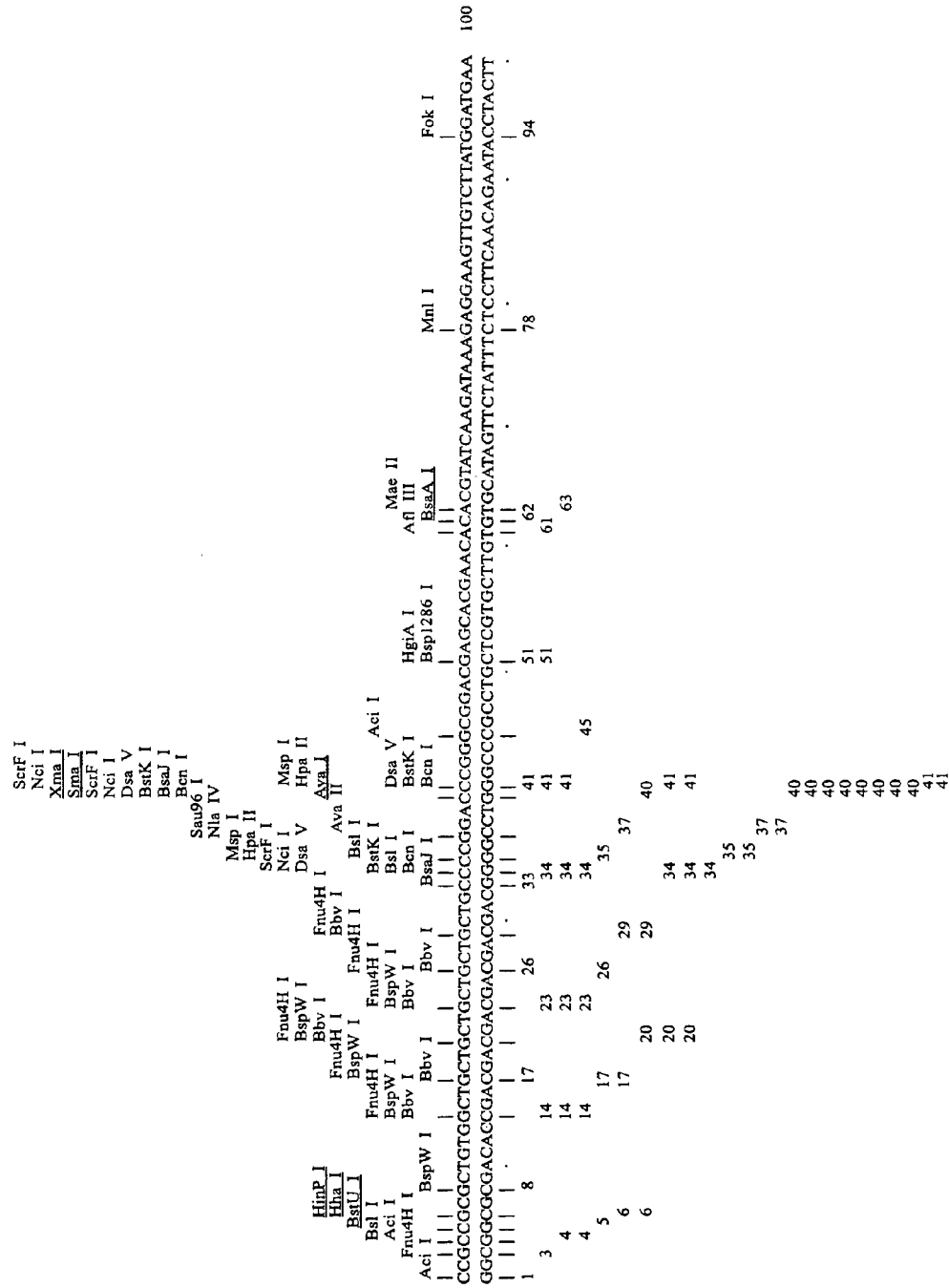
Figure 19:
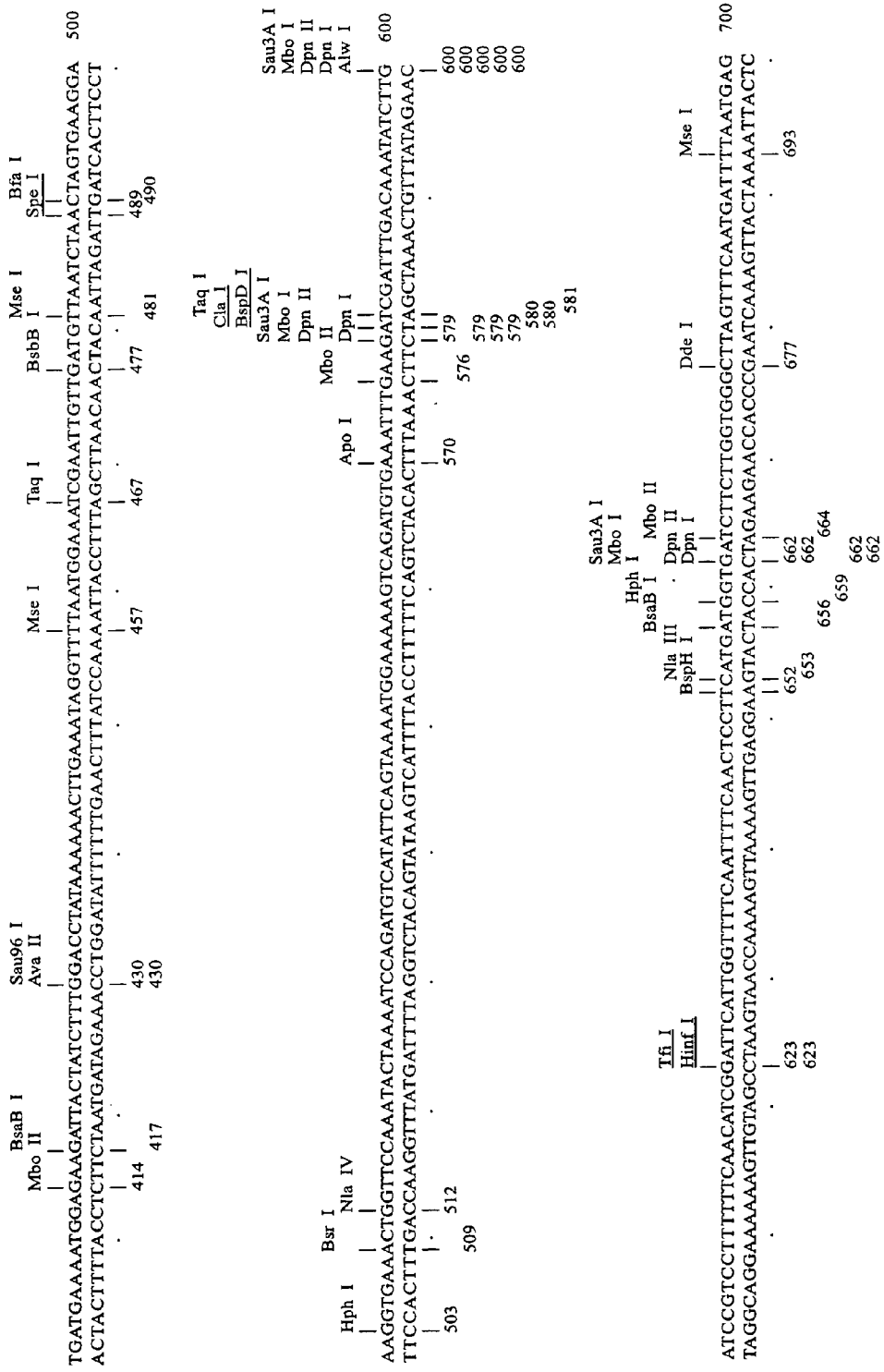
Figure 19:
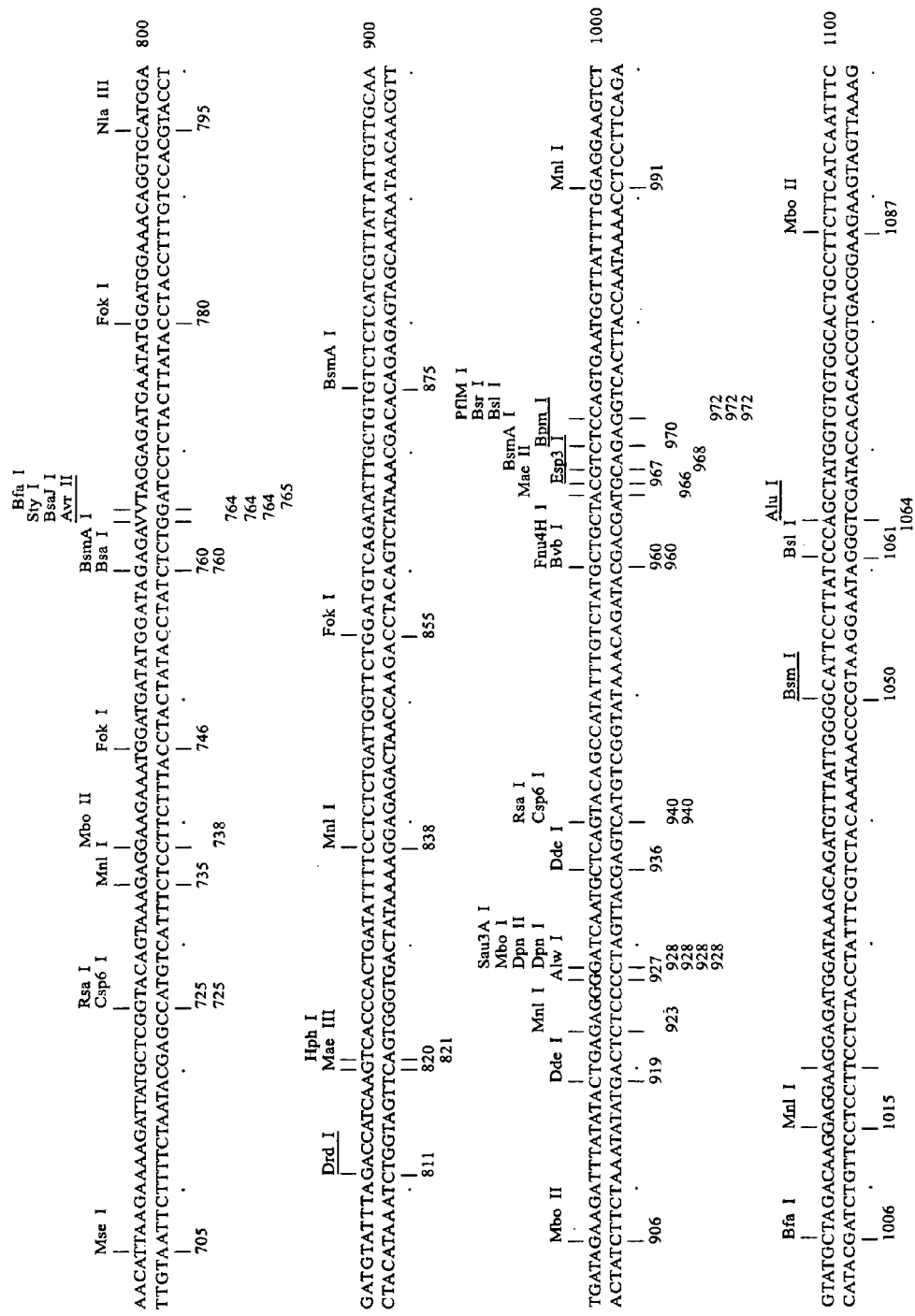
Figure 19:
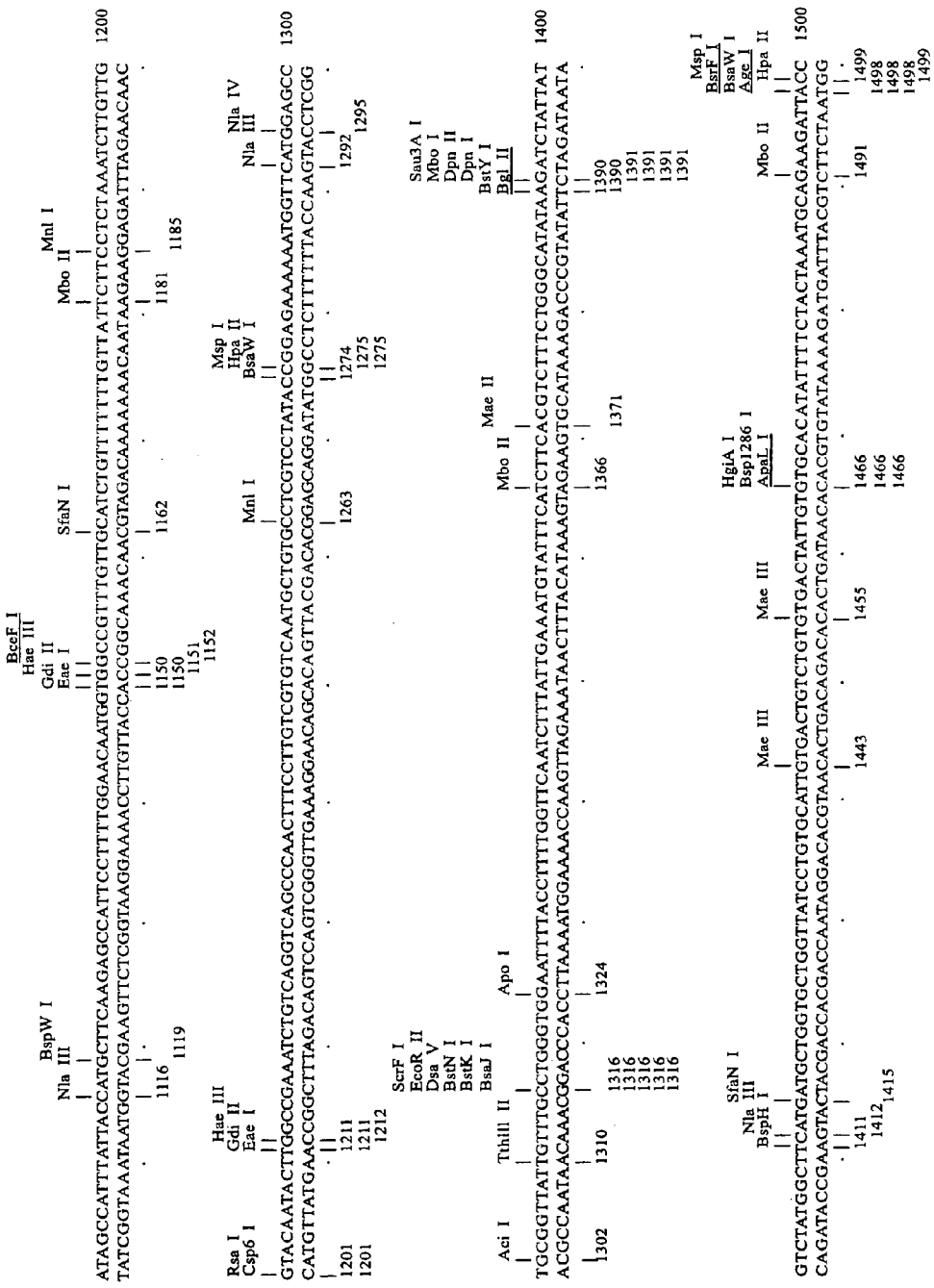
Figure 20:
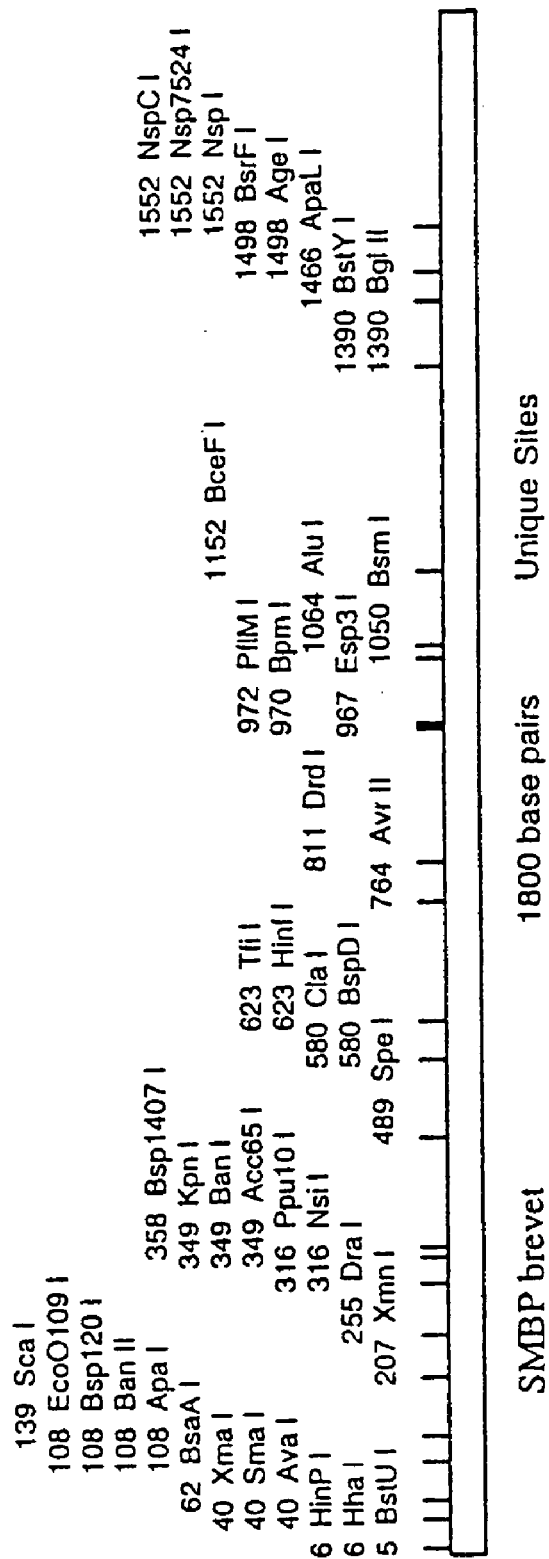

The results are illustrated in FIG. 18 (same results with low or high stringency).

The visualized mRNAs correspond to SMBP transcripts. One explanation for the presence of 3 different transcripts could possibly be the utilization of alternative polyadenylation sites on SMBP gene (Intervening Sequences in Evolution and Development; E. M. Stone and R. J. Schwartz Oxford University-Press 1990).

A similar analysis done with a variety of non muscular tissues (heart, brain, placenta, lung, liver, kidney and pancreas) confirmed these observations (FIG. 18B).

Cloning of Human cDNA:

A human skeletal muscle cDNA library was purchased from Clontech (ref HL 300s; lot 32288). 500,000 clones were transferred to nylon membranes (Hybond N+; Amersham) and screened by hybridizing either with probe 300 bp (SEQ ID NO: 4) or with probe 900 bp (SEQ ID NO: 3).

Hybridization Conditions were:

600 mM NaCl; 60 mM Na-citrate; 8 mM Tris-HCl pH 7,5; 50 mM Na-phosphate; 1% Ficoll; 1% polyvinylpyrrolidone; 1% bovine serum albumine; 40% form amide; 0.2% SDS; 50 µg/ml salmon sperm DNA.

Radiolabeled probe was added at 10$^6$ cpm/ml and incubated overnight at 42° C.

Final washes were at 50° C.; 0.1×SSC; 0.05% SDS for 1 hour.

11 positive clones were identified by repeated rounds of screening.

Insert sizes were analyzed by simultaneous cutting with the following restriction endonucleases: xba I/Hind III and Xba I/Bam HI (New England Biolabs). These enzymes released cDNA inserts from the vector pcDNA I (Invitrogen). All clones were sequenced with T7 and SP6 primers from both ends and found to be overlapping.

The longest cDNA insert (clones no 24 and no 15) was about 1.7 kb and the smallest was about 0.65 kb (clone no 2).

Clone 24 was sequenced on both strands using T7 and SP6 primers and the following specific primers:

Plus Strand Primers:
S4: SEQ ID NO: 7
S6: SEQ ID NO: 8
S8: SEQ ID NO: 9
Minus strand primers:
S5: SEQ ID NO: 10
S7: SEQ ID NO: 11
S9: SEQ ID NO: 12.

DNA sequencing data showed a continuous open reading frame (SEQ ID NO. 2 or NO. 13), translation into protein sequence (SEQ ID NO: 1 or NO. 14) showed several hydrophobic stretches (FIG. 23), suggesting that these regions are putative membrane spanning parts of the protein. The sequences corresponding to said hydrophobic stretches are highlighted (boxes) in FIG. 24.

SMBP appears to share structural homologies with members of a group of proteins described as <<similar>> to *Saccharomyces cerevisiae* EMP 70 protein precursor.

FIG. 22 shows that:

human myeloblastic cell line D87444 (Nagase T. et al., DNA Res., 1996, 3, 321-329) is 30% homologous to SMBP, p76 protein (Schimmöller F. et al., accession number U81006) is 27% homologous to SMBP, the yeast endomembrane protein (Emp70) which is a precursor of a 24 kDa protein (Emp24) involved in intracellular vesicular trafficking (Schimmöller F. et al., EMBO J., 1995, 14, 7, 1329-1339) is 23% homologous to SMBP, hMP70 (Chluba-de Tapia J. et al., Gene, 1997, 197, 195-204) is 28,5% homologous to SMBP whereas a protein from *Arabidopsis thaliana* (accession number U95973) is 51,2% homologous to SMDP.

The hydropathy plot of SMBP bears remarkable similarities to those of p76 protein, the myeloblast derived protein, hMP70 protein, *Arabidobsis* protein and Emp70 protein (see FIG. 23).

The affinity-labeled peptide sequence is located at the switch region between the hydrophobic N-terminal part of SMBP and the C-terminal hydrophobic stretch which contains the transmembrane regions.

The absence of N-glycosylation sites, the lack of homology with plasma membrane receptors and the similarity to intracellular proteins suggest that SMBP could indeed also be an intracellular membrane protein. SMBP appears to be expressed in many different tissues, and could therefore play a major role in normal cellular function. Since SMBP appears to be quite homologous to at least Emp70, involved in intracellular trafficking, i.e. ER via Golgi apparatus; this could also be a role for SMBP.

EXAMPLE 4

Construction of a Plasmid for the Expression of Hu-SMBP

For in vitro expression in mammalian cells, 1.7 kb cDNA insert of clone 24 was subcloned into the mammalian expression vector pcDNA3 (Invitrogen). Simultaneous cutting by restriction endonuclease Xba I and Hind III (New England Biolabs) released the 1.7 kb insert from the pcDNA I vector (see example 3). The fragment was then blunt ended using Klenow fragment (Maniatis et al., Molecular Cloning, 2nd edition, 1, 5.40) and purified on 0.7% agarose gel using QiaEX II agarose gel extraction kit (Qiagen ref. 20021).

Vector pcDNA3 was cut in the multisite linker by Eco RV (New England Biolabs) and dephosphorylated using calf intestinal alkaline phosphatase (New England Biolabs). After heat inactivation of phosphatase, the vector and the insert were ligated using T4 DNA ligase (New England Biolabs). Subclone 3 was selected (designated as clone no 24.3). This plasmid contains at least SEQ ID NO: 2.

Said recombinant plasmid may be transfected into mammalian cell lines for in vitro expression.

EXAMPLE 5

Expression of SMBP in COS Cells

COS cells were transiently transfected with a vector containing the SMBP nucleotide sequence. The antibodies raised against a synthetic peptide (α8 antibodies) corresponding to the affinity-labeled fragment of rat SMBP were used for immunoprecipitation of proteins extracted from COS cells transfected with the human SMBP cDNA and labeled by $I^{125}$iodine using the chloramine T procedure. The precipitate was then redissolved and submitted to SDS-PAGE. A single protein with an apparent molecular weight of 45 kDa was identified after autoradiography (FIG. 25).

Bibliography:

Albert A. et al., J. Biol. Chem., 1990, 265, 5825-5832.
Altschul S F et al., J. Mol. Biol. 1990, 215, 403-410.
Arunlakshana O. et al., Br. J. Pharmacol. Chemother., 1959, 14, 48-58.
Auffray C. et al., C. R. Acad. Sci. III, Sci. Vie, 1995, 318(2), 263-272.
Bensaid M. et al., FEBS Letters, 1993, 318, 223-226.
Blin N. et al., Mol. Pharmacol., 1993, 44, 1094-1104.
Blue D. R. et al., Br. J. Pharmacol., 1989, 96, 246.
Bond R. A. et al., Br. J. Pharmacol., 1988, 95, 723-734.
Croci T. et al., Pharmacol. Res. Commun., 1988, 20, 147-151.
Edman P. et al., Eur. J. Biochem., 1967, 1, 80-91.
Ek B. A. et al., Gastroenterology, 1986, 90, 408-413.
Feinberg et al., Anal. Biochem., 1983, 132, 6-13
Fontana A. et al., Fragmentation of polypeptides by chemical methods, Practical Protein
Chemistry, A handbook (edited by A. Darbre), John Willy & Sons Ltd., New York, USA. 67-120 (1986)).
Fraser C. M., Receptor Biochemistry and Methodology, 1984, vol. 4 (J. C. Venter, C. M. Fraser and J. Lindstrom, Eds), Alan R. Liss, Inc., New York, USA, 69-84.
Fujiwara et al., Life Science, 1990, 47, PL 127-132.
Guillaume J L. et al., Eur. J. Biochem., 1994, 224, 761-770.
Gocayne et al., P.N.A.S., 1987, 84, 8296-8300.
Granneman J G. et al., Mol. Pharmacol., 1991, 40, 895-899.
Hoyer D. et al., Pharmacol. Rev., 1994, 46, 157-203.
Kawasaki H. et al., Anal. Biochem., 1990, 191, 332-336.
Kirkham D. et al., Br. J. Pharmacol., 1992, 105, 231P.
Laemmli U.K., Nature, 1970, 227, 680-685.
MacDonald A. et al., Br. J. Pharmacol., 1993, 110, 1551-1555.
Machida et al., J. Biol. Chem., 1990, 265, 12960-12965.
Manara L. et al., Trends Pharmacol. Sci., 1990, 11, 229-230.
McKean J. et al., J. Pharm. Pharmacol., 1995, 47, 388-391.
McLaughlin D. P. et al., Br. J. Pharmacol., 1990, 101, 569-574.
McLaughlin D. P. et al., Br. J. Pharmacol., 1991, 103, 1351-1356.
Muzzin P. et al., J. Biol. Chem., 1991, 266, 24053-24058.
Schägger H. et al., Anal. Biochem., 1987, 166, 368-379.
Sugasawa T. et al., Eur. J. Pharmacol., 1992, 216, 207-215.
Tate K. M. et al., Eur. J. Biochem., 1991, 196, 357-361.
Towbin H. et al., Proc. Natl. Acad. Sci. USA, 1979, 76, 4350-4354.
Van der Vliet A. et al., J. Pharmacol. Exp. Ther., 1990, 255, 218-226.
Voigt et al., EMBO J., 1991, 10, 4017-4023.

As emerges from the foregoing, the invention is no way limited to those of its embodiments and modes if implementation and application which have just been described more explicitly; it encompasses, on the contrary, all variants which may occur to the specialist in the field, without departure from the scope or range of the present invention.

The invention claimed is:

1. An isolated polypeptide comprising the amino acid sequence of SEQ ID NO: 1 or SEQ ID NO: 14.

2. An isolated nucleic acid molecule comprising a nucleotide sequence encoding the isolated polypeptide of claim 1.

3. The isolated nucleic acid sequence of claim 2 comprising the nucleotide sequence of SEQ ID NO: 2 or SEQ ID NO: 13.

4. A cDNA clone, comprising an isolated nucleotide sequence according to claim 2.

5. A recombinant plasmid for cloning and/or expression, comprising the nucleotide sequence according to claim 2, inserted in a cloning site which is non-essential for replication.

6. The recombinant plasmid according to claim 5, further comprising an origin of replication for replication in a host cell, at least one gene whose expression permits selection of said host cell transformed with said plasmid, and a regulatory sequence, including a promoter permitting expression of said nucleotide sequence in said host cell.

7. The recombinant plasmid according to claim 5, comprising plasmid pcDNA3 into which is inserted, in a multisite linker, SEQ ID NO: 2, wherein said recombinant plasmid is deposited as CNCM No. I-1795.

8. A host cell transformed by a recombinant plasmid according to claim 5, comprising the elements of regulation necessary for the expression of said nucleotide sequence in said host cell.

9. The host cell according to claim 8, characterized in that it is a mammalian cell line.

10. A method for assaying a substance for agonist or antagonist activity towards said isolated polypeptide of claim 1, which method comprises:
    (a) placing the substance in contact with a transformed host cell expressing said polypeptide under conditions which permit binding between said polypeptide and an agonist or an antagonist thereto and
    (b) identifying agonist or antagonist activity by measuring inhibition of eosinophil chemotaxis; wherein an increase in said inhibition of eosinophil chemotaxis indicates that said substance has an agonist activity and a decrease in said inhibition of eosinophil chemotaxis indicates that said substance has an antagonist activity.

11. A process for studying the binding affinity of a compound for said isolated polypeptide of claim 1, which process comprises:
    (a) transforming a host cell by an expression vector comprising a nucleotide sequence coding for said isolated polypeptide,
    (b) culturing said transformed host cell under conditions which permit the expression of said isolated polypeptide encoded by said nucleotide sequence and the transfer of the expressed isolated polypeptide to the membrane of the said transformed host cell so that transmembrane sequences of said isolated polypeptide are embedded in the cell membranes of the transformed host cell;
    (c) placing said transformed host cell in contact with said compound and
    (d) measuring the quantity of said compound bound to said receptor polypeptide.

12. A process for studying the binding affinity of a compound for the isolated polypeptide of claim 1, which process comprises:
    (a) placing tissue membrane proteins comprising said polypeptide or cells expressing said polypeptide in contact with said compound; and
    (b) measuring the quantity of said compound bound to said isolated polypeptide.

13. Method of labeling a receptor polypeptide of claim 1, which method comprises:
    (a) extracting membrane proteins from a tissue containing said isolated polypeptide,
    (b) labeling said membrane proteins with [$^{125}$I]-ICYP-diazirine or another appropriate marker under blockade of α, β1, β2, β3-AR and serotonine receptors,
    (c) separating said labeled proteins by preparative SDS-PAGE electrophoresis and
    (d) extracting the radioactive band.

14. A process according to claim 12, wherein the tissue or cells comprise muscle tissue or myocytes.

15. A method according to claim 13, wherein the tissue containing said receptor polypeptide comprises rat colon tissue or human skeletal muscle tissue.

* * * * *